(12) United States Patent
Sherwood

(10) Patent No.: US 8,906,637 B2
(45) Date of Patent: Dec. 9, 2014

(54) METHODS FOR DETECTING TARGETS

(75) Inventor: Steven W. Sherwood, Los Altos, CA (US)

(73) Assignee: Danisco US Inc., Palo Alto, CA (US)

( * ) Notice: Subject to any disclaimer, the term of this patent is extended or adjusted under 35 U.S.C. 154(b) by 1792 days.

(21) Appl. No.: 11/659,648

(22) PCT Filed: Sep. 9, 2005

(86) PCT No.: PCT/US2005/032257
§ 371 (c)(1),
(2), (4) Date: Jul. 22, 2009

(87) PCT Pub. No.: WO2006/031663
PCT Pub. Date: Mar. 23, 2006

(65) Prior Publication Data
US 2009/0305307 A1 Dec. 10, 2009

Related U.S. Application Data

(60) Provisional application No. 60/609,082, filed on Sep. 10, 2004, provisional application No. 60/609,205, filed on Sep. 10, 2004.

(51) Int. Cl.
*C12Q 1/37* (2006.01)
*G01N 33/542* (2006.01)
*A61K 38/00* (2006.01)
*G01N 33/574* (2006.01)
*G01N 33/569* (2006.01)

(52) U.S. Cl.
CPC .... *G01N 33/56966* (2013.01); *G01N 33/57492* (2013.01)
USPC .............. 435/7.72; 435/4; 435/7.21; 435/7.5; 435/7.6; 436/536; 436/539; 436/546; 436/63; 436/164

(58) Field of Classification Search
USPC .............. 435/4, 6, 7.21, 7.23, 7.24, 7.5, 7.72, 435/7.9, 8, 28, 7.6; 436/513, 536, 545, 546, 436/63, 64, 539, 164
See application file for complete search history.

(56) References Cited

U.S. PATENT DOCUMENTS

| 4,458,066 A | 7/1984 | Caruthers et al. |
| 4,522,811 A | 6/1985 | Eppstein et al. |

(Continued)

FOREIGN PATENT DOCUMENTS

EP 0 379 048 A2 7/1990

OTHER PUBLICATIONS

Krieg et al. Recent Advances in Catalytic Peroxidase Histochemistry, Cellular and Molecular Biology 49 (4): 547-563 (2003).*

(Continued)

*Primary Examiner* — Gail R Gabel
(74) *Attorney, Agent, or Firm* — Danisco US Inc.

(57) ABSTRACT

The present invention provides method and compositions for detecting target molecules present on cells and tissues. In particular, the methods involve adding primary antibodies such as scFv-targeted lactamase that are directed against a target of interest (e.g., cancer markers) to a tissue sample, followed by adding a lactam-containing compound and finally a lactamase reporter system. In some preferred embodiments, the lactamase reporters are fluorescent reporters that bind to the test tissue. In some particularly preferred embodiments, the test tissue contains at least once cancer cell and/or at least one cancer-associated marker.

17 Claims, 28 Drawing Sheets

(56) References Cited

U.S. PATENT DOCUMENTS

| | | | |
|---|---|---|---|
| 4,946,778 | A | 8/1990 | Ladner et al. |
| 5,061,620 | A | 10/1991 | Tsukamoto et al. |
| 5,443,986 | A * | 8/1995 | Haughland et al. ............. 435/4 |
| 5,583,217 | A | 12/1996 | Quante et al. |
| 5,677,136 | A | 10/1997 | Simmons et al. |
| 5,750,397 | A | 5/1998 | Tsukamoto et al. |
| 6,261,535 | B1 | 7/2001 | Thorpe et al. |
| 8,318,450 | B2 * | 11/2012 | Corry et al. .................. 435/18 |
| 2004/0115742 | A1 * | 6/2004 | Tan et al. ..................... 435/7.2 |

OTHER PUBLICATIONS

Beaucage, S.L. et al. "Deoxynucleoside phosphoramidites—A new class of key intermediates for deoxypolynucleotide synthesis." *Tetrahedron Lett.* 22(20): 1859-1862, 1981.

Benito, A. et al. "Insertion of a 27 amino acid viral peptide in different zones of *Escherichia coli* β-galactosidase: Effects on the enzyme activity." *FEMS Microbiology Letters* 123(1-2): 107-112, 1994.

Boehm, M.K. et al. "Crystal structure of the anti-(carcinoembryonic antigen) single-chain Fv antibody MFE-23 and a model for antigen binding based on intermolecular contacts." *The Biochemical Journal* 346 Pt 2: 519-28, Mar. 1, 2000.

Bosslet, K. et al. "Molecular and functional characterisation of a fusion protein suited for tumour specific prodrug activation." *British Journal of Cancer* 65(2): 234-238, Feb. 1992.

Brown, E.L. et al. "Chemical synthesis and cloning of a tyrosine tRNA gene." *Methods in Enzymology*(68): 109-51, 1979.

Burgstaller, P. et al. "Aptamers and aptazymes: accelerating small molecule drug discovery." *Current Opinion in Drug Discovery & Development* 5(5): 690-700, Sep. 2002.

Cole, S.P.C. et al. "The EBV-Hybridoma Technique and its Application to Human Lung Cancer." In *Monoclonal Antibodies and Cancer Therapy*, edited by R.A. Reisfeld et al., pp. 77-96. New York: A.R. Liss, 1985.

Cote, R.J. et al. "Generation of human monoclonal antibodies reactive with cellular antigens." *Proc. Natl. Acad. Sci. U.S.A* 80(7): 2026-30, Apr. 1983.

Crawford, M. et al. "Peptide aptamers: Tools for biology and drug discovery." *Brief Funct Genomic Proteomic* 2(1): 72-79, Jan. 1, 2003.

Ferrara, N. et al. "Clinical applications of angiogenic growth factors and their inhibitors." *Nat Med* 5(12): 1359-1364, Dec. 1999.

Gerber, H.-P. et al. "VEGF couples hypertrophic cartilage remodeling, ossification and angiogenesis during endochondral bone formation." *Nat Med* 5(6): 623-628, Jun. 1999.

Giovannangeli, C. et al. "Triplex-forming molecules for modulation of DNA information processing." *Current Opinion in Molecular Therapeutics* 2(3): 288-296, Jun. 2000.

Goodchild, J. "Conjugates of oligonucleotides and modified oligonucleotides: a review of their synthesis and properties." *Bioconjug. Chem* 1(3): 165-87, 1990.

Goshorn, S.C. et al. "Genetic Construction, Expression, and Characterization of a Single Chain Anti-Carcinoma Carcinoma Antibody Fused to β-Lactamase." *Cancer Res* 53(9): 2123-2127, May 1, 1993.

Hardman, J.G. et al., eds. "Table 45-2: Names, Structural Formulas, Dosage, and Dosage Forms of Selected Cephalosporins and Related Compounds." In *Goodman and Gilman's The Pharmacological Basis of Therapeutics*, pp. 1090-1. New York: McGraw-Hill, 1996.

Huse, W.D. et al. "Generation of a large combinatorial library of the immunoglobulin repertoire in phage lambda." *Science* 246(4935): 1275-1281, Dec. 8, 1989.

Kerr, D.E. et al. "Regressions and Cures of Melanoma Xenografts following Treatment with Monoclonal Antibody β-Lactamase Conjugates in Combination with Anticancer Prodrugs." *Cancer Res* 55(16): 3558-3563, Aug. 15, 1995.

Köhler, G. et al. "Continuous cultures of fused cells secreting antibody of predefined specificity." *Nature* 256(5517): 495-497, 1975.

Kozbor, D. et al. "The production of monoclonal antibodies from human lymphocytes." *Immunology Today* 4(3): 72-79, Mar. 1983.

Krieg, R. et al. "Recent advances in catalytic peroxidase histochemistry." *Cellular and Molecular Biology* (Noisy-Le-Grand, France) 49(4): 547-563, Jun. 2003.

Matteucci, M. "Oligonucleotide analogues: an overview." In *Oligonucleotides as Therapeutic Agents*, edited by D.J. Chadwick et al., pp. 5-18. Ciba Foundation Symposium 209. Chichester, England: John Wiley & Sons, 1997.

Napolitano, E.W. et al. "Glubodies: randomized libraries of glutathione transferase enzymes." *Chemistry & Biology* 3(5): 359-367, May 1996.

Narang, S.A. et al. "Improved phosphotriester method for the synthesis of gene fragments." *Meth. Enzymol* 68: 90-8, 1979.

Nielsen, P.E. "Targeting Double Stranded DNA with Peptide Nucleic Acid (PNA)." *Current Medicinal Chemistry* 8: 545-550, May 2001.

Rodrigues, M.L. et al. "Development of a Humanized Disulfide-stabilized Anti-p185HER2 Fv-β-Lactamase Fusion Protein for Activation of a Cephalosporin Doxorubicin Prodrug." *Cancer Res* 55(1): 63-70, Jan. 1, 1995.

Senter, P.D. et al. "Generation of cytotoxic agents by targeted enzymes." *Bioconjugate Chemistry* 4(1): 3-9, Jan. 1, 1993.

Siemers, N.O. et al. "Construction, Expression, and Activities of L49-sFv-β-Lactamase, a Single-Chain Antibody Fusion Protein for Anticancer Prodrug Activation." *Bioconjugate Chemistry* 8(4): 510-519, Jul. 1, 1997.

Smith, J.W. et al. "Protein Loop Grafting to Construct a Variant of Tissue-type Plasminogen Activator That Binds Platelet Integrin αIIbβ3." *J. Biol. Chem.* 270(51): 30486-30490, Dec. 22, 1995.

Stein, D. et al. "A Specificity Comparison of Four Antisense Types: Morpholino, 2'-O-Methyl RNA, DNA, and Phosphorothioate DNA." *Antisense and Nucleic Acid Drug Development* 7(3): 151-157, Jun. 1, 1997.

Summerton, J. et al. "Morpholino and Phosphorothioate Antisense Oligomers Compared in Cell-Free and In-Cell Systems." *Antisense and Nucleic Acid Drug Development* 7(2): 63-70, Apr. 1, 1997.

de Sutter, K. et al. "A bifunctional murine::Human chimeric antibody with one antigen-binding arm replaced by bacterial β-lactamase." *Molecular Immunology* 31(4): 261-267, Mar. 1994.

Svensson, H.P. et al. "In Vitro and in Vivo Activities of a Doxorubicin Prodrug in Combination with Monoclonal Antibody β-Lactamase Conjugates." *Cancer Res* 55(11): 2357-2365, Jun. 1, 1995.

Vasquez, K.M. et al. "Triplex-directed modification of genes and gene activity." *Trends in Biochemical Sciences* 23(1): 4-9, Jan. 1998.

Yolken, R.H. et al. "Enzyme immunoassays in which biotinillated beta-lactamase is used for the detection of microbial antigens." *J. Clin. Microbiol.* 19(3): 356-360, Mar. 1, 1984.

\* cited by examiner

Amino Acid Sequence of BLA Protein

```
  1  TPVSEKQLAE VVANTITPLM KAQSVPGMAV AVIYQGKPHY YTFGKADIAA
 51  NKPVTPQTLF ELGSISKTFT GVLGGDAIAR GEISLDDAVT RYWPQLTGKQ
101  WQGIRMLDLA TYTAGGLPLQ VPDEVTDNAS LLRFYQNWQP QWKPGTTRLY
151  ANASIGLFGA LAVKPSGMPY EQAMTTRVLK PLKLDHTWIN VPKAEEAHYA
201  WGYRDGKAVR VSPGMLDAQA YGVKTNVQDM ANWVMANMAP ENVADASLKQ
251  GIALAQSRYW RIGSMYQGLG WEMLNWPVEA NTVVETSFGN VALAPLPVAE
301  VNPPAPPVKA SWVHKTGSTG GFGSYVAFIP EKQIGIVMLA NTSYPNPARV
351  EAAYHILEAL Q (SEQ ID NO:2)
```

FIG. 1A

Nucleotide Sequence of BLA Gene

```
   1  ACACCGGTGT CAGAAAAACA GCTGGCGGAG GTGGTCGCGA ATACGATTAC
  51  CCCGCTGATG AAAGCCCAGT CTGTTCCAGG CATGGCGGTG GCCGTTATTT
 101  ATCAGGGAAA ACCGCACTAT TACACATTTG GCAAGGCCGA TATCGCGGCG
 151  AATAAACCCG TTACGCCTCA GACCCTGTTC GAGCTGGGTT CTATAAGTAA
 201  AACCTTCACC GGCGTTTTAG GTGGGGATGC CATTGCTCGC GGTGAAATTT
 251  CGCTGGACGA TGCGGTGACC AGATACTGGC CACAGCTGAC GGGCAAGCAG
 301  TGGCAGGGTA TTCGTATGCT GGATCTCGCC ACCTACACCG CTGGCGGCCT
 351  GCCGCTACAG GTACCGGATG AGGTCACGGA TAACGCCTCC CTGCTGCGCT
 401  TTTATCAAAA CTGGCAGCCG CAGTGGAAGC CTGGCACAAC GCGTCTTTAC
 451  GCCAACGCCA GCATCGGTCT TTTTGGTGCG CTGGCGGTCA AACCTTCTGG
 501  CATGCCCTAT GAGCAGGCCA TGACGACGCG GGTCCTTAAG CCGCTCAAGC
 551  TGGACCATAC CTGGATTAAC GTGCCGAAAG CGGAAGAGGC GCATTACGCC
 601  TGGGGCTATC GTGACGGTAA AGCGGTGCGC GTTTCGCCGG GTATGCTGGA
 651  TGCACAAGCC TATGGCGTGA AAACCAACGT GCAGGATATG GCGAACTGGG
 701  TCATGGCAAA CATGGCGCCG GAGAACGTTG CTGATGCCTC ACTTAAGCAG
 751  GGCATCGCGC TGGCGCAGTC GCGCTACTGG CGTATCGGGT CAATGTATCA
 801  GGGTCTGGGC TGGGAGATGC TCAACTGGCC CGTGGAGGCC AACACGGTGG
 851  TCGAGACGAG TTTTGGTAAT GTAGCACTGG CGCCGTTGCC CGTGGCAGAA
 901  GTGAATCCAC CGGCTCCCCC GGTCAAAGCG TCCTGGGTCC ATAAAACGGG
 951  CTCTACTGGC GGGTTTGGCA GCTACGTGGC CTTTATTCCT GAAAAGCAGA
1001  TCGGTATTGT GATGCTCGCG AATACAAGCT ATCCGAACCC GGCACGCGTT
1051  GAGGCGGCAT ACCATATCCT CGAGGCGCTA CAG (SEQ ID NO:1)
```

FIG. 1B

Precipitating Fluorogenic Lactamase Reporter

MPR 71439

7-(2-thienylaetamido)-3-(3-(6-chloro-4(3H)-quinazolinone)
4-chlorophenyloxymethyl-Δ³-cephem-4-carboxylic acid. S-oxide

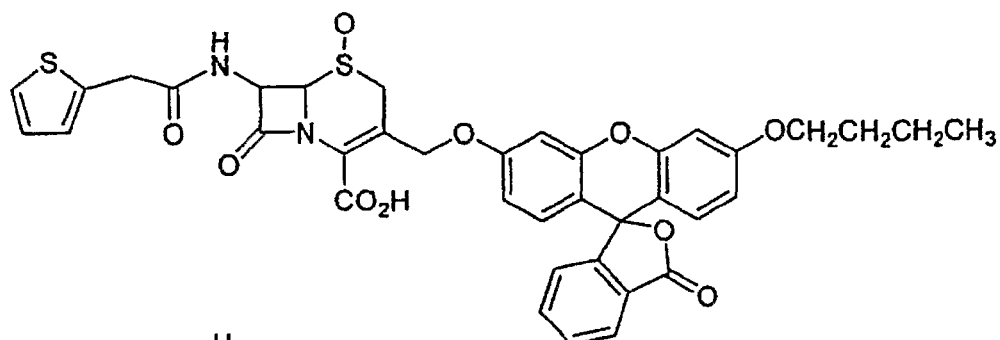
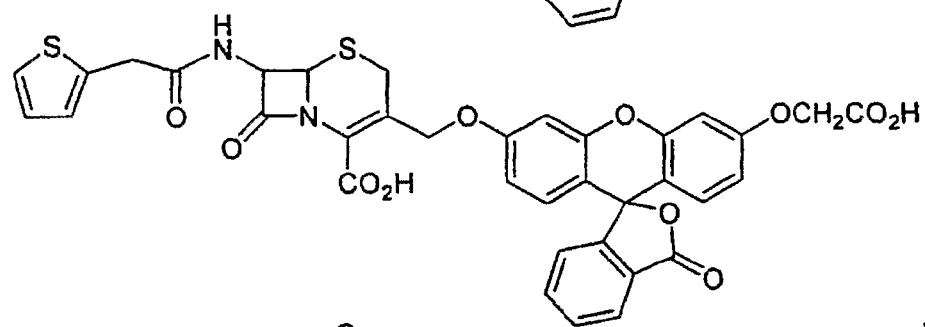
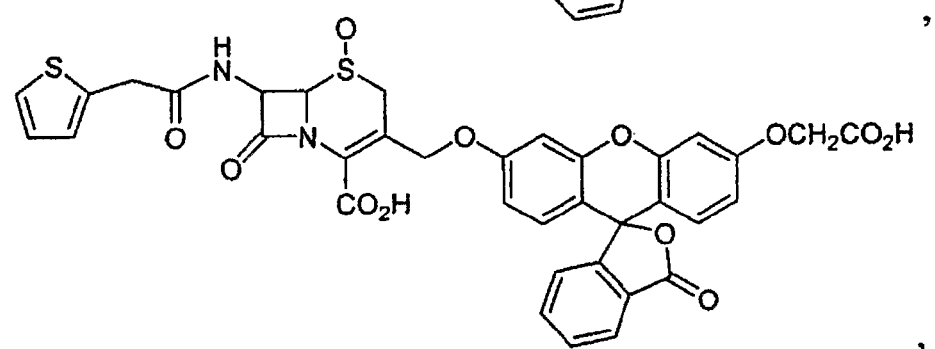
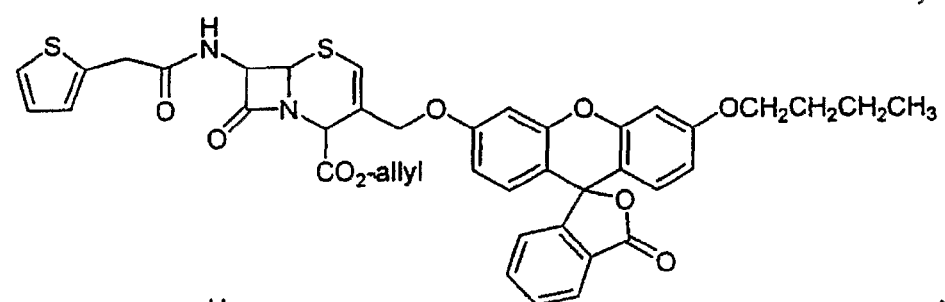
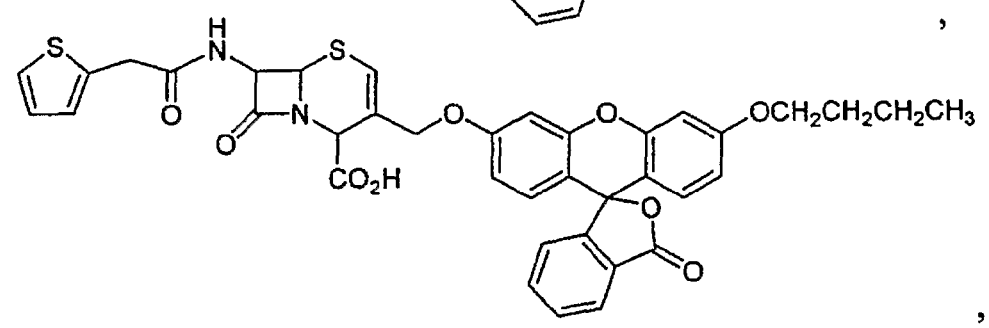
*FIG. 2E*

Viable Cell Staining in Mixed Culture of CEA-positive
and CEA-negative Mouse Fibroblasts Human Tissue Microarray (TMS)
Comprising Normal and Cancer Tissues

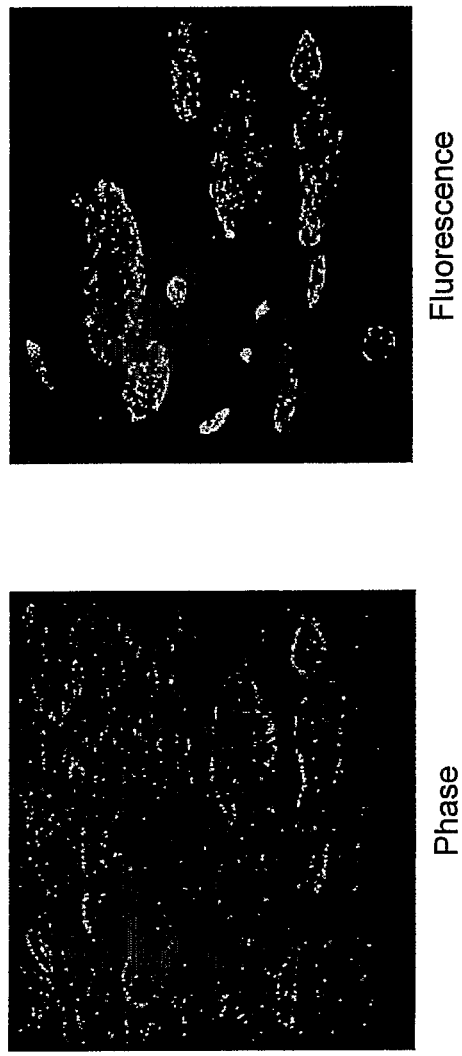

FIG. 4A Phase — LS174T/MRC5 Mixed Cell Model Tumor Cell/Stroma Model. LS174T. CEA-expressing human colon carcinoma cells MRC5. Primary human diploid fibroblasts cells were fixed, washed and treated with Cab1.2 (.5ug/ml), washed and treated with reporter for 5 minutes.

FIG. 4B Fluorescence — LS174T/MRC5 Mixed Cell Model Tumor Cell/Stroma Model. LS174T. CEA-expressing human colon carcinoma cells MRC5. Primary human diploid fibroblasts cells were fixed, washed and treated with Cab1.2 (.5ug/ml), washed and treated with reporter for 5 minutes.

FIG. 4C Combined — LS174T/MRC5 Mixed Cell Model Tumor Cell/Stroma Model. LS174T. CEA-expressing human colon carcinoma cells MRC5. Primary human diploid fibroblasts cells were fixed, washed and treated with Cab1.2 (.5ug/ml), washed and treated with reporter for 5 minutes.

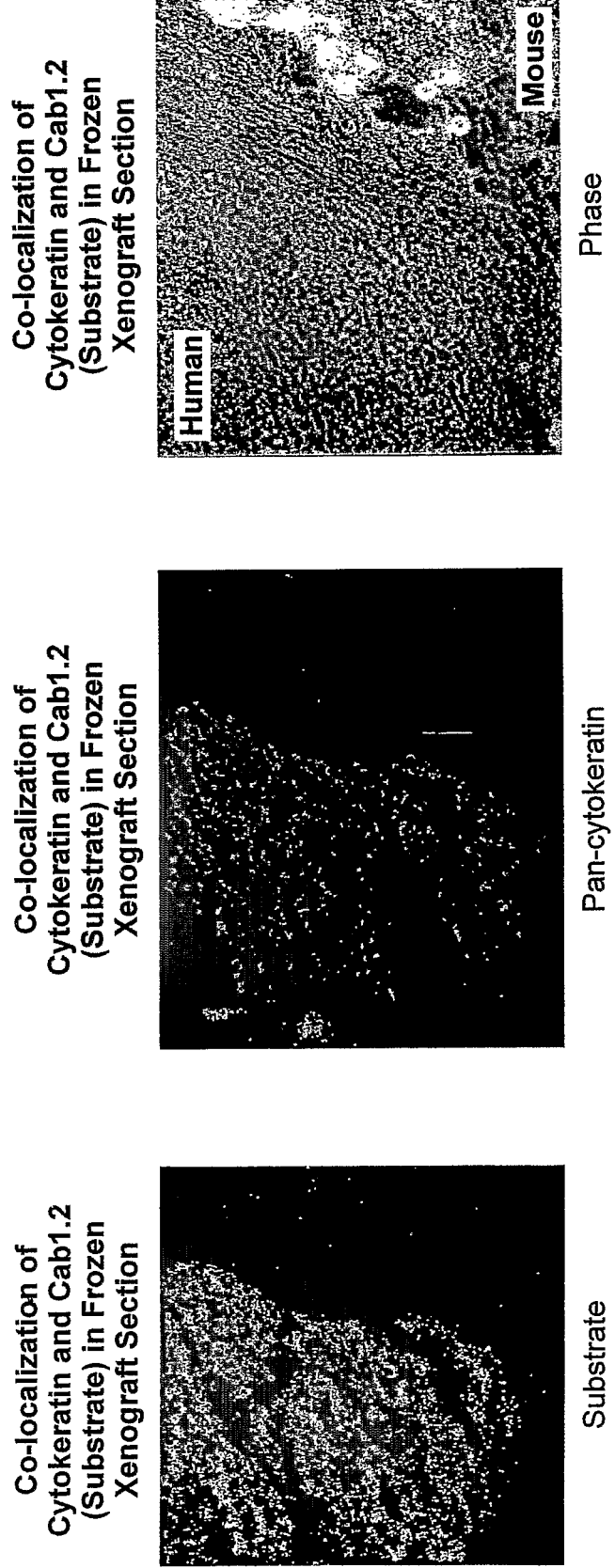

HTS-TMA'S

Paraffin-imbedded Human Colon Cancer Tissue Stained with Biotinylated anti-CEA (Biomeda), Streptavidin and Biotinylated bla Followed by Substrate Heavy Chain:
qvklqqsgaelvrsgtsvklsctasgfnikdsymhwlrggpeqglewigwidpengdteyapkfqgkatfttdtssntaylqlssltsedtavyycnegtptgpyyfdywggttvtvss
(SEQ ID NO:3)

Linker:
ggggsggggsggggs (SEQ ID NO:5)

Light Chain:
envltqspaimsaspgekvtitcsasssvsymhwfqqkpgtspklwiystsnlasgvparfsgsgsgtsysltisrmeaedaatyycqqrssyppltfgagtklelkraat
(SEQ ID NO:4)

BLA:
pvsekqlaevvantitplmkaqsvpgmavaviyqgkphyytfgkadiaankpvtpqtlfelgsisktftgvlggdaiargeislddavtrywpqltgkqwqgirmldlatytagglplqv
pdevtdnasllrfyqnwqpqwkpgttrlyanasiglfgalavkpsgmpyeqamttrvlkplkldhtwinvpkaeeahyawgyrdgkavrvspgmldaqaygvktnvqdmanwvmanmape
nvadaslkqgialaqsrywrigsmyqglgwemlnwpveantvvetsfgnvalaplpvaevnppappvkaswvhktgstgfgsyvafipekqigivmlantsypnparveaayhilealq
(SEQ ID NO:6)

FIG. 12B

| | | | | | | | | | | | | | | |
|---|---|---|---|---|---|---|---|---|---|---|---|---|---|---|
| 48 | 185 | V | 0.481 | M | | | I | 0.173 | L | 0.124 | | | | I | |
| 49 | 185 | G | 0.600 | S | 0.216 | A | 0.162 | E | 0.005 | L | 0.005 | I | 0.005 | G | |
| 50 | 185 | R | 0.146 | W | 0.146 | V | 0.119 | A | 0.114 | G | 0.081 | Y | 0.081 | W | H2 |
| 51 | 185 | I | 0.822 | T | 0.081 | R | 0.027 | V | 0.022 | K | 0.016 | M | 0.011 | I | H2 |
| 52 | 184 | S | 0.250 | Y | 0.239 | N | 0.123 | K | 0.060 | I | 0.054 | D | 0.050 | D | H2 |
| 52a | 141 | - | 0.230 | P | 0.180 | Y | 0.153 | G | 0.126 | N | 0.066 | V | 0.055 | P | H2 |
| 52b | 34 | - | 0.814 | K | 0.115 | R | 0.060 | G | 0.005 | Y | 0.005 | | | | H2 |
| 52c | 22 | - | 0.880 | T | 0.044 | V | 0.033 | S | 0.022 | A | 0.011 | G | 0.005 | | H2 |
| 53 | 184 | S | 0.228 | D | 0.163 | Y | 0.125 | G | 0.109 | N | 0.082 | H | 0.054 | E | H2 |
| 54 | 183 | G | 0.328 | S | 0.202 | D | 0.129 | N | 0.112 | K | 0.082 | F | 0.055 | N | H2 |
| 55 | 182 | G | 0.544 | S | 0.181 | D | 0.085 | W | 0.066 | Y | 0.060 | N | 0.020 | G | H2 |
| 56 | 182 | S | 0.231 | D | 0.182 | N | 0.147 | T | 0.143 | Y | 0.077 | G | 0.060 | D | H2 |
| 57 | 184 | T | 0.582 | K | 0.120 | N | 0.065 | A | 0.054 | I | 0.054 | P | 0.022 | T | H2 |
| 58 | 183 | Y | 0.322 | N | 0.216 | D | 0.139 | R | 0.060 | H | 0.055 | T | 0.038 | E | H2 |
| 59 | 184 | Y | 0.908 | F | 0.043 | N | 0.016 | S | 0.011 | D | 0.005 | G | 0.005 | Y | H2 |
| 60 | 183 | A | 0.579 | N | 0.153 | S | 0.104 | T | 0.055 | R | 0.044 | G | 0.027 | A | H2 |
| 61 | 184 | D | 0.277 | P | 0.239 | Q | 0.174 | A | 0.141 | V | 0.076 | T | 0.033 | P | H2 |
| 62 | 185 | S | 0.686 | K | 0.146 | P | 0.065 | N | 0.038 | G | 0.016 | R | 0.016 | K | H2 |
| 63 | 186 | V | 0.511 | L | 0.247 | F | 0.215 | S | 0.011 | A | 0.005 | K | 0.005 | F | H2 |
| 64 | 186 | K | 0.581 | Q | 0.274 | R | 0.054 | N | 0.032 | E | 0.022 | T | 0.022 | Q | H2 |
| 65 | 186 | G | 0.688 | S | 0.237 | T | 0.032 | A | 0.016 | D | 0.011 | E | 0.011 | G | H2 |
| 66 | 186 | R | 0.935 | Q | 0.054 | H | 0.005 | I | 0.005 | | | | | K | 1 |
| 67 | 186 | F | 0.462 | V | 0.409 | I | 0.065 | L | 0.054 | A | 0.005 | S | 0.005 | A | 1 |
| 68 | 186 | T | 0.914 | I | 0.038 | A | 0.016 | S | 0.011 | K | 0.005 | N | 0.005 | T | |
| 69 | 187 | I | 0.791 | M | 0.139 | V | 0.032 | D | 0.005 | F | 0.005 | G | 0.005 | F | 1 |
| 70 | 187 | S | 0.684 | T | 0.214 | N | 0.070 | L | 0.032 | | | | | T | |
| 71 | 187 | R | 0.529 | V | 0.160 | A | 0.107 | P | 0.064 | T | 0.053 | K | 0.043 | T | 1 |
| 72 | 186 | D | 0.902 | N | 0.071 | K | 0.016 | E | 0.011 | | | | | D | |
| 73 | 185 | T | 0.368 | N | 0.266 | D | 0.177 | K | 0.070 | E | 0.059 | A | 0.011 | T | |
| 74 | 186 | S | 0.946 | A | 0.048 | L | 0.005 | | | | | | | S | |
| 75 | 187 | K | 0.674 | T | 0.139 | I | 0.070 | R | 0.027 | A | 0.021 | F | 0.021 | S | 1 |
| 76 | 187 | N | 0.701 | S | 0.251 | K | 0.027 | R | 0.011 | T | 0.005 | Y | 0.005 | N | |
| 77 | 187 | T | 0.615 | Q | 0.273 | S | 0.048 | M | 0.021 | L | 0.016 | P | 0.011 | T | |
| 78 | 186 | L | 0.364 | A | 0.273 | F | 0.235 | V | 0.096 | I | 0.005 | M | 0.005 | A | |
| 79 | 187 | Y | 0.638 | S | 0.239 | F | 0.059 | V | 0.048 | H | 0.005 | M | 0.005 | Y | |
| 80 | 187 | L | 0.782 | M | 0.207 | N | 0.005 | - | 0.005 | | | | | L | |
| 81 | 187 | Q | 0.529 | E | 0.205 | K | 0.122 | R | 0.032 | T | 0.032 | N | 0.027 | Q | |
| 82 | 194 | M | 0.497 | L | 0.421 | W | 0.051 | V | 0.015 | I | 0.010 | - | 0.005 | L | |
| 82a | 195 | N | 0.442 | S | 0.291 | R | 0.077 | T | 0.066 | D | 0.053 | G | 0.020 | S | |
| 82b | 194 | S | 0.795 | N | 0.082 | R | 0.051 | G | 0.026 | T | 0.021 | A | 0.010 | S | |
| 82c | 197 | L | 0.701 | V | 0.234 | M | 0.041 | G | 0.010 | A | 0.005 | D | 0.005 | L | |
| 83 | 197 | R | 0.528 | T | 0.239 | K | 0.122 | D | 0.041 | E | 0.020 | Q | 0.015 | T | |
| 84 | 198 | A | 0.495 | P | 0.182 | S | 0.177 | T | 0.051 | I | 0.035 | V | 0.030 | S | |
| 85 | 198 | E | 0.591 | A | 0.172 | D | 0.126 | S | 0.051 | V | 0.045 | G | 0.015 | E | |
| 86 | 198 | D | 0.975 | T | 0.010 | V | 0.010 | N | 0.005 | | | | | D | |
| 87 | 198 | T | 0.929 | S | 0.035 | G | 0.010 | M | 0.010 | A | 0.005 | Q | 0.005 | T | |
| 88 | 198 | A | 0.939 | G | 0.040 | P | 0.005 | T | 0.005 | V | 0.005 | Y | 0.005 | A | |
| 89 | 198 | V | 0.768 | L | 0.066 | M | 0.056 | T | 0.045 | I | 0.040 | F | 0.010 | V | |
| 90 | 199 | Y | 0.980 | F | 0.010 | A | 0.005 | I | 0.005 | | | | | Y | |
| 91 | 199 | Y | 0.930 | F | 0.045 | C | 0.015 | R | 0.005 | T | 0.005 | | | Y | |
| 92 | 198 | C | 0.990 | A | 0.005 | M | 0.005 | | | | | | | C | |
| 93 | 198 | A | 0.838 | T | 0.076 | V | 0.061 | H | 0.005 | K | 0.005 | N | 0.005 | N | 1 |
| 94 | 198 | R | 0.596 | K | 0.162 | T | 0.051 | G | 0.045 | P | 0.045 | Q | 0.025 | E | 1 |
| 95 | 161 | G | 0.174 | D | 0.120 | E | 0.099 | A | 0.093 | N | 0.092 | P | 0.068 | G | |
| 96 | 159 | P | 0.168 | R | 0.130 | G | 0.112 | L | 0.062 | V | 0.062 | Y | 0.062 | T | H3 |
| 97 | 156 | G | 0.170 | P | 0.094 | V | 0.094 | E | 0.088 | T | 0.069 | S | 0.063 | P | H3 |
| 98 | 155 | G | 0.152 | Y | 0.101 | L | 0.095 | D | 0.087 | V | 0.076 | S | 0.063 | T | H3 |

*FIG. 13A*

| Pos. Light Chain | Number of Observations | Observed Frequencies of 5 Most Abundant Amino Acids in Alignment of Human Sequences | | | | | | | | | | | CAB1 Sequence | CDR | Mutated Residues |
|---|---|---|---|---|---|---|---|---|---|---|---|---|---|---|---|
| 1 | 95 | Q | 0.589 | S | 0.158 | N | 0.095 | H | 0.074 | D | 0.053 | F | 0.021 | E | | 1 |
| 2 | 139 | S | 0.446 | Y | 0.388 | F | 0.101 | V | 0.043 | L | 0.014 | T | 0.007 | N | | 1 |
| 3 | 140 | V | 0.307 | E | 0.243 | A | 0.207 | M | 0.093 | D | 0.064 | I | 0.043 | V | | |
| 4 | 140 | L | 0.971 | V | 0.029 | | | | | | | | | L | | |
| 5 | 141 | T | 0.915 | A | 0.021 | S | 0.021 | I | 0.014 | K | 0.007 | L | 0.007 | T | | |
| 6 | 140 | Q | 0.993 | E | 0.007 | | | | | | | | | Q | | |
| 7 | 139 | P | 0.906 | D | 0.029 | S | 0.029 | A | 0.022 | E | 0.014 | | | S | | 1 |
| 8 | 139 | P | 0.741 | A | 0.137 | H | 0.072 | R | 0.029 | L | 0.007 | S | 0.007 | P | | |
| 9 | 139 | S | 0.964 | A | 0.014 | V | 0.014 | R | 0.007 | | | | | A | | 1 |
| 10 | 0 | - | 1.000 | | | | | | | | | | | I | | 1 |
| 11 | 138 | V | 0.790 | A | 0.138 | L | 0.058 | M | 0.014 | | | | | M | | 1 |
| 12 | 139 | S | 0.978 | F | 0.007 | T | 0.007 | E | 0.004 | Q | 0.004 | | | S | | |
| 13 | 138 | V | 0.406 | G | 0.348 | A | 0.138 | E | 0.087 | L | 0.014 | D | 0.007 | A | | |
| 14 | 135 | S | 0.630 | A | 0.230 | T | 0.111 | D | 0.007 | F | 0.007 | G | 0.007 | S | | |
| 15 | 135 | P | 0.881 | L | 0.089 | A | 0.022 | S | 0.007 | | | | | P | | |
| 16 | 134 | G | 0.978 | E | 0.015 | L | 0.007 | | | | | | | G | | |
| 17 | 133 | Q | 0.811 | K | 0.098 | A | 0.045 | E | 0.024 | G | 0.015 | H | 0.008 | E | | 1 |
| 18 | 133 | T | 0.504 | S | 0.263 | R | 0.135 | K | 0.068 | E | 0.008 | G | 0.008 | K | | 1 |
| 19 | 130 | V | 0.454 | A | 0.385 | I | 0.146 | G | 0.008 | L | 0.008 | | | V | | |
| 20 | 128 | T | 0.531 | R | 0.188 | S | 0.148 | K | 0.047 | I | 0.031 | M | 0.016 | T | | |
| 21 | 121 | I | 0.901 | V | 0.050 | L | 0.017 | A | 0.008 | F | 0.008 | M | 0.008 | I | | |
| 22 | 120 | S | 0.492 | T | 0.475 | A | 0.008 | G | 0.008 | I | 0.008 | N | 0.008 | T | | |
| 23 | 117 | C | 1.000 | | | | | | | | | | | C | | |
| 24 | 112 | S | 0.536 | T | 0.259 | G | 0.089 | A | 0.045 | Q | 0.033 | I | 0.018 | S | L1 | |
| 25 | 108 | G | 0.870 | L | 0.056 | R | 0.028 | A | 0.019 | I | 0.009 | P | 0.009 | A | L1 | |
| 26 | 108 | D | 0.339 | S | 0.250 | T | 0.213 | N | 0.087 | E | 0.037 | G | 0.037 | S | L1 | |
| 27 | 104 | S | 0.415 | N | 0.118 | K | 0.113 | A | 0.104 | T | 0.066 | G | 0.047 | S | L1 | |
| 28 | 104 | L | 0.346 | S | 0.346 | I | 0.115 | G | 0.067 | A | 0.058 | D | 0.019 | S | L1 | |
| 29 | 100 | G | 0.243 | N | 0.239 | D | 0.159 | S | 0.078 | P | 0.068 | H | 0.058 | V | L1 | |
| 30 | 103 | I | 0.291 | V | 0.165 | D | 0.136 | N | 0.107 | E | 0.058 | S | 0.049 | S | L1 | |
| 31 | 101 | G | 0.356 | K | 0.168 | A | 0.099 | E | 0.084 | Q | 0.084 | D | 0.069 | Y | L1 | |
| 31a | 54 | - | 0.438 | S | 0.167 | G | 0.104 | N | 0.083 | Y | 0.063 | D | 0.052 | M | L1 | |
| 31b | 49 | - | 0.495 | N | 0.227 | Y | 0.155 | S | 0.041 | G | 0.021 | H | 0.021 | H | L1 | |
| 31c | 23 | - | 0.760 | N | 0.134 | S | 0.031 | K | 0.021 | D | 0.012 | E | 0.010 | | L1 | |
| 31d | 0 | - | 1.000 | | | | | | | | | | | | L1 | |
| 31e | 0 | - | 1.000 | | | | | | | | | | | | L1 | |
| 31f | 0 | - | 1.000 | | | | | | | | | | | | L1 | |
| 32 | 94 | Y | 0.515 | S | 0.134 | F | 0.093 | A | 0.072 | T | 0.052 | H | 0.041 | | L1 | |
| 33 | 97 | V | 0.680 | A | 0.186 | I | 0.082 | Y | 0.021 | F | 0.010 | P | 0.010 | | L1 | |
| 34 | 92 | S | 0.380 | H | 0.120 | A | 0.109 | Y | 0.098 | N | 0.076 | Q | 0.076 | | L1 | |
| 35 | 98 | W | 0.990 | Y | 0.010 | | | | | | | | | W | | |
| 36 | 96 | Y | 0.844 | F | 0.073 | H | 0.073 | W | 0.010 | | | | | F | | 1 |
| 37 | 95 | Q | 0.916 | R | 0.042 | E | 0.011 | H | 0.011 | K | 0.011 | Y | 0.011 | Q | | |
| 38 | 94 | Q | 0.862 | H | 0.053 | L | 0.053 | E | 0.011 | K | 0.011 | V | 0.011 | Q | | |
| 39 | 93 | K | 0.333 | L | 0.172 | R | 0.161 | H | 0.151 | Q | 0.086 | V | 0.043 | K | | |
| 40 | 93 | P | 0.946 | S | 0.022 | A | 0.011 | L | 0.011 | R | 0.011 | | | P | | |

*FIG. 13B*

114AR -
Excitation 535;
Emission 600

114AR -
Excitation 535;
Emission 670

114AR -
Excitation 535;
Emission 670

114AR -
Excitation 625:
Emission 670

116AR/146AR -
Excitation 465;
Emission 535

116AR/146AR - Excitation 465; Emission 600

SEQUENCE LISTING

```
<160> NUMBER OF SEQ ID NOS: 39

<210> SEQ ID NO 1
<211> LENGTH: 1083
<212> TYPE: DNA
<213> ORGANISM: Artificial Sequence
<220> FEATURE:
<223> OTHER INFORMATION: beta-lactamase protein encoding sequence

<400> SEQUENCE: 1
acaccggtgt cagaaaaaca gctggcggag gtggtcgcga atacgattac cccgctgatg      60
aaagcccagt ctgttccagg catggcggtg gccgttattt atcagggaaa accgcactat     120
tacacatttg gcaaggccga tatcgcggcg aataaacccg ttacgcctca gaccctgttc     180
gagctgggtt ctataagtaa aaccttcacc ggcgttttag gtggggatgc cattgctcgc     240
ggtgaaattt cgctggacga tgcggtgacc agatactggc cacagctgac gggcaagcag     300
tggcagggta ttcgtatgct ggatctcgcc acctacaccg ctggcggcct gccgctacag     360
gtaccggatg aggtcacgga taacgcctcc ctgctgcgct tttatcaaaa ctggcagccg     420
cagtggaagc ctggcacaac gcgtctttac gccaacgcca gcatcggtct ttttggtgcg     480
ctggcggtca aaccttctgg catgccctat gagcaggcca tgacgacgcg ggtccttaag     540
ccgctcaagc tggaccatac ctggattaac gtgccgaaag cggaagaggc gcattacgcc     600
tggggctatc gtgacggtaa agcggtgcgc gtttcgccgg gtatgctgga tgcacaagcc     660
tatggcgtga aaaccaacgt gcaggatatg gcgaactggg tcatggcaaa catggcgccg     720
gagaacgttg ctgatgcctc acttaagcag ggcatcgcgc tggcgcagtc gcgctactgg     780
cgtatcgggt caatgtatca gggtctgggc tgggagatgc tcaactggcc cgtggaggcc     840
aacacggtgg tcgagacgag ttttggtaat gtagcactgg cgccgttgcc cgtggcagaa     900
gtgaatccac cggctccccc ggtcaaagcg tcctgggtcc ataaaacggg ctctactggc     960
gggtttggca gctacgtggc ctttattcct gaaaagcaga tcggtattgt gatgctcgcg    1020
aatacaagct atccgaaccc ggcacgcgtt gaggcggcat accatatcct cgaggcgcta    1080
cag                                                                 1083

<210> SEQ ID NO 2
<211> LENGTH: 361
<212> TYPE: PRT
<213> ORGANISM: Artificial Sequence
```

<220> FEATURE:
<223> OTHER INFORMATION: beta-lactamase protein

<400> SEQUENCE: 2

```
Thr Pro Val Ser Glu Lys Gln Leu Ala Glu Val Val Ala Asn Thr Ile
 1               5                  10                  15

Thr Pro Leu Met Lys Ala Gln Ser Val Pro Gly Met Ala Val Ala Val
             20                  25                  30

Ile Tyr Gln Gly Lys Pro His Tyr Tyr Thr Phe Gly Lys Ala Asp Ile
         35                  40                  45

Ala Ala Asn Lys Pro Val Thr Pro Gln Thr Leu Phe Glu Leu Gly Ser
     50                  55                  60

Ile Ser Lys Thr Phe Thr Gly Val Leu Gly Gly Asp Ala Ile Ala Arg
 65                  70                  75                  80

Gly Glu Ile Ser Leu Asp Asp Ala Val Thr Arg Tyr Trp Pro Gln Leu
                 85                  90                  95

Thr Gly Lys Gln Trp Gln Gly Ile Arg Met Leu Asp Leu Ala Thr Tyr
            100                 105                 110

Thr Ala Gly Gly Leu Pro Leu Gln Val Pro Asp Glu Val Thr Asp Asn
        115                 120                 125

Ala Ser Leu Leu Arg Phe Tyr Gln Asn Trp Gln Pro Gln Trp Lys Pro
    130                 135                 140

Gly Thr Thr Arg Leu Tyr Ala Asn Ala Ser Ile Gly Leu Phe Gly Ala
145                 150                 155                 160

Leu Ala Val Lys Pro Ser Gly Met Pro Tyr Glu Gln Ala Met Thr Thr
                165                 170                 175

Arg Val Leu Lys Pro Leu Lys Leu Asp His Thr Trp Ile Asn Val Pro
            180                 185                 190

Lys Ala Glu Glu Ala His Tyr Ala Trp Gly Tyr Arg Asp Gly Lys Ala
        195                 200                 205

Val Arg Val Ser Pro Gly Met Leu Asp Ala Gln Ala Tyr Gly Val Lys
    210                 215                 220

Thr Asn Val Gln Asp Met Ala Asn Trp Val Met Ala Asn Met Ala Pro
225                 230                 235                 240

Glu Asn Val Ala Asp Ala Ser Leu Lys Gln Gly Ile Ala Leu Ala Gln
                245                 250                 255

Ser Arg Tyr Trp Arg Ile Gly Ser Met Tyr Gln Gly Leu Gly Trp Glu
            260                 265                 270

Met Leu Asn Trp Pro Val Glu Ala Asn Thr Val Val Glu Thr Ser Phe
        275                 280                 285

Gly Asn Val Ala Leu Ala Pro Leu Pro Val Ala Glu Val Asn Pro Pro
    290                 295                 300

Ala Pro Pro Val Lys Ala Ser Trp Val His Lys Thr Gly Ser Thr Gly
305                 310                 315                 320

Gly Phe Gly Ser Tyr Val Ala Phe Ile Pro Glu Lys Gln Ile Gly Ile
                325                 330                 335

Val Met Leu Ala Asn Thr Ser Tyr Pro Asn Pro Ala Arg Val Glu Ala
            340                 345                 350

Ala Tyr His Ile Leu Glu Ala Leu Gln
        355                 360

<210> SEQ ID NO 3
<211> LENGTH: 120
<212> TYPE: PRT
<213> ORGANISM: Artificial Sequence
```

```
<220> FEATURE:
<223> OTHER INFORMATION: CAB heavy chain

<400> SEQUENCE: 3

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser
        115                 120

<210> SEQ ID NO 4
<211> LENGTH: 110
<212> TYPE: PRT
<213> ORGANISM: Artificial Sequence
<220> FEATURE:
<223> OTHER INFORMATION: CAB light chain

<400> SEQUENCE: 4

Glu Asn Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys Arg Ala Ala Thr
            100                 105                 110

<210> SEQ ID NO 5
<211> LENGTH: 15
<212> TYPE: PRT
<213> ORGANISM: Artificial Sequence
<220> FEATURE:
<223> OTHER INFORMATION: CAB linker

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 360
<212> TYPE: PRT
<213> ORGANISM: Artificial Sequence
```

<220> FEATURE:
<223> OTHER INFORMATION: CAB beta-lactamase domain protein

<400> SEQUENCE: 6

```
Pro Val Ser Glu Lys Gln Leu Ala Glu Val Val Ala Asn Thr Ile Thr
  1               5                  10                  15
Pro Leu Met Lys Ala Gln Ser Val Pro Gly Met Ala Val Ala Val Ile
                 20                  25                  30
Tyr Gln Gly Lys Pro His Tyr Tyr Thr Phe Gly Lys Ala Asp Ile Ala
             35                  40                  45
Ala Asn Lys Pro Val Thr Pro Gln Thr Leu Phe Glu Leu Gly Ser Ile
 50                  55                  60
Ser Lys Thr Phe Thr Gly Val Leu Gly Gly Asp Ala Ile Ala Arg Gly
 65                  70                  75                  80
Glu Ile Ser Leu Asp Asp Ala Val Thr Arg Tyr Trp Pro Gln Leu Thr
                 85                  90                  95
Gly Lys Gln Trp Gln Gly Ile Arg Met Leu Asp Leu Ala Thr Tyr Thr
            100                 105                 110
Ala Gly Gly Leu Pro Leu Gln Val Pro Asp Glu Val Thr Asp Asn Ala
            115                 120                 125
Ser Leu Leu Arg Phe Tyr Gln Asn Trp Gln Pro Gln Trp Lys Pro Gly
130                 135                 140
Thr Thr Arg Leu Tyr Ala Asn Ala Ser Ile Gly Leu Phe Gly Ala Leu
145                 150                 155                 160
Ala Val Lys Pro Ser Gly Met Pro Tyr Glu Gln Ala Met Thr Thr Arg
                165                 170                 175
Val Leu Lys Pro Leu Lys Leu Asp His Thr Trp Ile Asn Val Pro Lys
                180                 185                 190
Ala Glu Glu Ala His Tyr Ala Trp Gly Tyr Arg Asp Gly Lys Ala Val
                195                 200                 205
Arg Val Ser Pro Gly Met Leu Asp Ala Gln Ala Tyr Gly Val Lys Thr
                210                 215                 220
Asn Val Gln Asp Met Ala Asn Trp Val Met Ala Asn Met Ala Pro Glu
225                 230                 235                 240
Asn Val Ala Asp Ala Ser Leu Lys Gln Gly Ile Ala Leu Ala Gln Ser
                245                 250                 255
Arg Tyr Trp Arg Ile Gly Ser Met Tyr Gln Gly Leu Gly Trp Glu Met
                260                 265                 270
Leu Asn Trp Pro Val Glu Ala Asn Thr Val Val Glu Thr Ser Phe Gly
                275                 280                 285
Asn Val Ala Leu Ala Pro Leu Pro Val Ala Glu Val Asn Pro Pro Ala
290                 295                 300
Pro Pro Val Lys Ala Ser Trp Val His Lys Thr Gly Ser Thr Gly Gly
305                 310                 315                 320
Phe Gly Ser Tyr Val Ala Phe Ile Pro Glu Lys Gln Ile Gly Ile Val
                325                 330                 335
Met Leu Ala Asn Thr Ser Tyr Pro Asn Pro Ala Arg Val Glu Ala Ala
                340                 345                 350
Tyr His Ile Leu Glu Ala Leu Gln
                355                 360
```

<210> SEQ ID NO 7
<211> LENGTH: 37
<212> TYPE: DNA
<213> ORGANISM: Artificial Sequence

```
<220> FEATURE:
<223> OTHER INFORMATION: synthetic oligonucleotide

<400> SEQUENCE: 7
cggccatggc ccaggtgcag ctgcagcagt ctggggc                              37

<210> SEQ ID NO 8
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 8
ctggggcaga acttgtgaaa tcagggacct cagtcaa                              37

<210> SEQ ID NO 9
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 9
gggcagaact tgtgaggccg gggacctcag tcaagtt                              37

<210> SEQ ID NO 10
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 10
aacttgtgag gtcaggggc tcagtcaagt tgtcctg                               37

<210> SEQ ID NO 11
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 11
gcacagcttc tggcttcacc attaaagact cctatat                              37

<210> SEQ ID NO 12
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 12
cagcttctgg cttcaacttt aaagactcct atatgca                              37

<210> SEQ ID NO 13
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 13
cttctggctt caacattagc gactcctata tgcactg                              37
```

```
<210> SEQ ID NO 14
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 14
actcctatat gcactgggtg aggcaggggc ctgaaca                              37

<210> SEQ ID NO 15
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 15
tgcactggtt gaggcaggcg cctgaacagg gcctgga                              37

<210> SEQ ID NO 16
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 16
ggttgaggca ggggcctggc cagggcctgg agtggat                              37

<210> SEQ ID NO 17
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 17
ccccgaagtt ccagggccgt gccactttta ctacaga                              37

<210> SEQ ID NO 18
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 18
cgaagttcca gggcaagttc acttttacta cagacac                              37

<210> SEQ ID NO 19
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 19
tccagggcaa ggccactatt actacagaca catcctc                              37

<210> SEQ ID NO 20
<211> LENGTH: 37
<212> TYPE: DNA
<213> ORGANISM: Artificial Sequence
<220> FEATURE:
<223> OTHER INFORMATION: synthetic oligonucleotide
```

<400> SEQUENCE: 20
gcaaggccac ttttactcgc gacacatcct ccaacac    37

<210> SEQ ID NO 21
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 21
ttactacaga cacatccaaa aacacagcct acctgca    37

<210> SEQ ID NO 22
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 22
ctgccgtcta ttattgtgcg gaggggactc cgactgg    37

<210> SEQ ID NO 23
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 23
ccgtctatta ttgtaatcgc gggactccga ctgggcc    37

<210> SEQ ID NO 24
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 24
ctggcggtgg cggatcacag aatgtgctca cccagtc    37

<210> SEQ ID NO 25
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 25
gcggtggcgg atcagaaagc gtgctcaccc agtctcc    37

<210> SEQ ID NO 26
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 26
gaaaatgtgc tcacccagcc gccagcaatc atgtctgc    38

<210> SEQ ID NO 27
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 27
tgctcaccca gtctccaagc atcatgtctg catctcc                              37

<210> SEQ ID NO 28
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 28
cccagtctcc agcaatcgtg tctgcatctc caggga                               37

<210> SEQ ID NO 29
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 29
tgtctgcatc tccagggcag aaggtcacca taacctg                              37

<210> SEQ ID NO 30
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 30
ctgcatctcc aggggagacc gtcaccataa cctgcag                              37

<210> SEQ ID NO 31
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 31
taagttacat gcactggtac cagcagaagc caggcac                              37

<210> SEQ ID NO 32
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 32
gcacttctcc caaactcgtg atttatagca catccaa                              37

<210> SEQ ID NO 33
<211> LENGTH: 37
<212> TYPE: DNA
<213> ORGANISM: Artificial Sequence

```
<220> FEATURE:
<223> OTHER INFORMATION: synthetic oligonucleotide

<400> SEQUENCE: 33
tggcttctgg agtccctgat cgcttcagtg gcagtgg                              37

<210> SEQ ID NO 34
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 34
ctcgcttcag tggcagtaaa tctgggacct cttactc                              37

<210> SEQ ID NO 35
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 35
gtggatctgg gacctctgcg tctctcacaa tcagccg                              37

<210> SEQ ID NO 36
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 36
ctctcacaat cagccgactg gaggctgaag atgctgc                              37

<210> SEQ ID NO 37
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 37
gaatggaggc tgaagatgaa gccacttatt actgcca                              37

<210> SEQ ID NO 38
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 38
aggctgaaga tgctgccgat tattactgcc agcaaag                              37

<210> SEQ ID NO 39
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 39
acccactcac gttcggtggc ggcaccaagc tggagct                              37
```

METHODS FOR DETECTING TARGETS

The present application claims priority under 35 U.S.C. §119, to co-pending U.S. Provisional Patent Application Ser. No. 60/609,082, filed Sep. 10, 2004, and co-pending U.S. Provisional Patent Application Ser. No. 60/609,205, filed Sep. 10, 2004.

SEQUENCE LISTING

The sequence listing submitted via EFS, in compliance with 37 C.F.R. §1.52(e), is incorporated herein by reference. The sequence listing text file submitted via EFS contains the file "30849US_SequenceListing", created on Jun. 4, 2012, which is 16,125 bytes in size.

FIELD OF THE INVENTION

The present invention provides methods and compositions for detecting target molecules present on cells and tissues. In particular, the methods involve adding primary antibodies such as scFv-targeted lactamase that are directed against a target of interest (e.g., cancer markers) to a tissue sample, followed by adding a lactam-containing compound and finally a lactamase reporter system. In some preferred embodiments, the lactamase reporters are fluorescent reporters that bind to the test tissue. In particularly preferred embodiments, the test tissue contains at least one cancer cell and/or at least one cancer-associated marker.

BACKGROUND OF THE INVENTION

Optical imaging in biomedical technology is widespread in preclinical drug development and becoming more necessary in preclinical disease models. Immunohistochemistry for research and clinical trials has long been performed with either alkaline phosphatase (AP) or horse-radish peroxidase (HRP), particularly in the areas of biomedicine and diagnostics. In some methods commonly used in both systems, a primary target-specific antibody binds to a tissue. Then, a secondary antibody conjugated with AP or HRP is added that binds to the primary antibody. Detection of the target is visualized by observing the reaction of the enzyme with a substrate that is added to the reaction mixture. In most cases, the enzyme acts on the substrate to produce a color change in the test sample due to precipitation of reaction products on the tissues. In most methods, detection is visualized with standard light microscopy techniques.

But, these systems have limitations. For example, the range of colors for distinguishing reaction products is limited, and distinguishing even two colors is sometimes problematic, while distinguishing greater than two is not currently feasible. Likewise, other than highly specialized systems, these methods are not used to generate fluorescent reaction products. Also, endogenous enzymes present in tissues (e.g., alkaline phosphatases) can lead to high backgrounds (i.e., "noise"). As a result, special blocking steps are required to prevent undesired reactions and/or prolonged staining procedures are required to kill endogenous enzymes prior to staining. Thus, improved methods for detecting tissue targets are needed.

SUMMARY OF THE INVENTION

The present invention provides methods and compositions for detecting target molecules present on cells and tissues. In particular, the methods involve adding primary antibodies such as scFv-targeted lactamase that are directed against a target of interest (e.g., cancer markers) to a tissue sample, followed by adding a lactam-containing compound and finally a lactamase reporter system. In some preferred embodiments, the lactamase reporters are fluorescent reporters that bind to the test tissue. In some particularly preferred embodiments, the test tissue contains at least one cancer cell and/or at least one cancer-associated marker.

In some embodiments, the present invention provides methods for detecting at least one target on at least one cell, comprising the steps of: providing at least one test cell having at least one target; exposing at least one test cell to a targeted agent that binds to the target, wherein the targeted agent is conjugated to an enzyme, to produce a bound target, and further wherein the enzyme is capable of cleaving a substrate to produce a detectable product; exposing the bound target to the substrate under conditions such that the enzyme cleaves the substrate to produce a product; and detecting the product. In some preferred embodiments, the at least one test cell is obtained from an animal. In some particularly preferred embodiments, the at least one test cell is a human cell. In additional embodiments, the targeted agent is selected from the group consisting of monoclonal antibodies, polyclonal antibodies, and fragments of antibodies. In some particularly preferred embodiments, the targeted agent is biotinylated. In additional preferred embodiments, the substrate is biotinylated. In yet further preferred embodiments, the at least one target comprises at least one cancer marker. In additional embodiments, the at least one cell is in vitro, in vivo, ex vivo, or in situ.

The present invention also provides methods for detecting at least one target on at least one cell, comprising the steps of: providing at least one test cell having at least one target; exposing at least one test cell to a targeted agent that binds to the target, wherein the targeted agent is conjugated to a reporter molecule, to produce a bound target; exposing the bound target to an enzyme to produce a targeted complex, wherein the enzyme is capable of cleaving a substrate to produce a detectable product; exposing the targeted complex to the substrate under conditions such that the enzyme cleaves the substrate to produce a product; and detecting the product. In some preferred embodiments, the at least one test cell is obtained from an animal. In some particularly preferred embodiments, the at least one test cell is a human cell. In additional embodiments, the targeted agent is selected from the group consisting of monoclonal antibodies, polyclonal antibodies, and fragments of antibodies. In some particularly preferred embodiments, the targeted agent is biotinylated. In additional preferred embodiments, the substrate is biotinylated. In yet further preferred embodiments, the at least one target comprises at least one cancer marker. In additional embodiments, the at least one cell is in vitro, in vivo, ex vivo, or in situ.

In some embodiments, the present invention provides methods for detecting at least one target in vivo and/or in situ, the method comprising the steps of: administering a targeted agent that binds to the target, wherein the targeted agent is conjugated to an enzyme, and wherein the enzyme is capable of cleaving a substrate to produce a product detectable in vivo and/or in situ; administering a substrate, under conditions such that the enzyme cleaves the substrate to produce a product; and detecting the product.

In some embodiments, the targeted agent is administered to a test sample. In some preferred embodiments, the test sample is a tissue sample obtained from an animal. In some particularly preferred embodiments, the tissue sample is obtained from a human.

In some embodiments, the targeted agent is administered to an organism. In some preferred embodiments, the organism is a mammal. In further preferred embodiments, the organism is a mouse, while in alternative preferred embodiments, the organism is a human.

In some preferred embodiments, the targeted agent and/or substrate is/are systemically administered to the animal. In alternative embodiments, the targeted agent and/or substrate is/are adminstered at or near the target to be bound. In some preferred embodiments, administration is accomplished by topical application, intravenous injection, intra-arterial injection, intra-peritoneal injection, subcutaneous injection or oral administration.

In some preferred embodiments, the targeted agent and the enzyme are coupled and then administered as a fusion molecule. In some preferred embodiments, the enzyme and targeted agent are coupled into a fusion molecule through standard cloning and expression methods. In some alternative embodiments, the coupling of the targeted agent and enzyme occurs via exposure to at least one chemical covalent cross-linking agent. In some preferred embodiments, the at least one chemical cross-linking agent is selected from the group consisting of thiol-thiol agents, amine-amine agents, amine-thiol agents, amine-carboxylic acid agents, thiol-carboxylic acid agents, and ether coupling agents. In some alternative preferred embodiments, coupling occurs non-covalently. In some such preferred embodiments, non-covalent coupling occurs via non-biotin-avidin/streptavidin coupling. In some preferred embodiments, coupling occurs via hydrophobic binding. In some alternative preferred embodiments, coupling occurs via ionic binding. In some preferred embodiments, coupling occurs through nucleic acid interactions, wherein the nucleic acids are modified or unmodified nucleic acids. In yet further preferred embodiments, coupling occurs through unmodified nucleic acid interactions. In some preferred embodiments, the unmodified nucleic acid interactions are RNA-DNA hybridization or DNA-DNA hybridization. In some preferred embodiments, coupling occurs through interactions with at least one modified nucleic acid. In some preferred embodiments, the at least one modified nucleic acid is selected from the group consisting of phosphothiotases, morpholino-based, and/or any other modified nucleic acid.

In some preferred embodiments, detection occurs via light detection. In some preferred embodiments, the light detection method is selected from the group consisting of fluorescence, phosphorescence, light scatter, brightfield microscopy, and/or a combination thereof. In some alternative embodiments, detection further comprises detecting differences in color and/or color intensity. In some preferred embodiments, detection occurs by optical detection systems sensitive to electromagnetic radiation in the range of about 400 nanometers to about 800 nanometers. In some preferred embodiments, detection occurs by exposure of light to photographic film, charge-coupled device (CCD) and/or photomultiplier-tube detectors. In some preferred embodiments, the photomultiplier-tube detector is specifically tuned to the spectral range of photons emitted from the product of the enzyme and substrate reaction.

In some preferred embodiments, the enzyme is capable of cleaving the lactam ring of a lactam-ring containing compound. In some particularly preferred embodiments, the enzyme cleaves the lactam ring of some commonly used antimicrobials, including penicillin, cephalosporin, and their derivatives. In some preferred embodiments, such cleavage results in elimination of the beta lactam ring, followed by the release and unquenching of a fluorophore product. In some preferred embodiments, the enzyme is a lactamase enzyme. In some particularly preferred embodiments, the enzyme is a beta-lactamase ("BLA").

The present invention provides methods in which the substrate is an organic molecule that does not fluoresce in the proximity of a second covalently attached organic molecule, and upon enzymatic release from the second molecule, the substrate becomes a product and undergoes electronic rearrangement, emitting longer wavelengths. In some preferred embodiments, the substrate is at least one of the molecules set forth in FIG. 2. In some preferred embodiments, the substrate is a β-lactam-containing compound comprising a cephem nucleus substituted at the R2 site with a fluorophore that is quenched until released by a beta-elimination reaction following hydrolytic opening of the lactam ring (See FIG. 2B; See also, Goodman and Gilman, *The Pharmacological Basis of Therapeutics*, Table 45-2, McGraw Hill [1996]).

In some preferred embodiments, the product stays relatively close to the site of cleavage. In some alternative preferred embodiment, the product does not diffuse further than about 1 to about 5 cell diameters away from the site of cleavage. In some preferred embodiments, detection occurs relatively close to the site of cleavage. In some preferred embodiments, detection occurs about 1 to about 5 cell diameters away from the site of cleavage.

In some alternative preferred embodiments, the targeted agent is selected from the group consisting of antibodies, antibody fragments, peptides, nanobodies, nanoparticles, small molecule ligands, receptor ligands, and proteins that bind targets such as cytokines or growth factors or transcription factors.

In some particularly preferred embodiments, the target is selected from the group consisting of cancerous cells, cell lines, cell cultures, tumor extracts, cancerous tissue, cancerous organs, molecules associated with a cancerous cell, molecules associated with a cell line, molecules associated with cell cultures, tumor extracts, cancerous tissues, cancerous organs, and cancerous cells, molecules associated with an organ associated with a cancerous cell, cell line or cell culture, tumor extracts or a cancerous tissue or organ.

In some preferred embodiments, the target is an antigen. In some particularly preferred embodiments, the antigen is selected from the group consisting of antibodies directed against at least one antigen selected from the group consisting of the muc-1 transmembrane glycoprotein, (oncoprotein), the pancarcinogenic antigen Tag72, carcinoembryonic antigen (CEA), the B-cell restricted sialoglycoprotein CD22, the extra domain B of fibronectin (ED-B), the transmembrane protein A33, and fibroblast activation protein (FAP).

DESCRIPTION OF THE FIGURES

FIG. 1 provides the amino acid sequence of a beta-lactamase (SEQ ID NO:2), as well as the nucleotide sequence for the nucleic acid that encodes a beta-lactamase (SEQ ID NO:1). Panel 1A provides the amino acid sequence (SEQ ID NO:2), while Panel 1B provides the nucleic acid sequence (SEQ ID NO: 1) encoding the beta-lactamase set forth in SEQ ID NO: 1. Other enzymes, and other lactamases, are intended to be within the scope of the invention, and the sequence is not intended to be limiting.

FIG. 4 shows the specificity and localization of staining in mixed human cell culture using a CAB molecule in formaldehyde-fixed cultured cells. Panel A shows a phase photomicrograph, while Panel B shows a fluorescence photomicrograph, and Panel C shows a combined phase and fluorescent photomicrograph.

FIG. 5 shows the specificity and localization of staining in mixed cell culture using CAB 1.2 in flash-frozen tissue as described in Example 4. Panel A provides a photomicrograph of substrate, while Panel B provides a photomicrograph of pan-cytokeratin, and Panel C provides a phase photomicrograph with human and mouse cells.

FIG. 13 provides sequence comparison data used in the construction of the CAB molecule. Panel 13A provides a comparison of the observed frequencies of the five most abundant amino acids in human heavy chain sequences. Panel 13B provides a comparison of the observed frequencies of the five most abundant amino acids in alignment of human light chain sequences.

DESCRIPTION OF THE INVENTION

Figure 2A:
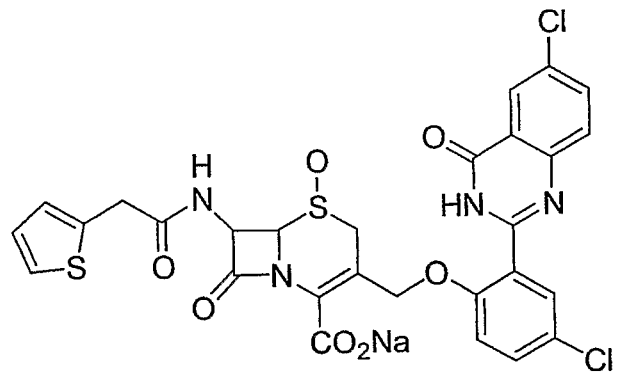
FIG. 2 provides structures of precipitating fluorogenic lactamase reporters. Panel 2A provides 7-(2-thienylaetamido)-3-(3-(6-chloro-4(3H)-quinazolinone)4-chlorophenyloxymethyl-□□-cephem-4-carboxylic acid S-oxide, while Panels 2B-2F provide the structures of additional precipitating fluorgenic lactamase reporters. These structures are not meant to be limiting, and other precipitating fluorogenic lactamase reporters find use in the present invention.

The present invention provides methods and compositions for detecting target molecules present on cells and tissues. In particular, the methods involve adding primary antibodies such as scFv-targeted lactamase that are directed against a target of interest (e.g., cancer markers) to a tissue sample, followed by adding a lactam-containing compound and finally a lactamase reporter system. In preferred embodiments, the lactamase reporters are fluorescent reporters that bind to the test tissue. In particularly preferred embodiments, the test tissue contains at least one cancer cell and/or at least one cancer-associated marker.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a," "an" and "the" includes the plural reference unless the context clearly indicates otherwise.

The term "in situ" as used herein, designates a relationship or proximity that derives from a specific association between a substance (e.g., a molecule) and intact cells. Cells can be single or multiple and can be either alive or dead. Intact cells include, but are not limited to those that are found in solution or on nonbiological surfaces (e.g., PVP membranes blots, etc.). In some preferred embodiments, the term refers to cells that are located in their natural location (e.g., within an organ or tissue).

The term "ex vivo" as used herein, refers to cells within a tissue, but not within an intact organism. Thus, in preferred embodiments, the term is used to indicate cells and/or tissues that are outside of the living body. In some embodiments, the cells/tissue are not processed for preservation. Typically, ex-vivo refers to live cells and/or tissues. Examples include, but are not limited to whole blood, liver, kidney and heart. In some embodiments, the term is used to refer to organs that have been removed from the body, but are later returned to the body.

The term "in vivo" as used herein, refers to cells, tissues, etc., within a living body (e.g., an intact organism). In vivo cells or tissues are contrasted with those no longer in an organism, such as those growing in tissue culture containers or in fixed and mounted tissues (e.g., cells in IHC and TMAs, as set forth herein).

The term "in vitro" as used herein, refers to cells, tissues, etc. that are outside of the living body. The term more particularly refers to an artificial environment, such as that within test tubes, growth flasks, etc.

As used herein, "beta-lactamase" refers to any enzyme that breaks down beta lactam rings (i.e., a heteroatomic ring structure comprising three carbon atoms and one nitrogen atom). Beta lactam rings are components of several antimicrobials, including but not limited to penicillin, cephalosporin, and other related compounds. In some preferred embodiments, the beta-lactamase of the present invention is native enzyme, while in some other preferred embodiments, the beta-lactamase of the present invention is recombinant. In some additionally preferred embodiments, the beta-lactamases of the present invention are modified, such that the beta-lactamases stimulate a lower immunogenic reaction than native beta-lactamases.

As used herein, the term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

As used herein, "recombinant beta-lactamase" refers to an beta-lactamase in which the DNA sequence encoding beta-lactamase is modified to produce a variant (or mutant) DNA sequence which encodes the substitution, deletion or insertion of one or more amino acids in the naturally-occurring amino acid sequence. Suitable methods to produce such modification are well-known to those in the art.

The term "recombinant DNA molecule" as used herein refers to a DNA molecule that is comprised of segments of DNA joined together by means of molecular biological techniques.

As used herein, the term "enzymatic conversion" refers to the modification of a carbon substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring (i.e., precursor) protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "sample" as used herein, is used in its broadest sense. However, in preferred embodiments, the term is used in reference to a sample (e.g., an aliquot) that comprises a target of interest that is being analyzed, identified, modified, and/or compared with other targets. Thus, in most cases, this term is used in reference to material that includes a protein or peptide that is of interest.

As used herein, the terms "purified" and "isolated" refer to the removal of contaminants from a sample. For example, beta-lactamases are purified by removal of contaminating proteins and other compounds within a solution or preparation that are not beta-lactamases. In some embodiments, recombinant beta-lactamases are expressed in bacterial host cells and these recombinant beta-lactamases are purified by the removal of other host cell constituents; the percent of recombinant beta-lactamase polypeptides is thereby increased in the sample.

The term "gene" as used herein, refers to a molecule comprised of two or more deoxyribonucleotides or ribonucleotides. The exact size will depend upon many factors, which in turn, depend on the ultimate function or use of the oligonucleotide. Genes can be prepared by any suitable method, including, for example, cloning of appropriate sequences and direct chemical synthesis by any suitable method known in the art (See e.g., Goodchild, Bioconjugate Chem., 1:165-187 [1990]), including but not limited to the phosphotriester method (See e.g., Narang et al., Meth. Enzymol., 68:90-99 [1979]), the phosphodiester method of (See e.g., Brown et al., Meth. Enzymol., 68:109-151 [1979]), the diethylphosphoramidite method (See e.g., Beaucage et al, Tetrahedron Lett., 22:1859-1862 [1981]); and the solid support method (See e.g., U.S. Pat. No. 4,458,066, incorporated herein by reference).

The term "fusion gene" as used herein, designates a gene construct that results when any one gene is fused to another or any two sequences encoding protein domains are fused to one another. All known fusion methods are intended to be within the scope of the invention.

The term "protein" is used interchangeably here, as well as in the art, with the terms "peptide" and "polypeptide," and refers to a molecule comprising two or more amino acid residues joined by a peptide bond.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine). Standard three-letter or one-letter amino acid abbreviations may be used herein, as well as in the art. One skilled in the art may make equivalent substitutions (e.g., an aromatic substituted for an aromatic) and such equivalent substitutions are intended to be within the scope of the claims, where appropriate.

The peptides, polypeptides and proteins of the invention can also comprise one or more non-classical amino acids. Non-classical amino acids include, but are not limited to, the D-isomers of the common amino acids, α-amino isoburyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornitbine, norleucine, norvaline, hydroxyproline, sarcosine, citrulline, cysteic acid, t-butylglycine, t-burylalanine, phenylglycine, cyclohexylalanine, β-alanine, fluoro-amino acids and designer amino acids such as β-methyl amino acids, Cα-methyl amino acids and Nα-methyl amino acids.

The term "fusion protein" is used herein to designate a protein that results when any protein is fused to another. In some embodiments, fusion proteins result when one gene is fused to another to encode a "fusion protein," and then the resulting fusion gene is expressed and produces a fusion protein. Various fusion methods are known to those of skill in the art and find use in the present invention.

The term "binder," as used herein, refers to a molecule that has been determined to bind to a target, as described herein. Verification of binding is accomplished through any suitable means known in the art. In some embodiments, the binding is assessed qualitatively assessed, while in other embodiments the binding is quantitatively assessed. In addition, the present invention provides for a range of all binding affinities, as the scope of the invention depends upon the purpose of the contemplated assays.

As used herein, the term "targeted complex" refers to a target that has been bound by a targeted agent and an enzyme. For example, in some particularly preferred embodiments, the "targeted agent" is an antibody and/or antibody fragment conjugated to a reporter molecule that has bound to a target (i.e., to form a "bound target"). This bound target is then bound to an enzyme to produce a "targeted complex." In some particularly preferred embodiments, the enzyme is bound to the bound target via the interaction between biotin and avidin or streptavidin.

The terms "specific binding" or specifically binding" when used in reference to the interaction of an antibody and a protein or peptide means that the interaction is dependent upon the presence of a particular structure (i.e., the antigenic determinant or epitope) on the protein. In other words, the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "tissue" refers to a group or layer of similarly specialized cells which together perform certain specialized functions. In some tissues, cells of only one type are present, while in other tissues, cells of different types are present. The term includes but is not limited to lymphoid, lymphadenoid, adipose, bony, aerolar, cartilaginous, connective, elastic, endothelial, epithelial, fibrous, glandular, gut-associated lymphoid (GALT), indiffernt, interstitial, reticular, mesenchymal, myeloid, muscular, nervous, osseous, skeletal, subcutaneous, and other tissue types.

As used herein, the term "organ" refers to any somewhat independent body part that performs a specialized function. The term includes, but is not limited to the heart, kidneys, liver, spleen, skin, stomach, large intestine, small intestine, pancreas, eyes, brain, tongue, lungs, reproductive organs, etc.

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any suitable expression vector. Additionally, transformation refers to cells that have been transformed naturally, usually through genetic mutation.

The terms "transformants" and "transformed cells" encompass the primary transformed cell (prokaryotic or eukaryotic) and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, "antigen" refers to a molecule that is recognized by and bound by an antibody. In some embodiments, antigens are also immunogens (i.e., an immune response is The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody. Examples of "antigens of interest," include cancer antigens, particularly those whose overexpression is correlated with a specific pathology (e.g., a specific indication of cancer).

"Antibody" (Ab) and "immunoglobulin" (Ig) as used herein, refer to defined as a glycoprotein produced by B cells and plasma cells of humans and other animals, that binds with high specificity to an antigen (usually, but not always, a peptide) or a structurally similar antigen, that generated its production. Antibodies may be produced by any of the known methodologies and may be either polyclonal or monoclonal. The term also encompasses chimeric antibodies, humanized antibodies, immunoglobulins or antibody or functional fragments of an antibody that bind to an antigen. Examples of such functional entities include complete antibody molecules, antibody fragments, such as Fv, single chain Fv, complementarity determining regions (CDRs), $V_L$ (light chain variable region), $V_H$ (heavy chain variable region) and any combination of those or any other functional portion of an immunoglobulin peptide capable of binding to target antigen.

The antibodies used in the present invention may be prepared using various immunogens.

Various procedures known in the art may be used for the production of polyclonal antibodies. In some embodiments for the production of antibody, various host animals (including but not limited to rabbits, mice, rats, sheep, goats, etc.) are immunized by injection with the peptide corresponding to a target of interest in the present invention. In one preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response; depending on the host species, including but not limited to Freund's (complete and incomplete), mineral gels such as aluminum hydroxide, surface active substances such as lysolecitbin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See, e.g., Harlow and Lane, *Antibodies: A Laboratory Manual*. Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al. Immunol. Today 4:72 [1983]), and the EBV-hybridoma technique to produce human monoclonal antibodies (See e.g., Cole et al., in *Monoclonal Antibodies and Cancer Therapy*, Alan R. Liss, Inc., pp. 77-96 [1985]). In some particularly preferred embodiments of the present invention, the present invention provides monoclonal antibodies of the IgG class.

In an additional embodiment of the invention, monoclonal antibodies are produced in germ-free animals (See e.g., PCT/US90/02545). According to the invention, human antibodies find use and can be obtained by using human hybridomas (See e.g., Cote et al., Proc. Natl. Acad. Sci. U.S.A. 80:2026-2030 [1983]) or by transforming human B cells with EBV virus in vitro (See e.g., Cole et al. in *Monoclonal Antibodies and Cancer Therapy*, Alan R. Liss, pp. 77-96 [1985]).

According to the invention, techniques described for the production of single chain antibodies (U.S. Pat. No. 4,946,778; herein incorporated by reference) can be adapted to produce single chain antibodies that specifically recognize a molecule of interest. In some embodiments, the techniques described for the construction of Fab expression libraries (See e.g., Huse et al., Science 246:1275-1281 [1989]) are used to allow rapid and easy identification of monoclonal Fab fragments with the desired specificity.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [using colloidal gold, enzyme or radioisotope labels, for example], Western Blots, precipitation reactions, agglutination assays (e.g., gel agglutination assays, hemagglutination assays, etc.), complement fixation assays, immunofluorescence assays, protein A assays, and Immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

"Staining," as used herein, refers to any number of processes known to those in the field that are used to better visualize a specific component(s) and/or feature(s) of a cell or cells.

The term "target" as used herein, refers to a substance of interest. In some preferred embodiments, targets are identified by exposing samples to fusion proteins of the present invention. In some embodiments, the target is a cancerous cell, cell line or cell culture, tumor extract, cancerous tissue or organ, or any molecule associated with a cancerous cell, cell line or cell culture, tumor extract, or a cancerous tissue or organ. In some embodiments, antigens are targets.

The term "tumor extract" as used herein, refers to a sample obtained from a cancerous cell, cell line or cell culture or a cancerous tissue or organ.

The term "coupling" as used herein, refers to the process of covalent and/or non-covalent interactions between two moieties. In preferred embodiments, the moieties coupled are targeting and catalytic moieties. Coupling can be accomplished through any suitable means, including but not limited to the use of standard cloning and expression methods, chemical covalent cross-linking agents such as thiol-thiol agents, amine-amine agents, amine-thiol agents, amine-carboxylic acid agents, thiol-carboxylic acid agents, ether coupling agents, non-covalent means such as through non-biotin-avidin/streptavidin coupling, hydrophobic binding, ionic binding, and/or through nucleic acid interactions wherein the nucleic acids are modified or unmodified nucleic acids.

The term "adherent" as used herein, refers the sticking of reaction products and other compounds (e.g., precipitates), to cell and/or other surfaces. This sticking may be accomplished by any means, including but not limited to hydrophobic interaction with cell surfaces or differential solubilities, such that the product sticks to cell surface, diffuses or is actively transported into cells.

DETAILED DESCRIPTION OF THE INVENTION

The present invention provides methods and compositions for detecting target molecules present on cells and tissues. In particular, the methods involve adding primary antibodies such as scFv-targeted lactamase that are directed against a target of interest (e.g., cancer markers) to a tissue sample, followed by adding a lactam-containing compound and finally a lactamase reporter system. In preferred embodiments, the lactamase reporters are fluorescent reporters that bind to the test tissue. In particularly preferred embodiments, the test tissue contains at least one cancer cell and/or at least one cancer-associated marker.

The present invention overcomes problems associated with currently used standard immunohistochemical methods that rely upon HRP and/or AP. The basic method involves the binding of a primary antibody, followed by binding of any targeted lactamase enzyme followed by addition of specific fluorescent lactamase reporters that are colorless and non-fluorescent until lactamase cleaves the molecule, releasing a precipitating, highly stable fluorophore that adheres tightly to the target. In principle, lactamase can be conjugated to any targeting entity including antibodies, peptides, receptor ligands, scFv's and nanobodies. All that is required is a targeting moiety. The reaction is extremely simple and fast to run and blocking is not required. Because lactamase is not a mammalian enzyme, there are no background issues due to endogenous enzyme activity. Additionally, the precipitating substrate has proved not only to be simple and fast to use, but highly specific (i.e., the "wrong" cells-those that do not express an antigen of interest, are not labeled). In addition, the reagent is well-suited to immunohistochemical procedures with cells, tissues, cryosections, paraffin-embedded tissue, and tissue arrays (cryosections or paraffin embedded).

In some embodiments, the present invention provides methods for detecting at least one target on at least one cell, comprising the steps of: providing at least one test cell having at least one target; exposing at least one test cell to a targeted agent that binds to the target, wherein the targeted agent is conjugated to an enzyme, to produce a bound target, and further wherein the enzyme is capable of cleaving a substrate to produce a detectable product; exposing the bound target to the substrate under conditions such that the enzyme cleaves the substrate to produce a product; and detecting the product. In some preferred embodiments, the at least one test cell is obtained from an animal. In some particularly preferred embodiments, the at least one test cell is a human cell. In additional embodiments, the targeted agent is selected from the group consisting of monoclonal antibodies, polyclonal antibodies, and fragments of antibodies. In some particularly preferred embodiments, the targeted agent is biotinylated. In additional preferred embodiments, the substrate is biotinylated. In yet further preferred embodiments, the at least one target comprises at least one cancer marker. In additional embodiments, the at least one cell is in vitro, in vivo, ex vivo, or in situ.

The present invention also provides methods for detecting at least one target on at least one cell, comprising the steps of: providing at least one test cell having at least one target; exposing at least one test cell to a targeted agent that binds to the target, wherein the targeted agent is conjugated to a reporter molecule, to produce a bound target; exposing the bound target to an enzyme to produce a targeted complex, wherein the enzyme is capable of cleaving a substrate to produce a detectable product; exposing the targeted complex to the substrate under conditions such that the enzyme cleaves the substrate to produce a product; and detecting the product. In some preferred embodiments, the at least one test cell is obtained from an animal. In some particularly preferred embodiments, the at least one test cell is a human cell. In additional embodiments, the targeted agent is selected from the group consisting of monoclonal antibodies, polyclonal antibodies, and fragments of antibodies. In some particularly preferred embodiments, the targeted agent is biotinylated. In additional preferred embodiments, the substrate is biotinylated. In yet further preferred embodiments, the at least one target comprises at least one cancer marker. In additional embodiments, the at least one cell is in vitro, in vivo, ex vivo, or in situ.

In some embodiments, the present invention provides methods for detecting at least one target in vivo and/or in situ, the method comprising the steps of: administering a targeted agent that binds to the target, wherein the targeted agent is conjugated to an enzyme, and wherein the enzyme is capable of cleaving a substrate to produce a product detectable in vivo and/or in situ; administering a substrate, under conditions such that the enzyme cleaves the substrate to produce a product; and detecting the product.

In some embodiments, the targeted agent is administered to a test sample. In some preferred embodiments, the test sample is a tissue sample obtained from an animal. In some particularly preferred embodiments, the tissue sample is obtained from a human.

In some embodiments, the targeted agent is administered to an organism. In some preferred embodiments, the organism is a mammal. In further preferred embodiments, the organism is a mouse, while in alternative preferred embodiments, the organism is a human.

In some preferred embodiments, the targeted agent and/or substrate is/are systemically administered to the animal. In alternative embodiments, the targeted agent and/or substrate is/are administered at or near the target to be bound. In some preferred embodiments, administration is accomplished by topical application, intravenous injection, intra-arterial injection, intra-peritoneal injection, subcutaneous injection or oral administration.

In some preferred embodiments, the targeted agent and the enzyme are coupled and then administered as a fusion molecule. In some preferred embodiments, the enzyme and targeted agent are coupled into a fusion molecule through standard cloning and expression methods. In some alternative embodiments, the coupling of the targeted agent and enzyme occurs via exposure to at least one chemical covalent cross-linking agent. In some preferred embodiments, the at least one chemical cross-linking agent is selected from the group consisting of thiol-thiol agents, amine-amine agents, amine-thiol agents, amine-carboxylic acid agents, thiol-carboxylic acid agents, and ether coupling agents. In some alternative preferred embodiments, coupling occurs non-covalently. In some such preferred embodiments, non-covalent coupling occurs via non-biotin-avidin/streptavidin coupling. In some preferred embodiments, coupling occurs via hydrophobic binding. In some alternative preferred embodiments, coupling occurs via ionic binding. In some preferred embodiments, coupling occurs through nucleic acid interactions, wherein the nucleic acids are modified or unmodified nucleic acids. In yet further preferred embodiments, coupling occurs through unmodified nucleic acid interactions. In some preferred embodiments, the unmodified nucleic acid interactions are RNA-DNA hybridization or DNA-DNA hybridization. In some preferred embodiments, coupling occurs through interactions with at least one modified nucleic acid. In some preferred embodiments, the at least one modified nucleic acid is selected from the group consisting of phosphothiotases, morpholino-based, and/or any other modified nucleic acid.

In some preferred embodiments, detection occurs via light detection. In some preferred embodiments, the light detection method is selected from the group consisting of fluorescence, phosphorescence, light scatter, brightfield microscopy, and/or a combination thereof. In some alternative embodiments, detection further comprises detecting differences in color and/or color intensity. In some preferred embodiments, detection occurs by optical detection systems sensitive to electromagnetic radiation in the range of about 400 nanometers to about 800 nanometers. In some preferred embodiments, detection occurs by exposure of light to photographic film, charge-coupled device (CCD) and/or photomultiplier-tube detectors. In some preferred embodiments, the photomultiplier-tube detector is specifically tuned to the spectral range of photons emitted from the product of the enzyme and substrate reaction.

In some preferred embodiments, the enzyme is capable of cleaving the lactam ring of a lactam-ring containing compound. In some particularly preferred embodiments, the enzyme cleaves the lactam ring of some commonly used antimicrobials, including penicillin, cephalosporin, and their derivatives. In some preferred embodiments, such cleavage results in elimination of the beta lactam ring, followed by the release and unquenching of a fluorophore product. In some preferred embodiments, the enzyme is a lactamase enzyme. In some particularly preferred embodiments, the enzyme is a beta-lactamase ("BLA").

The present invention provides methods in which the substrate is an organic molecule that does not fluoresce in the proximity of a second covalently attached organic molecule, and upon enzymatic release from the second molecule, the substrate becomes a product and undergoes electronic rearrangement, emitting longer wavelengths. In some preferred embodiments, the substrate is at least one of the molecules set forth in FIG. 2. In some preferred embodiments, the substrate is a β-lactam-containing compound comprising a cephem nucleus substituted at the R2 site with a fluorophore that is quenched until released by a beta-elimination reaction following hydrolytic opening of the lactam ring (See FIG. 2B; See also, Goodman and Gilman, *The Pharmacological Basis of Therapeutics*, Table 45-2, McGraw Hill [1996]).

In some preferred embodiments, the product stays relatively close to the site of cleavage. In some alternative preferred embodiment, the product does not diffuse further than about 1 to about 5 cell diameters away from the site of cleavage. In some preferred embodiments, detection occurs relatively close to the site of cleavage. In some preferred embodiments, detection occurs about 1 to about 5 cell diameters away from the site of cleavage.

In some alternative preferred embodiments, the targeted agent is selected from the group consisting of antibodies, antibody fragments, peptides, nanobodies, nanoparticles, small molecule ligands, receptor ligands, and proteins that bind targets such as cytokines or growth factors or transcription factors.

In some particularly preferred embodiments, the target is selected from the group consisting of cancerous cells, cell lines, cell cultures, tumor extracts, cancerous tissue, cancerous organs, molecules associated with a cancerous cell, molecules associated with a cell line, molecules associated with cell cultures, tumor extracts, cancerous tissues, cancerous organs, and cancerous cells, molecules associated with an organ associated with a cancerous cell, cell line or cell culture, tumor extracts or a cancerous tissue or organ.

In some preferred embodiments, the target is an antigen. In some particularly preferred embodiments, the antigen is selected from the group consisting of antibodies directed against at least one antigen selected from the group consisting of the muc-1 transmembrane glycoprotein, (oncoprotein), the pancarcinogenic antigen Tag72, carcinoembryonic antigen (CEA), the B-cell restricted sialoglycoprotein CD22, the extra domain B of fibronectin (ED-B), the transmembrane protein A33, and fibroblast activation protein (FAP).

In some embodiments involving administration of a targeted agent and/or substrate, various routes of administration find use, including but not limited to parenteral (e.g., intravenous), intradermal, intraperitonal, subcutaneous, oral, nasal (i.e., inhalation), topical, transdermal, transmucosal and rectal administration. In some embodiments, solutions or suspensions used for various routes of administration include, but are not limited to components such as a sterile diluent (e.g., water, saline solution, fixed oils, polyethylene glycols, glycerine, propylene glycol, and/or other synthetic solvents); antibacterial agents (e.g., benzyl alcohol and/or methyl parabens); antioxidants (e.g., ascorbic acid and/or sodium bisulfite); chelating agents (e.g., ethylenediaminetetraacetic acid); buffers (e.g., acetates, citrates and/or phosphates), as well as agents for the adjustment of tonicity (e.g., sodium chloride and/or dextrose). As needed, the pH can be adjusted with acids or bases, such as hydrochloric acid or sodium hydroxide. In some embodiments, the preparation are enclosed within ampoules, disposable syringes and/or multiple dose vials (e.g., glass or plastic vials).

Compositions suitable for injectable use include sterile aqueous solutions (where water soluble) or dispersions and sterile powders for the extemporaneous preparation of sterile injectable solutions or dispersions. For intravenous administration, suitable carriers include, but are not limited to physiological saline, bacteriostatic water, Cremophor EL™ (BASF; Parsippany, N.J.), and/or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyetheylene glycol, and the like) and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it is preferable to include isotonic agents, for example, sugars, polyalcohols such as mannitol, sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the other ingredients required. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral administration, the active compound can be incorporated with excipients and used in the form of tablets, troches or capsules. Oral compositions can also be prepared using a fluid carrier for use as a mouthwash, wherein the compound in the fluid carrier is applied orally and swallowed or swished and expectorated.

Compatible binding agents, and/or adjuvant materials can be included as part of the composition. The tablets, pills, capsules, troches and the like can contain any of the following ingredients, or compounds of a similar nature: a binder such as macrocrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the targeted agent and/or substrate are delivered in the form of an aerosol spray from a pressurized container or dispenser that contains a suitable propellant (e.g., a gas such as carbon dioxide or a nebulizer).

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art.

The compounds can also be prepared in the form of suppositories (e.g., with conventional suppository bases such as cocoa butter and other glycerides) or retention enemas for rectal delivery.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the organism; each unit containing a predetermined quantity of active compound, calculated to produce the desired effect in association with the required carrier. The specification for the dosage unit forms are dictated by and directly dependent on the unique characteristics of the active compound and the particular therapeutic effect to be achieved and the limitations inherent in the art of compounding such an active compound for the treatment of organisms.

Typically, the amount delivered to an organism will depend on a number of factors, including, for example, the route of administration, the activity of the molecules, the degree to which it is specifically targeted to the desired cells, tissues or organs of the organism, the length of time required to clear the non-specifically bound molecules from the organism, the body mass of the organism, other medications or treatments being administered to the organism or subject, the severity of any extant disease and a previous or future anticipated course of treatment.

In a preferred embodiment, the targeted agent and the enzyme are coupled providing a fusion molecule, hi a preferred embodiment, coupling occurs either through standard cloning and expression methods or coupling occurs through chemical covalent cross-linking agents (See e.g., Sambrook et al. *Molecular Cloning Methods*, Cold Spring Harbor Laboratory, [1989], for general cloning methods); enzyme-based fusion proteins (See e.g., Bosslet et al., Br. J. Cancer 65:234-238 [1992]; Goshorn et al., Cancer Res., 53:2123-2127 [1993]; Senter et al., Bioconjugate Chem., 4:3-9 [1993]; DeSutter et al., Mol. Immunol., 31:261-267 [1994]; Rodrigues et al., Cancer Res., 55:63-70 [1995]; Svensson et al., Cancer Res., 55:2357-2365 [1995]; Kerr et al., Cancer Res., 55:3558-3563 [1995]; and Siemers et al., Bioconjugate Chem., 8:510-519 [1997]).

In some preferred embodiments, the agents are at least one selected from the group consisting of thiol-thiol agents, amine-amine agents, amine-thiol agents, amine-carboxylic acid agents, thiol-carboxylic acid agents and ether coupling agents. In some preferred embodiments, coupling occurs non-covatently. In other preferred embodiments, non-covalent coupling occurs through non-biotinravidin/streptavidin coupling. In additional preferred embodiments, coupling occurs hydrophobically. In further preferred embodiments, coupling occurs ionically. In yet more preferred embodiments, coupling occurs though nucleic acid interactions, wherein the nucleic acids are modified or unmodified nucleic acids. In some preferred embodiments, coupling occurs through unmodified nucleic acid interactions. In further preferred embodiments, the unmodified nucleic acid interactions are RNA-DNA hybridization or DNA-DNA hybridization. In additional preferred embodiments, coupling occurs via triplex interactions with double-stranded nucleic acids (See e.g., Giovannangeli et al., Curr. Opin. Mol. Ther., 2:288-96 [2000]; Vasquez et al., Trends Biochem Sci., 23:4-9 [1988]). In some preferred embodiments, coupling also occurs through modified nucleic acid interactions. In other preferred embodiments, the modified nucleic acids may be PNAs (peptide nucleic acids) in which the sugar-phosphodiester backbone is replaced with a peptide backbone (See, Nielsen et al Curr. Med. Chem., 8:545-50 [2001]); phosphorothioates or phosphorodithioates or methylphosphonates, in which the phosphate of the nucleic acid backbone has been modified (Matteucchi, Ciba Found Symp., 209:5-14 [1997]; morpholino-based nucleic acids, in which the sugar-phosphodiester backbone has been replaced by morphilino moieties (See, Summerton, Antisense Nucl. Acid Drug Dev., 7:63-70 [1997]; locked nucleic acids, in which the sugar of the backbone is "locked" into a more rigid conformation to increase binding affinity or any other modified nucleic acids (See, Stein et al., Antisense Nucl. Acid Drug Dev., 7:151-7 [1997]). In some preferred embodiments, the modified nucleic acids may be aptamers (nucleic acid or peptide-based molecules that recognize other molecules or targets) (Burgstaller et al. Curr. Opin. Drug Discov. Devel., 5:690-700 [2002]; and Crawford et al., Brief Funct. Genomic Proteomic, 2:72-9 [2003]).

In some preferred embodiments, detection occurs via light detection. In alternative preferred embodiments, light detection is selected from the group consisting of detecting fluorescence, phosphorescence, light scatter or combinations thereof with or without also detecting differences in color or color intensity. In further preferred embodiments, detection occurs by optical detection systems sensitive to electromagnetic radiation in the range of about 400 nanometers to about 800 nanometers. In some preferred embodiments, detection occurs by exposure of light to photographic film, CCD or photomultiplier-tube detectors. In additional preferred embodiments, a photomultiplier-tube detector is specifically tuned to the spectral range of photons emitted from the products embodiment.

In some preferred embodiments, the enzyme is one capable of cleaving the lactam ring of penicillin, ampicillin, cephalosporin, and/or any other lactam-ring containing molecule, leading to beta-elimination and release and unquenching of a fluorophore product. In some particularly preferred embodiments, the enzyme is lactamase.

In a preferred embodiment, the enzyme is a beta-lactamase ("BLA"). BLA enzymes are widely distributed in both Gram-negative and Gram-positive bacteria. BLA enzymes vary in their exact specificity, but all hydrolyze β-lactams, producing substituted β-amino acids. Thus, they confer resistance to antibiotics containing β-lactams. Because BLA enzymes are not endogenous to mammals, unlike many proteases, they are usually only minimally subject to interference from inhibitors, enzyme substrates, and/or endogenous enzyme systems. Thus, BLAs are particularly well suited for reporter functions.

Examples of specific BLAs that find use in the present invention include, but are not limited to, Class A, B, C and/or D β-lactamase, β-galactosidase, (See e.g., Benito et al., FEMS Microbiol. Lett., 123:107 [1994]), fibronectin, glucose oxidase, glutathione S-transferase (See e.g., Napolitano et al., Chem. Biol. 3:359 [1996]) and tissue plasminogen activator (See e.g., Smith et al, J. Biol. Chem. 270:30486 [1995]).

Following binding of the targeting-enzyme coupled moiety in vivo, a quenched fluorescent cleavable substrate is administered (e.g., parenterally) and allowed to reach the site(s) of binding of the targeting moiety upon which time the quenched fluorescence substrate is cleaved generating an "adherent" or localized, photon-emitting optically-detectable product.

In some preferred embodiments, the substrate is an organic molecule of electronic structure that does not fluoresce in the proximity of a second covalently attached organic molecule.

Upon enzymatic release from the second molecule, the substrate is converted into a product by the enzyme, undergoes electronic rearrangement, emitting wavelengths that are longer. In some preferred embodiments, the substrate is at least one of the molecules set forth in FIG. 2. In some preferred embodiments, the substrate is a β-lactam-containing compound (e.g., an antimicrobial) comprising a cephem nucleus substituted at the R2 site with a fluorophore that is quenched until released by a beta-elimination reaction following hydrolytic opening of the lactam ring (See FIG. 2C; See also, Goodman and Gilman, *The Pharmacological Basis of Therapeutics*, McGraw-Hill, [1996], Table 45-2, which is incorporated by reference herein, including any drawings).

The fluorescent component of the antimicrobial (e.g., cephalosporin) conjugate comprises any fluorophore such that when it is coupled to cephalosporin it is quenched, but is unquenched when it is released from the antimicrobial and becomes localized to the site of the enzyme by mechanisms such as: (1) precipitation and adherence to the cell surface to which the enzyme is bound by the targeting moiety; (2) hydrophobic attraction (for example through an aliphatic carbon chain) that will bind to the lipids present in the cell membrane without being internalized; (3) being of a nature such that it diffuses through the plasma membrane and hence is internalized within the cell; and/or (4) being a molecule that facilitates active uptake, such as an amino acid transporter.

As lactamase substrates can exhibit different spectral properties, this system provides additional flexibility in terms of providing the means to utilize many colors. Because lactamase is an enzyme, substantial signal amplification is also an important property of this system, which also contributes to its uniqueness.

In some preferred embodiments, the product is an adherent molecule. In other preferred embodiments, the product stays relatively close to the site of cleavage. In some preferred embodiments, the product does not diffuse further than about 1 to about 5 cell diameters away from the site of cleavage. In additional preferred embodiments, detection occurs relatively close to the site of cleavage. In further preferred embodiments, detection occurs about 1 to about 5 cell diameters away from the site of cleavage.

In some preferred embodiments, the targeted agent is selected from the group consisting of antibodies or fragments thereof, peptides, nanobodies, nanoparticles, small molecule ligands, receptor ligands, proteins found to bind targets (e.g., cytokines or growth factors) and/or transcription factors.

In some preferred embodiments, the target is selected from the group consisting of a cancerous cell, cell line or cell culture; tumor extracts or a cancerous tissue or organ; a molecule associated with a cancerous cell, cell line or cell culture tumor extracts or a cancerous tissue or organ; or a cell, cell line or cell culture, tissue or organ associated with a cancerous cell; cell line or cell culture, tumor extracts or a cancerous tissue or organ.

In some embodiments, the target is a surface. In some embodiments, the surface is a "biological surface." In additional embodiments, the biological surface is a surface of an organ, while in alternative embodiments, the biological surface is the surface of a cell or a tissue. In some further embodiments, the biological surface is a surface of a diseased organ, tissue or cell, while in some alternative embodiments, the biological surface is a surface of a normal or healthy organ, tissue or cell. In yet further embodiments, the surface is a macromolecule in the interstitial space of a tissue. In additional embodiments, the biological surface is the surface of a microorganism, including but not limited to bacteria, fungi, viruses, parasites (helminths, protozoans, etc.). In some embodiments, the microorganism is an animal pathogen, while in other embodiments, the microorganism is non-pathogenic for humans and/or other animals. Sources of cells and/or tissues include humans, non-human animals, bacteria, fungi, and plants.

In some preferred embodiments, the target is a "cancer-related target." The term includes any target that a composition of the invention binds to as part of the diagnosis or detection of a cancer or cancer-associated condition in an organism. For example, the term includes cancerous cells, tissues and/or organs; molecules associated with cancerous cells, tissues or organs; and/or molecules, cells, tissues or organs that are associated with cancerous cells, tissues or organs (e.g., a tumor-bound diagnostic molecule administered to a subject) as well as biopsy samples taken from a subject, or a healthy tissue (e.g., vasculature that is associated with cancerous tissue). Examples of cancer-related targets are provided in U.S. Pat. No. 6,261,535, which is incorporated herein by reference in its entirety. However, it is not intended that the present invention be limited to any specific cancer-related targets. The cancer-related target can be related to any cancer or cancer-associated condition. Examples of types of cancers include, but are not limited to carcinomas, sarcomas, myelomas, leukemias, lymphomas, and mixed type cancers.

In some embodiments, the cancer is a bone cancer. Examples include, but are not limited to Ewing's sarcoma, osteosarcoma, rhabdomyosarcoma and other soft-tissue sarcomas. In other embodiments, the cancer is a neurological cancer, including but not limited to brain tumors, oligodendrogliomas, ependymomas, menengiomas, lymphomas, schwannomas, and medulloblastomas. In additional embodiments, the cancer is breast cancer (e.g., ductal carcinoma in situ in the breast). In further embodiments, the cancer is prostate cancer. In still further embodiments, the cancer is an endocrine system cancer (e.g., adrenal, pancreatic, parathyroid, pituitary and thyroid). In additional embodiments, the cancer is a gastrointestinal cancer, (e.g., anal, colorectal, rectal, oral, linguinal, esophageal, stomach, gall bladder, gastric, liver, pancreatic, large intestine, and small intestine cancers). In further embodiments, the cancer is a gynecological cancer (e.g., cervical, endometrial, uterine, fallopian, gestational trophoblastic disease, choriocarcinoma, ovarian, vaginal and vulvar). In still further embodiments, the cancer is a head and neck cancer (e.g., laryngeal, oropharyngeal, parathyroid and thyroid cancer). In additional embodiments, the cancer is a leukemic cancer (e.g., acute lymphocytic leukemia, acute myelogenous leukemia, chronic lymphocytic leukemia, chronic myelogenous leukemia, hairy cell leukemia and/or a myeloproliferative disorder). In still further embodiments, the cancer is a lung cancer (e.g., mesothelioma, non-small cell lung cancer, and small cell lung cancer). In additional embodiments, the cancer is a lymphoma (e.g., AIDS-related lymphoma, cutaneous T-cell lymphoma, B-cell lymphoma, mycosis fungoides, Hodgkin's disease and non-Hodgkin's disease). In other embodiments, the cancer is a myeloma (e.g., multiple myeloma). In still other embodiments, the cancer is a pediatric cancer (e.g., brain tumor, Ewing's sarcoma, leukemia (e.g., acute lymphocytic leukemia or acute myelogenous leukemia), liver cancer, a lymphoma (e.g., Hodgkin's lymphoma or non-Hodgkin's lymphoma), neuroblastoma, retinoblastoma, sarcoma (e.g., osteosarcoma or rhabdomyosarcoma), and Wilms' Tumor. In still further embodiments, the cancer is a male reproductive cancer, including but not limited to prostate, testicular, epididymal, and penile cancer. In additional embodiments, the cancer is a skin cancer (e.g., cutaneous T cell lymphoma, mycosis fungoides, Kaposi's sarcoma, subcutaneous, or melanoma). In further embodiments, the cancer is thyroid cancer (e.g., papillary, follicular, medullary or anaplastic or undifferentiated thyroid carcinoma). In additional embodiments, the cancer is urinary tract cancers (e.g., bladder, kidney and urethral). In further embodiments, the cancer or cancer-related condition is ataxia-telangiectasia, carcinoma of unknown primary origin, Li-Fraumeni syndrome or thymoma. In still further embodiments, the cancer is metastatic cancer.

In additional embodiments, the cancer-related target is a molecule associated with a cancerous cell or tissue. In some embodiments, the molecule is a tumor or tumor vasculature/stroma antigen, for example, CD20, CD19, CD30, CD3, GD2, Lewis-Y, 72 kd glycoprotein (gp72, decay-accelerating factor, CD55, DAF, C3/C5 convertases), CO17-1A (EpCAM, 17-1A, EGP-40), TAG-72, CSAg-P (CSAp), 45 kd glycoprotein, HT-29 ag, NG2, A33 (43 kd gp), 38 kd gp, MUC-1, CEA, EGFR (HER1), HER2, HER3, HER4, HN-1 ligand, CA125, syndecan-1, Lewis κ, FAP stromal Ag (fibroblast activation protein), EDG receptors (endoglin receptors), ED-B, laminin-5 (gamma2), cox-2 (+LN-5), PgP (P-glycoprotein), alphaVbeta3 integrin, alphaVbeta5 integrin, uPAR (urokinase plasminogen activator receptor), endoglin (CD105), GD2, aminopeptidase, tenascin-C, NG-2, TEM1, TEM8, annexin, folate receptor osteopontin (EDG 1,3), p97 (melanotransferrin), farnesyl transferase or a molecule in an apoptotic pathway (e.g., a death receptor, fas, caspase or bcl-2) or a lectin.

Due to the enzyme amplification of the detection reagent, antigens that are expressed at very low levels are detectable using the methods of the present invention. The detection sensitivity is reflective of the number of reporter molecules that have been bound to a target antigen through the methods of the present invention. Thus, the greater number of reporter molecules present, the greater the signal and the greater the sensitivity of the method. Therefore, binding of an enzyme that generates thousands of reporter molecules increases the sensitivity of the method. The enzymatic generation of multiple reporters helps ot overcome the stoichiometry of the binding moiety (i.e., 1:1; assuming there is one epitope for a specific binding agent).

In still further embodiments, the target is a blood cell, including hematopoietic cells (e.g., hematopoietic stem cells, as well as the various immature cells in the erythrocytic, thrombocytic, and leukocytic lineages. "Blood cells" include but are not limited to hematopoietic cells, erythrocytes, neutrophils, monocytes, platelets, mast cells, eosinophils, basophils, lymphocytes, B cells, T cells, plasma cells, mast cells, macrophages and natural killer cells. In some embodiments, the target is an abnormal blood cell. In some embodiments, the HSC targets have a surface antigen expression profile of CD34$^+$ Thy-1$^+$ or CD34$^+$ Thy-1$^+$ Lin$^-$ ("Lin$^-$" refers to a cell population selected on the basis of the lack of expression of at least one lineage specific marker). Methods for isolating and selecting HSCs are well known in the art (See e.g., U.S. Pat. Nos. 5,061,620, 5,677,136, and 5,750,397, each of which is incorporated herein in its entirety).

In other embodiments, the target is a molecule. In some embodiments, the molecule is an organic molecule. In further embodiments, the molecule is a biological molecule. In additional embodiments, the biological molecule is a cell-associated molecule. In still further embodiments, the cell-associated molecule is associated with the outer surface of a cell. In sortie embodiments, the cell-associated molecule is part of the extracellular matrix. In some additional embodiments, the cell-associated molecule is a protein. In some embodiments, the protein is a receptor. In additional embodiments, the cell-associated molecule is specific to a particular cell type. In further embodiments, the cell is a diseased and/or abnormal cell. In some preferred embodiments, the diseased cell is a cancer cell. In another embodiment, the diseased cell is an infected cell. Additional molecules that find use as targets in the present invention include, but are not limited to, proteins, peptides, nucleic acids, carbohydrates, lipids, polysaccharides, glycoproteins, hormones, receptors, antigens, antibodies, toxic substances, metabolites, inhibitors, drugs, dyes, nutrients and growth factors.

Non-limiting examples of protein and chemical targets encompassed by the present invention include chemokines and cytokines and their receptors. The term "cytokine" as used herein, refers to any of the numerous factors that exert a variety of effects on cells (e.g., inducing.

Growth, differentiation, and/or proliferation). Non-limiting examples include interleukins (IL), such as IL-2, IL-3, IL-4 µL-6, IL-10, IL-12, IL-13, IL-14 and IL-16; soluble IL-2 receptor; soluble IL-6 receptor; erythropoietin (EPO); thrombopoietin (TPO); granulocyte macrophage colony stimulating factor (GM-CSF); stem cell factor (SCF); leukemia inhibitory factor (LIF); interferons (e.g., IFN-alpha, -beta, and -gamma); oncostatin M (OM); the immunoglobulin superfamily; tumor necrosis factor (TNF) family, particularly TNF-α; transforming growth factors, (e.g., TGF-alpha and TGF-beta); and EL-1α; and vascular endothelial growth factor (VEGF) family, particularly VEGF (also referred to in the art as VEGF-A), VEGF-B, VEGF-C, VEGF-D and placental growth factor (PLGF). Cytokines are commercially available from several vendors including Amgen (Thousand Oaks, Calif.), Immunex (Seattle, Wash.) and Genentech (South San Francisco, Calif.). In some embodiments, particularly preferred targets are VEGF and TNF-α.

Antibodies against TNF-α show that blocking interaction of the TNF-α with its receptor is useful in modulating overexpression of TNF-α in several disease states such as septic shock, rheumatoid arthritis, and other inflammatory processes. VEGF is an angiogenic inducer, a mediator of vascular permeability and an endothelial cell-specific mitogen. VEGF has also been implicated in tumors. It is contemplated that targeting members of the VEGF family and/or their receptors will have significant therapeutic applications. For example, it is contemplated htat blocking VEGF will have therapeutic value in ovarian hyper stimulation syndrome (OHSS) (See e.g., Ferrara et al., Nat. Med., 5:1359 [1999]); and Gerber et al., Nat. Med., 5:623 [1999]). Other preferred targets include cell-surface receptors, such as T-cell receptors.

"Chemokines" are a family of small proteins that play an important role in cell trafficking and inflammation. Members of the chemokine family include, but are not limited to, IL-8, stomal-derived factor-1 (SDF-1), platelet factor 4, neutrophil activating protein-2 (NAP-2) and monocyte chemo attractant protein-1 (MCP-1). These proteins also find use as targets in the methods of the present invention.

Other protein and chemical targets include, but are not limited to: immunoregulation modulating proteins, such as soluble human leukocyte antigen (HLA, class I and/or class II and non-classical class I HLA (E, F and G)); surface proteins, such as soluble T or B cell surface proteins; human serum albumin; arachadonic acid metabolites, such as prostaglandins, leukotrienes, thromboxane and prostacyclin; IgE, auto or alloantibodies for autoimmunity or allo- or xenoimmunity; Ig Fc receptors or Fc receptor binding factors; G-protein coupled receptors; cell-surface carbohydrates; angiogenesis factors; adhesion molecules; ions, such as calcium, potassium, magnesium, aluminum and iron; fibril proteins, such as prions and tubulin; enzymes, such as proteases, aminopeptidases, kinases, phosphatases, DNAses, RNAases, lipases, esterases, dehydrogenases, oxidases, hydrolases, sulphatases, cyclases, transferases, transaminases, carboxylases, decarboxylases, superoxide dismutase and their natural substrates or analogs; hormones and their corresponding receptors, such as follicle stimulating hormone (FSH), leutinizing hormone (LH), thyroxine (T4 and T3), apolipoproteins, low density lipoprotein (LDL), very low density lipoprotein (VLDL), Cortisol, aldosterone, estriol, estradiol, progesterone, testosterone, dehydroepiandrosterone (DHBA) and its sulfate (DHEA-S); peptide hormones, such as renin, insulin, calcitonin, parathyroid hormone (PTH), human growth hormone (hGH), vasopressin and antidiuretic hormone (AD), prolactin, adrenocorticotropic hormone (ACTH), LHRH, thyrotropin-releasing hormone (THRH), vasoactive intestinal peptide (VIP), bradykinin and corresponding prohormones; catechcolamines such as adrenaline and metabolites; cofactors including atrionatriutic factor (AdF), vitamins A, B, C, D, E and K and serotonin; coagulation factors, such as prothrombin, thrombin, fibrin, fibrinogen, Factor VIII, Factor IX, Factor XI and von Willebrand factor; plasminogen factors, such as plasmin, complement activation factors, LDL and ligands thereof and uric acid; compounds regulating coagulation, such as hirudin, hirulog, hementin, heparin and tissue plasminigen activator (TPA); nucleic acids for gene therapy; enzyme antagonists; compounds that bind ligands, such as inflammation factors and receptors and other proteins that bind to one or more of the preceding molecules.

Additional chemical targets include without limitation drugs, especially drugs subject to abuse, such as cannabis, heroin and other opiates, phencyclidine (PCP), barbiturates, cocaine and its derivatives and benzadiazepine; toxins, such as heavy metals like mercury and lead, arsenic and radioactive compounds; chemotherapeutic agents, such as paracetamol, digoxin and free radicals; bacterial toxins, such as lipopolysaccharides (LPS) and other gram negative toxins, Staphylococcus toxins, toxin A, tetanus toxins, diphtheria toxin, and pertussis toxins; plant and marine toxins; snake and other venoms, virulence factors, such as aerobactins, toxins, proteins, etc.; infectious viruses, such as hepatitis, cytomegalovirus (CMV), herpes simplex viruses (e.g., HSV types 1, 2 and 6), Epstein-Barr virus (EBV), varicella zoster virus (VZV), human immunodeficiency viruses (e.g., HIV-1, -2) and other retroviruses, adenoviruses, rotaviruses, influenzae, rhinoviruses, parvoviruses, rubella, measles virus, polio, paramyxoviruses, papovaviruses, poxviruses, arboviruses, flaviviruses, arenaviruses, rabies virus, caliciviruses, astroviruses, rotaviruses, and picornaviruses; prions; plasmodia tissue factor, protozoans, including amebae (e.g., *Entamoeba histolytica*), filariae (e.g., *Wuchereria*), *Plasmodium, Giardia, Leishmania, Oyptosporidium, Sarcocystis, Babesia, Trypanosoma*, and *Toxoplasma*: helminths (e.g., trematodes, cestodes and nematodes); bacteria, including aerobic, anaerobic and facultative bacteria responsible for sepsis, nosocomial, and other infections (e.g., *E. coli, Acinetobacter, Pseudomonas, Proteus, Klebsiella, Staphylococcus, Streptococcus, Neisseria*, mycobacteria, *Legionnella, Clostridium, Mycoplasma, Treponema, Chlamydia, Rickettsia, Bartonella*, etc.) and fungi (e.g., *Candida, Pneumocystis, Aspergillus, Trichosporum, Microsporum, Pichnia, Coccidioides, Blastomyces, Histoplasma, Cryptococcus*, etc.). Indeed, it is not intended that the present invention be limited to any particular target, as any target that can be bound (i.e., to form a bound target) finds use in the present invention).

In further embodiments, the target is a plant or plant-derived material. In some embodiments, the target is wood, while in other embodiments, the target is a non-woody plant. It is intended that the present invention encompass any plant and/or plant-derived material.

In some embodiments, the target is an enzyme such as proteases, aminopeptidases, kinases, phosphatases, DNAses, RNAases, lipases, esterases, dehydrogenases, oxidases, hydrolases, sulphatases, cellulases, cyclases, transferases, transaminases, carboxylases, decarboxylases, superoxide dismutase, and their natural substrates or analogs. Particularly preferred enzymes include hydrolases, particularly alphafoeta hydrolases; serine proteases, such as subtilisins, and chymotrypsin serine proteases; cellulases and lipases.

In yet additional embodiments, the surface is a non-biological surface. In some embodiments, the non-biological surface is a surface of a medical device. In further embodiments, the medical device is a therapeutic device. In yet other embodiments, the therapeutic device is an implanted therapeutic device. In additional embodiments, the medical device is a diagnostic device. In some embodiments, the diagnostic device is a well or tray.

In further embodiments, the target is a non-biological material. In some embodiments, the non-biological material is a fabric. In some preferred embodiments, the fabric is a natural fabric. In additional embodiments, the fabric is cotton, silk and/or wool. In further embodiments, the fabric is a non-natural fabric. In some embodiments, the fabric is nylon, rayon and/or polyester. In some embodiments, the fabric is a blend of natural and/or synthetic fibers. In still further embodiments, the non-biological material is a plastic, ceramic, metal, and/or rubber. In additional embodiments, the material is a composite material of any of the above.

In additional embodiments, the target is a microcircuit. This circuit can be in its finished form or in any stage of circuit manufacturing. The targeted agent can be used to remove or deposit a compound onto the circuit, for example, an n-type dopant (e.g., arsenic, phosphorus, antimony, titanium or other donor atom species) or a p-type dopant (e.g., boron, aluminum, gallium, indium or other acceptor atom species) (See, e.g., van Zant, *Microchip Fabrication*, McGraw-Hill, New York, [2000]), incorporated herein by reference in its entirety.

Indeed, it is not intended that the present invention be limited to any particular target, as any target that can be bound (i.e., to form a bound target) finds use in the present invention).

In a preferred embodiment, the method includes the additional step of analyzing the results obtained after the substrate has been added to the test system. Such analysis can be made using any suitable method, including but not limited to a readout system comprising a computer (e.g., PC-based or other with aufficient RAM (>250 MB), and video board) and software (any commercially available image analysis program, e.g. ImagePro, Metamorph), photographic film (any standard color film of appropriate ASA) or other means (e.g., PMT-based imaging systems, photodiode-based systems) for generating image and/or numerical data from emitted photons. Indeed, it is not intended that the present invention be limited to any particular analysis method.

Experimental

The following examples serve to illustrate certain preferred embodiments and aspects of the present invention and are not to be construed as limiting the scope thereof.

In the experimental disclosure which follows, the following abbreviations apply: sd and SD (standard deviation); M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); μm (micrometers); nm (nanometers); ° C. (degrees Centigrade); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); g (gravity); OD (optical density); CPM and cpm (counts per minute); rpm (revolutions per minute); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); B-PER (bacterial protein extraction reagent; Pierce); 2-ME (2-mercaptoethanol); EGTA (ethylene glycol-bis(β-aminoethyl ether) N,N,N',N'-tetraacetic acid); EDTA (ethylenediaminetetracetic acid); bla (β-lactamase or ampicillin-resistance gene); Aptagen (Herndon, Va.); Biodesign (Biodesign Intl., Saco, Maine); Takara (Takara Bio Inc., Shiga, Japan); ATCC (American Type Culture Collection, Rockville, Md.); Gibco/BRL (Gibco/BRL, Grand Island, N.Y.); Oxoid (Oxoid, Ltd., Basingstoke, England); Pierce (Pierce Biotechnology, Inc., Rockford, Ill.); Sigma (Sigma Chemical Co., St. Louis, Mo.); Pharmacia (Pharmacia Biotech. Piscataway, N.J.); Invitrogen (Invitrogen, Corp., Carlsbad, Calif.); Stratagene (Stratagene, La Jolla, Calif.); Polysciences (Polysciences, Inc., Warrington, Pa.); Dako (DakoCytomation, Inc., Carpinteria, Calif.); Cemicon (Cemicon International, Temecula Calif.); Leica (Leica Microsystems, Wetzlar, Germany); Hamamatsu (Hamamatsu, Corp., Hamamatsu, Japan); Ardais (Ardais Corp., Lexington. MA); Kodak (Eastman-Kodak, Rochester, N.Y.); Omega (Omega Optical Inc., Brattleboro, Vt.); and Molecular Devices (Molecular Devices, Sunnyvale, Calif.).

Example 1

Construction of CAB 1.2 Molecule

Figure 12A:
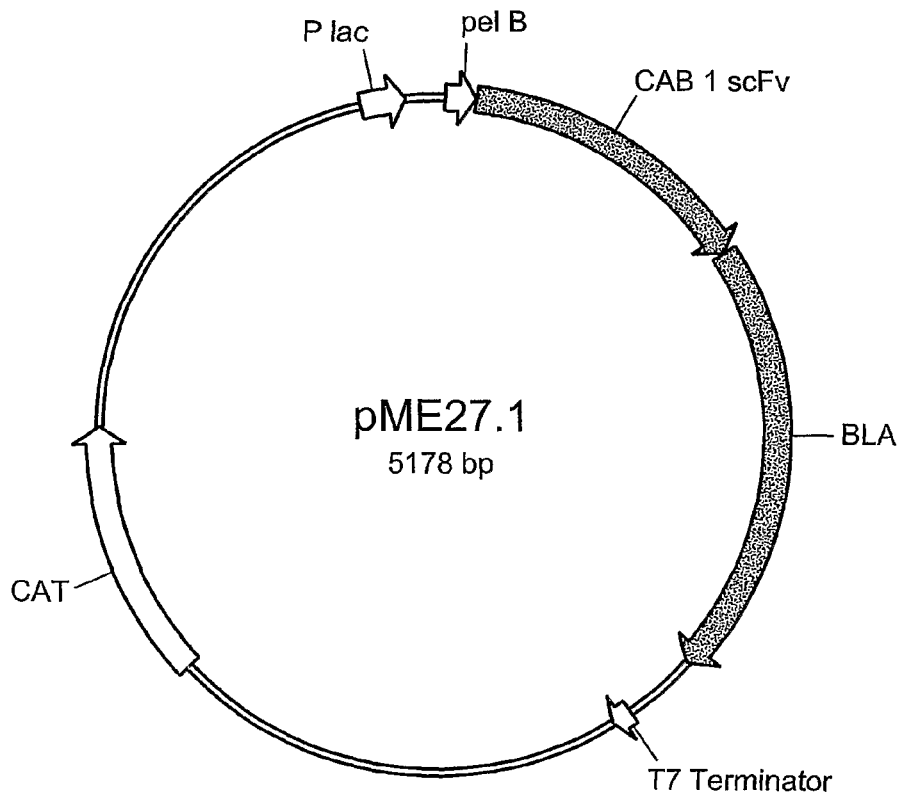
FIG. 12 provides CAB molecules sequences. Panel 12A provides a plasmid map for pME27.1. Panel 12B provides the CAB sequence, indicating heavy (SEQ ID NO:3) and light chain (SEQ ID NO:4), as well as linker (SEQ ID NO:5), and BLA (SEQ ID NO:6) domains.

In this Example, the construction of CAB 1.2 is described. Plasmid pME27.1 was generated by inserting a BglI-EcoKV fragment encoding a part of the pelB leader, the CAB1-scFv and a small part of BLA into the expression vector pME25. FIG. 12A provides a map of this plasmid. The insert which encoded CAB1-scFv was synthesized by Aptagen, based on the sequence of the scFv MFE-23 (See, Boehm et al., Biochem. J., 346(Pt 2): 519-528 [2000]). Both the plasmid containing the synthetic gene (pPCR-GME1) and pME25 were digested with Bg and EcoRV, gel purified, and ligated with Takara ligase. The ligation products were transformed into TOP10 (Invitrogen) electrocompetent cells, and plated on LA medium containing 5 mg/l chloramphenicol and 0.1 mg/l cefotaxime. Plasmid pME27.1 contained the following components.

| Plasmid pME27.1 Components | |
|---|---|
| P lac | 4992-5113 bp |
| pel B leader | 13-78 bp |
| CAB 1 scFv | 79-810 bp |
| BLA | 811-1896 bp |
| T7 term. | 2076-2122 bp |
| CAT | 3253-3912 bp |

As indicated above, a map of plasmid pME27.1 is provided in FIG. 12A. FIG. 12B provides the CAB1 sequence, including the sequences of the heavy (SEQ ID NO:3) and light (SEQ ID NO:4) chain domains, as well as the linker sequence (SEQ ID NO:5), and the BLA sequence (SEQ ID NO:6).

Choosing Mutations for Mutagenesis

The sequence of the vH and vL sequences of CAB1-scFv were compared with a published frequency analysis of human antibodies (See, Steipe, Sequenzdatenanalyse, (Sequence Data Analysis, available in German only) in Zorbas and Lottspeich, *Bioanalvtik*, Spektrum Akademischer Verlag, S. 233-241 [1998] prepared by aligning sequences of variable segments of human antibodies found in the Kabat database, and calculating the frequency of occurrence of each amino acid for each position. These comparisons are provided in FIG. 13. Specifically, FIG. 13A provides a comparison of the observed frequencies of the five most abundant amino acids in alignment of human sequences in the heavy chain, while FIG. 13B provides a comparison of the observed frequencies of the five most abundant amino acids in human light chain sequences.

These frequencies were compared with the actual amino acid sequence of CAB1 and identified 33 positions that fulfilled the following criteria: the position is not part of a CDR as defined by the Kabat nomenclature; the amino acid found in CAB1-scFv is observed in the homologous position in less than 10% of human antibodies; and the position is not one of the last 6 amino acids in the light chain of scFv. The resulting 33 positions were chosen for combinatorial mutagenesis conducted as described below.

Mutagenic oligonucleotides were synthesized for each of the 33 positions such that the targeted position would be changed from the amino acid in CAB1-scFv to the most abundant amino is acid in the homologous position of a human antibody. FIG. 12B shows the sequence of CAB1-scFv, the CDRs and the mutations that were chosen for combinatorial mutagenesis.

Construction of Library NA05

Table 1 provides the sequences of 33 mutagenic oligonucleotides that were used to generate to combinatorial library NA05:

TABLE 1

Oligonucleotides Used to Generate Library NA05

| pos. (pME27) | MFE-23 | consensus aa (VH) | count residues to be changed | QuikChange Multi Primer | SEQ ID NO: |
|---|---|---|---|---|---|
| 3 | K | Q | nsa147.1fp | CGGCCATGGCCCAGGTGCAGCTGCAGCAGTCTGGGGC | SEQ ID NO: 7 |
| 13 | R | K | nsa147.2fp | CTGGGGCAGAACTTGTGAAATCAGGGACCTCAGTCAA | SEQ ID NO: 8 |
| 14 | S | P | nsa147.3fp | GGGCAGAACTTGTGAGGCCGGGGACCTCAGTCAAGTT | SEQ ID NO: 9 |
| 16 | T | G | nsa147.4fp | AACTTGTGAGGTCAGGGGGCTCAGTCAAGTTGTCCTG | SEQ ID NO: 10 |

TABLE 1-continued

Oligonucleotides Used to Generate Library NA05

| pos. (pME27) | MFE-23 | consensus aa (VH) | count residues to be changed | QuikChange Multi Primer | SEQ ID NO: |
|---|---|---|---|---|---|
| 28 | N | T | nsa147.5fp | GCACAGCTTCTGGCTTCACCATTAAAGACTCCTATAT | SEQ ID NO: 11 |
| 29 | I | F | nsa147.6fp | CAGCTTCTGGCTTCAACTTTAAAGACTCCTATATGCA | SEQ ID NO: 12 |
| 30 | K | S | nsa147.7fp | CTTCTGGCTTCAACATTAGCGACTCCTATATGCACTG | SEQ ID NO: 13 |
| 37 | L | V | nsa147.8fp | ACTCCTATATGCACTGGGTGAGGCAGGGGCCTGAACA | SEQ ID NO: 14 |
| 40 | G | A | nsa147.9fp | TGCACTGGTTGAGGCAGGCGCCTGAACAGGGCCTGGA | SEQ ID NO: 15 |
| 42 | E | G | nsa147.10fp | GGTTGAGGCAGGGGCCTGGCCAGGGCCTGGAGTGGAT | SEQ ID NO: 16 |
| 67 | K | R | nsa147.11fp | CCCCGAAGTTCCAGGGCCGTGCCACITTTACTACAGA | SEQ ID NO: 17 |
| 68 | A | F | nsa147.12fp | CGAAGTTCCAGGGCAAGTTCACTTTTACTACAGACAC | SEQ ID NO: 18 |
| 70 | F | I | nsa147.13fp | TCCAGGGCAAGGCCACTATTACTACAGACACATCCTC | SEQ ID NO: 19 |
| 72 | T | R | nsa147.14fp | GCAAGGCCACTTTTACTCGCGACACATCCTCCAACAC | SEQ ID NO: 20 |
| 76 | S | K | nsa147.15fp | TTACTACAGACACATCCAAAAACACAGCCTACCTGCA | SEQ ID NO: 21 |
| 97 | N | A | nsa147.16fp | CTGCCGTCTATTATTGTGCGGAGGGGACTCGGACTGG | SEQ ID NO: 22 |
| 98 | E | R | nsa147.17fp | CCGTCTATTATTGTAATCGCGGGACTCCGACTGGGCC | SEQ ID NO: 23 |
| 136 | E | Q | nsa147.18fp | CTGGCGGTGGCGGATCACAGAATGTGCTCACCCAGTC | SEQ ID NO: 24 |
| 137 | N | S | nsa147.19fp | GCGGTGGCGGATCAGAAAGCGTGCTCACCCAGTCTCC | SEQ ID NO: 25 |
| 142 | S | P | nsa147.20fp | GAAAATGTGCTCACCCAGCCGCGAGCAATCATGTCTGC | SEQ ID NO: 26 |
| 144 | A | S | nsa147.21fp | TGCTCACCCAGTCTCCAAGCATCATGTCTGCATCTCC | SEQ ID NO: 27 |
| 146 | M | V | nsa147.22fp | CCCAGTCTCCAGCAATCGTGTCTGCATCTCCAGGGGA | SEQ ID NO: 28 |
| 152 | E | Q | nsa147.23fp | TGTCTGCATCTCCAGGGCAGAAGGTCACCATAACCTG | SEQ ID NO: 28 |
| 153 | K | T | nsa147.24fp | CTGCATCTCCAGGGGAGACCGTCACCATAACCTGCAG | SEQ ID NO: 30 |
| 170 | F | Y | nsa147.25fp | TAAGTTACATGCACTGGTACCAGCAGAAGCCAGGCAC | SEQ ID NO: 31 |
| 181 | W | V | nsa147.26fp | GCACTTCTCCCAAACTCGTGATTTATAGCACATCCAA | SEQ ID NO: 32 |
| 194 | A | D | nsa147.27fp | TGGCTTCTGGAGTCCCTGATCGCTTCAGTGGCAGTGG | SEQ ID NO: 33 |
| 200 | G | K | nsa147.28fp | CTCGCTTCAGTGGCAGTAAATCTGGGACCTCTTACTC | SEQ ID NO: 34 |
| 205 | Y | A | nsa147.29fp | GTGGATCTGGGACCTCTGCGTCTCTCACAATCAGCCG | SEQ ID NO: 35 |
| 212 | M | L | nsa147.30fp | CTCTCACAATCAGCCGACTGGAGGCTGAAGATGCTGC | SEQ ID NO: 36 |
| 217 | A | E | nsa147.31fp | GAATGGAGGCTGAAGATGAAGCCACTTATTACTGCCA | SEQ ID NO: 37 |
| 219 | T | D | nsa147.32fp | AGGCTGAAGATGCTGCCGATTATTACTGCCAGCAAAG | SEQ ID NO: 38 |
| 234 | A | G | nsa147.33fp | ACCCACTCACGTTCGGTGGCGGCACCAAGCTGGAGCT | SEQ ID NO: 39 |

The QuikChange multi site-directed mutagenesis kit (QCMS; Stratagene) was used to construct the combinatorial library NA05 using the above 33 mutagenic primers. The primers were designed so that they had 17 bases flanking each side of the codon of interest based on the template plasmid pME27.1. The codon of interest was changed to encode the appropriate consensus amino acid using an *E. coli* codon usage table. All primers were designed to anneal to the same strand of the template DNA (i.e., all were forward primers in this case). The QCMS reaction was carried out as described in the QCMS manual with the exception of the primer concentration used; the QCMC manual recommends using 50 ng of each primer in the reaction, whereas, in these experiments, 3 ng of each primer were used (thus, other primer amounts find use). In particular, the reaction contained 50-100 ng template plasmid (pME27.1; 5178 bp), 1 μl of primer mix (10 μM stock of all primers combined containing 0.3 μM each primer), 1 μl dNTPs (QCMS kit), 2.5 μl 10× QCMS reaction buffer, 18.5 μl deoinized water and 1 μl enzyme blend (QCMS kit) for a total volume of 25 μl. The thermocycling program used was: 1 cycle at 95° C. for 1 min., followed by 30 cycles of 95° C. for 1 min., 55° C. for 1 min. and then 65° C. for 10 minutes. DpnI digestion was performed by adding 1 µl DpnI (provided in the QCMS kit), incubation at 37° C. for 2 hours, addition of another 1 µl DpnI, and incubation at 37° C. for an additional 2 hours. Then, 1 µl of the reaction was transformed into 50 µl of TOP10 electrocompetent cells (Invitrogen). Then, 250 µl of SOC was added after electroporation, followed by one hour of incubation with shaking, at 37° C. Following this incubation period, 10-50 µl of the tranformation mix were plated on LA plates containing 5 ppm chloramphenicol (CMP) or LA plates containing 5 ppm CMP and 0.1 ppm of cefotaxime (CTX) for selection of active BLA clones. The active BLA clones from the CMP+CTX plates were used for screening, whereas the random library clones from the CMP plates were sequenced to assess the quality of the library.

Sixteen randomly chosen clones were sequenced. These clones were found to contain different combinations of 1 to 7 mutations.

Screen for Improved Expression

Upon culturing TOP10/pME27 in LB medium at 37° C., the concentration of intact fusion protein was found to peak after one day and most of the fusion protein was degraded by host proteases after 3 days of culture. Degradation appeared to occur mainly in the scFv portion of the CAB1 fusion protein, as the cultures contained significant amounts of free BLA after 3 days, which could be detected by Western blotting, or a nitrocefin (Oxoid) activity assay. Thus, a screen applied to library NA05 was able to detect variants of CAB1-scFv that would resist degradation by host proteases over 3 days of culture at 37° C.

Library NA05 was plated onto agar plates with LA medium containing 5 mg/l chloramphenicol and 0.1 mg/l cefotaxime (Sigma). After incubation, 910 colonies were transferred into a total of 10 96-well plates containing 100 ul/well of LA medium containing 5 mg/l chloramphenicol and 0.1 mg/l cefotaxime. Four wells in each plate were inoculated with TOP10/pME27.1 as control and one well per plate was left as a blank. The plates were grown overnight at 37° C. The next day the cultures were used to inoculate fresh plates (production plates) containing 100 ul of the same medium using a transfer stamping tool. Glycerol was then added to the master plates, which were stored at −70° C. The production plates were incubated in a humidified shaker at 37° C. for 3 days. Following this incubation, 100 ul of B-PER (Pierce) per well was added to the production plate to release protein from the cells. The production plate was diluted 100-fold in PBST (PBS containing 0.125% TWEEN®-20) and BLA activity was measured by transferring 20 ul diluted lysate into 180 ul of nitrocephin assay buffer (0:1 mg/ml nitrocephin in 50 mM PBS buffer containing 0.125% octylglucopyranoside (Sigma)) and the BLA activity was determined at 490 nm using a Spectramax plus plate reader (Molecular Devices).

Binding to CEA (Biodesign Intl., Saco, Maine) was measured using the following procedure: 96-well plates were coated with 100 ul per well of 5 ug/ml of CEA in 50 mM carbonate buffer pH 9.6 overnight. The plates were washed with PBST and blocked for 1-2 hours with 300 ul casein (Pierce). Then, 100 ul of sample from the production plate diluted 100-1000 fold were added to the CEA-coated plate and the plates were incubated for 2 h at room temperature. Subsequently, the plates were washed four times with PBST and 200 ul nitrocefin assay buffer were added, and the BLA activity was measured as described above.

The BLA activity that was determined by the CEA-binding assay and the total BLA activity found in the lysate plates were compared and variants were identified that showed high levels of total BLA activity and high levels of CEA-binding activities.

Figure 14A:
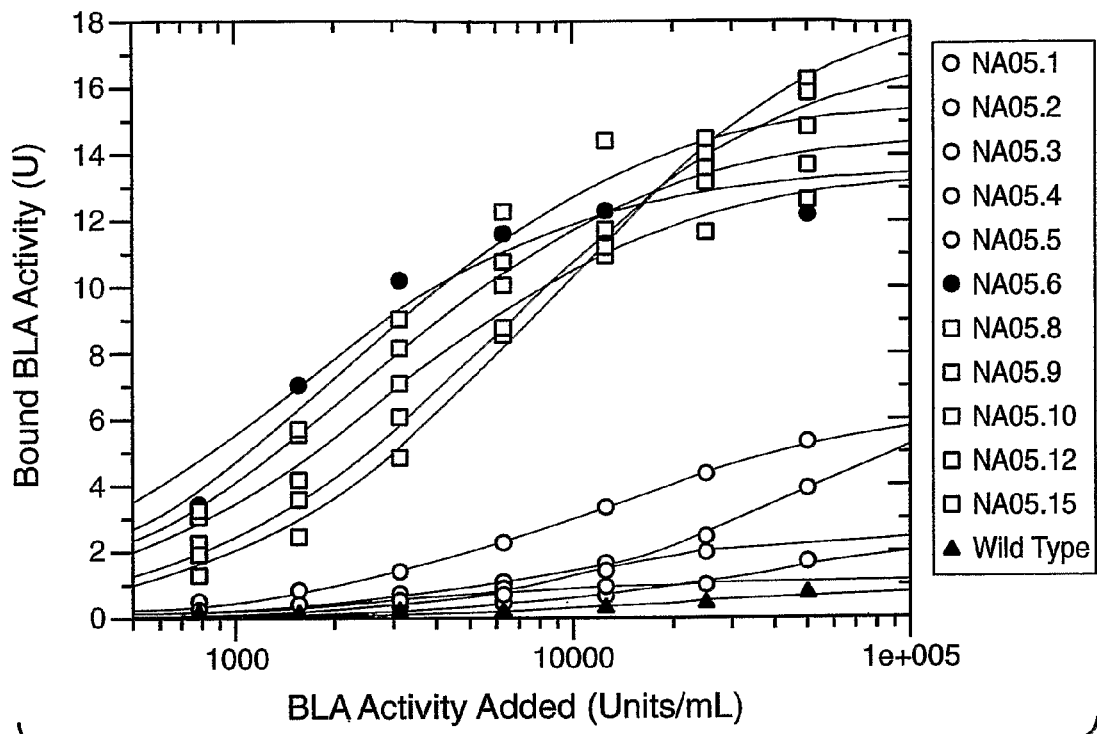
FIG. 14 provides data relevant to isolation of a CAB molecule, as described in Example 1. Panel 14A provides a graph showing the binding curve of bound BLA activity as compared to BLA activity added. Panel 14B provides a photograph of an SDS-PAGE gel of 7 variants from NA05.
Figure 14B:
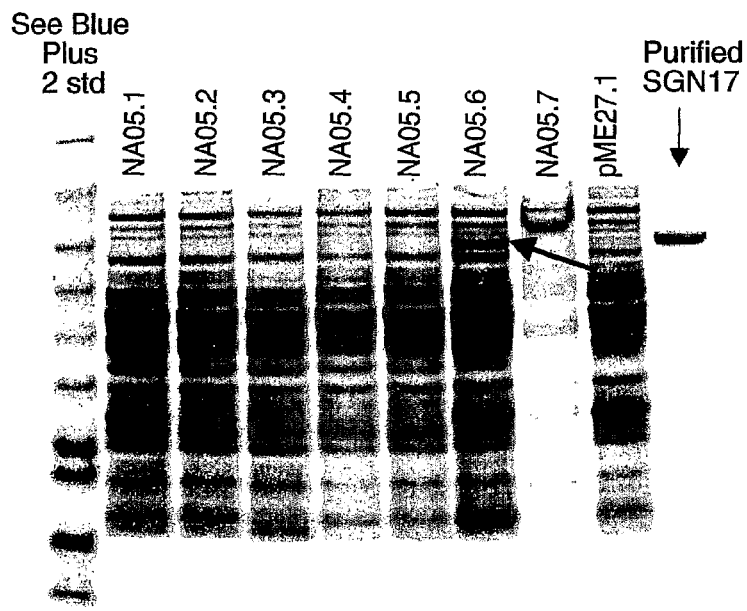
Figure 15A:
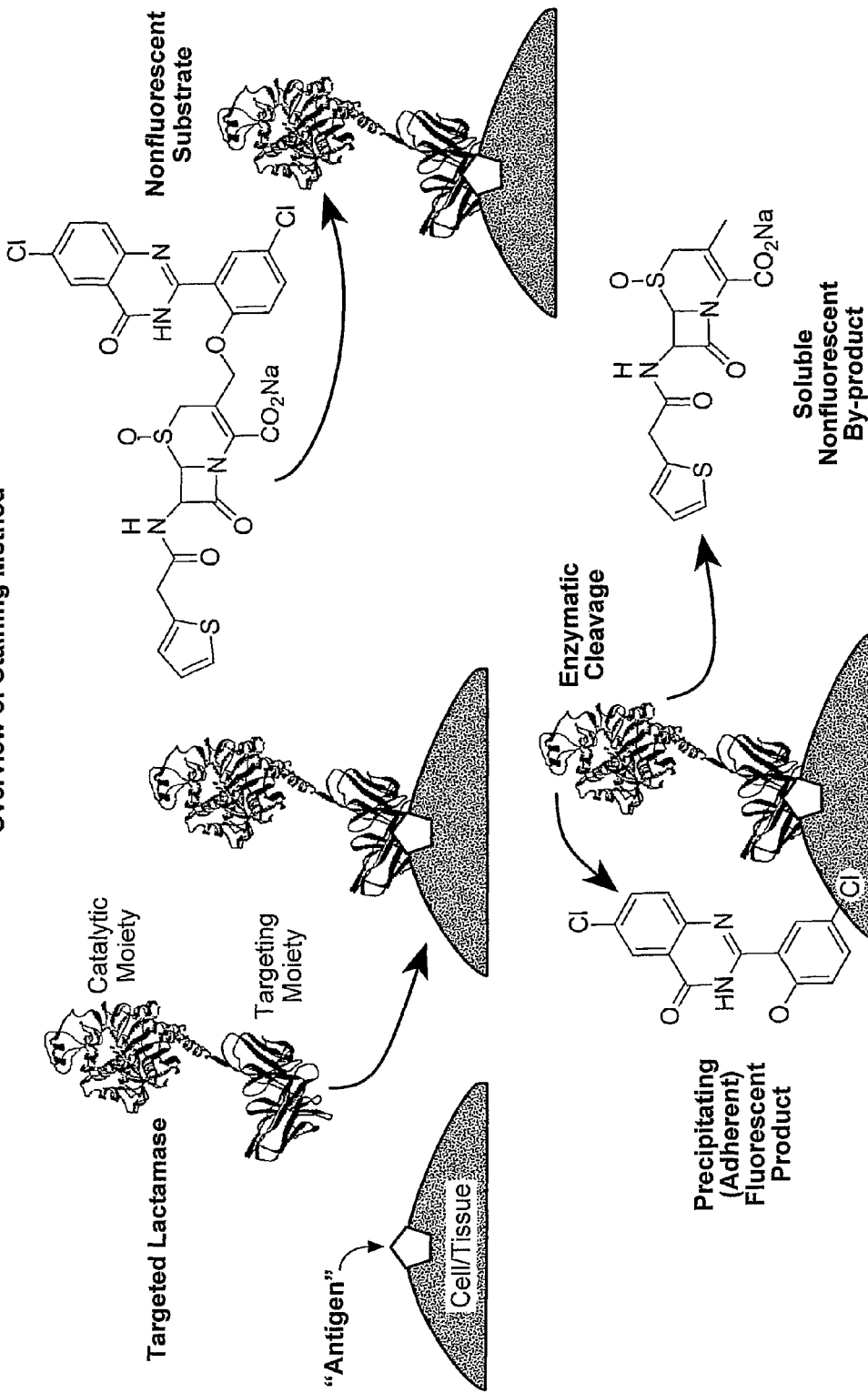
FIG. 15 provides a pictoral overview of an embodiment of staining method and imaging method. Panel 15A illustrates an embodiment of the staining method, while Panel 15B provides an embodiment of the imaging method.
Figure 15B:
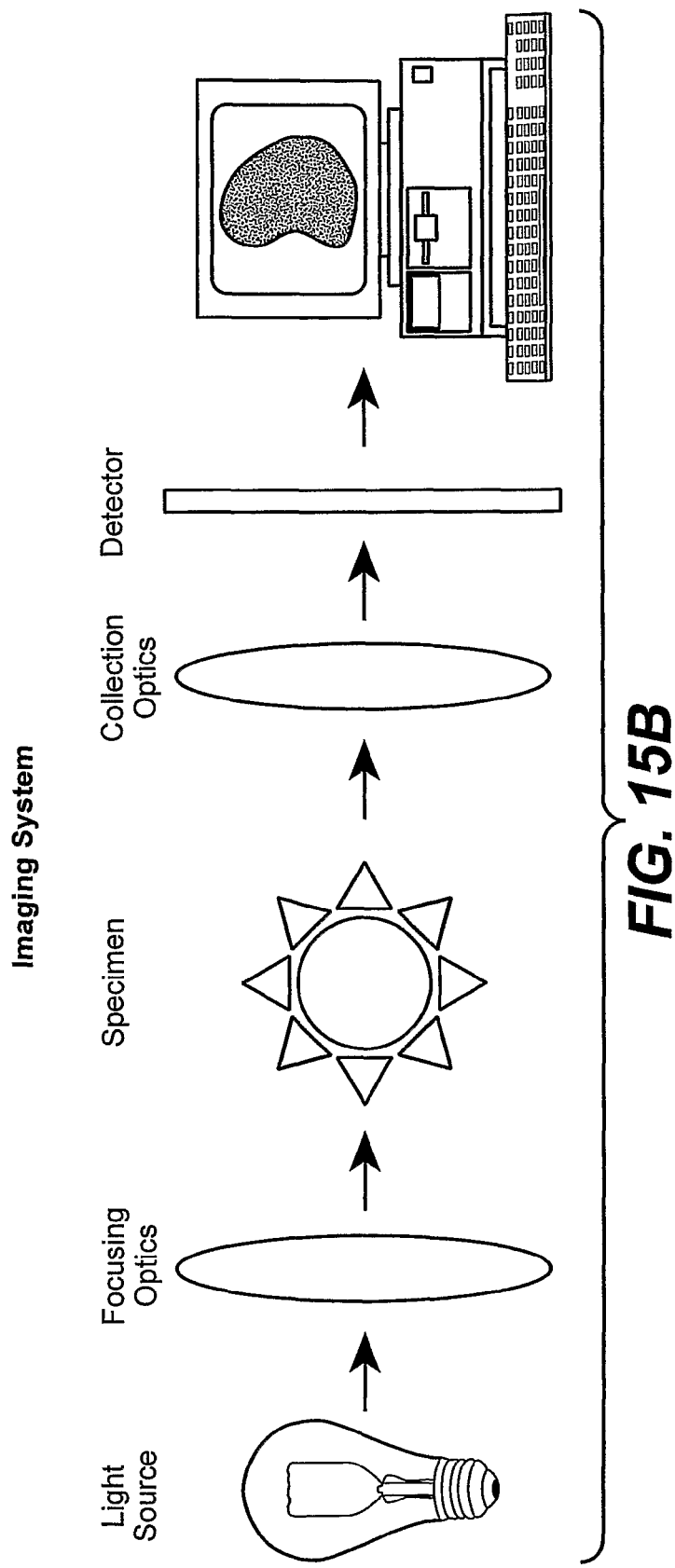
Figure 16A:
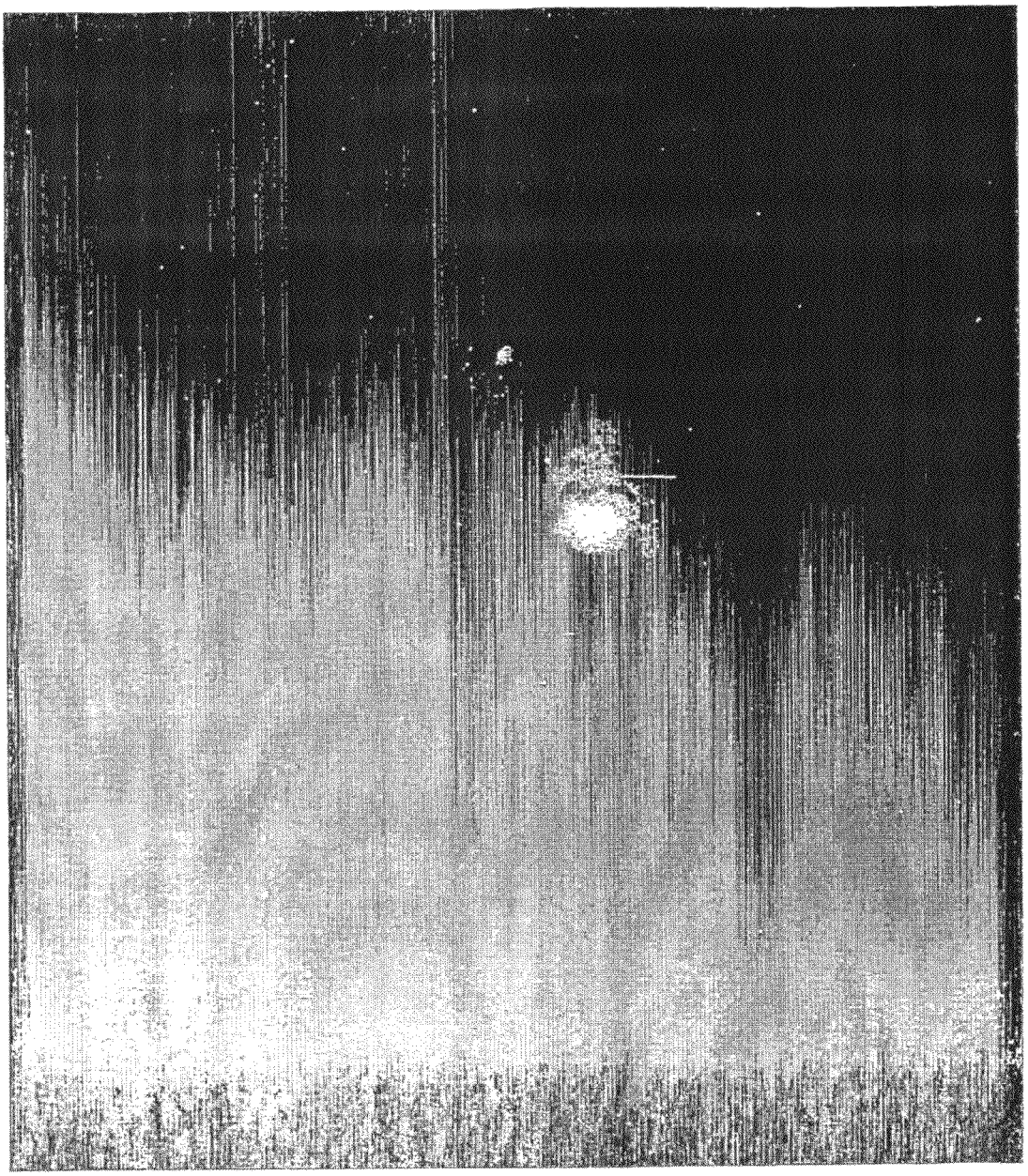
FIG. 16 provides photographs of in vivo imaging with a lactamase reporter as described in Example 10. Panels 16A-16G illustrate the use of several excitation and emission spectra, as set forth in the drawings.
Figure 16B:
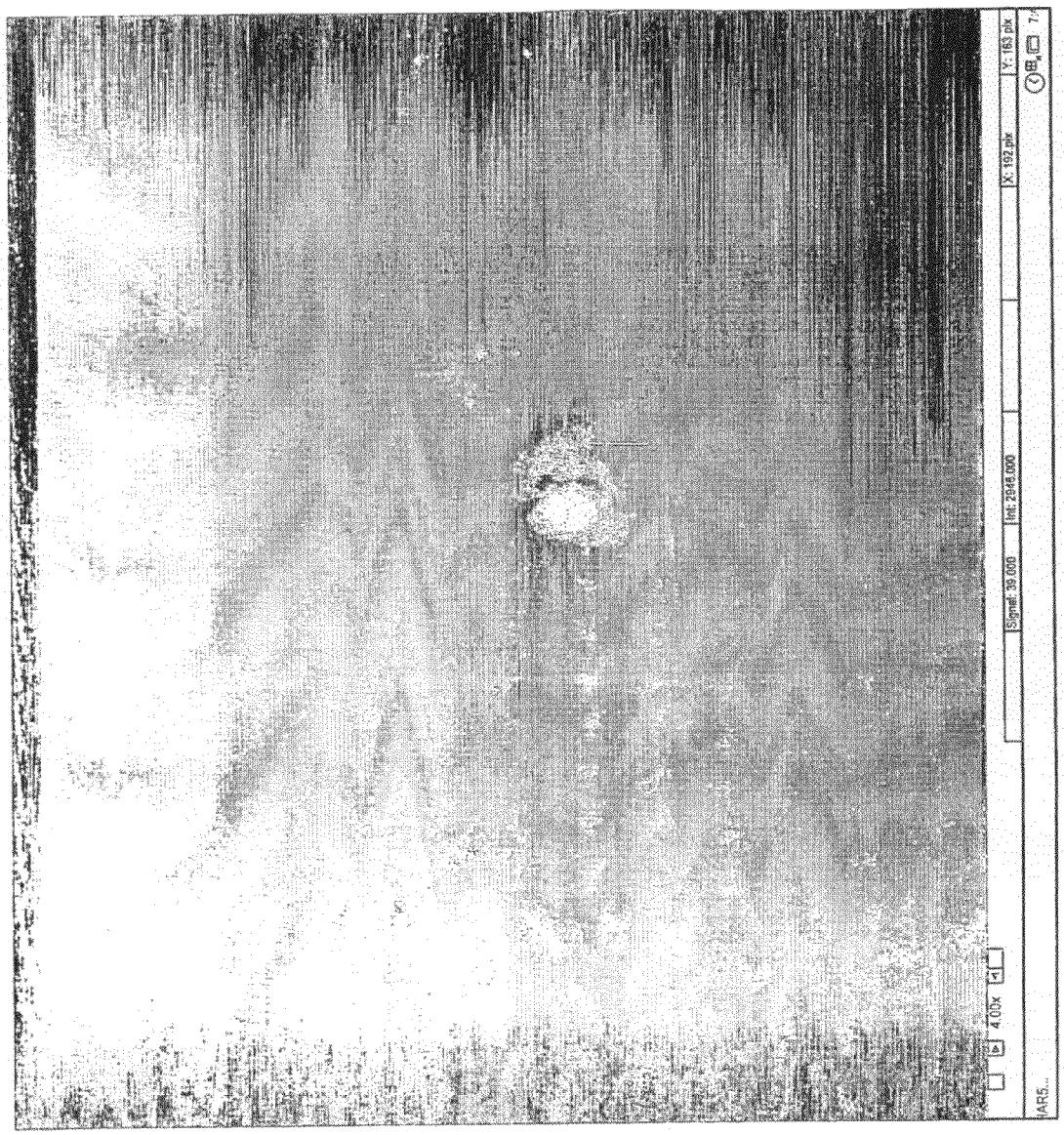
Figure 16C:
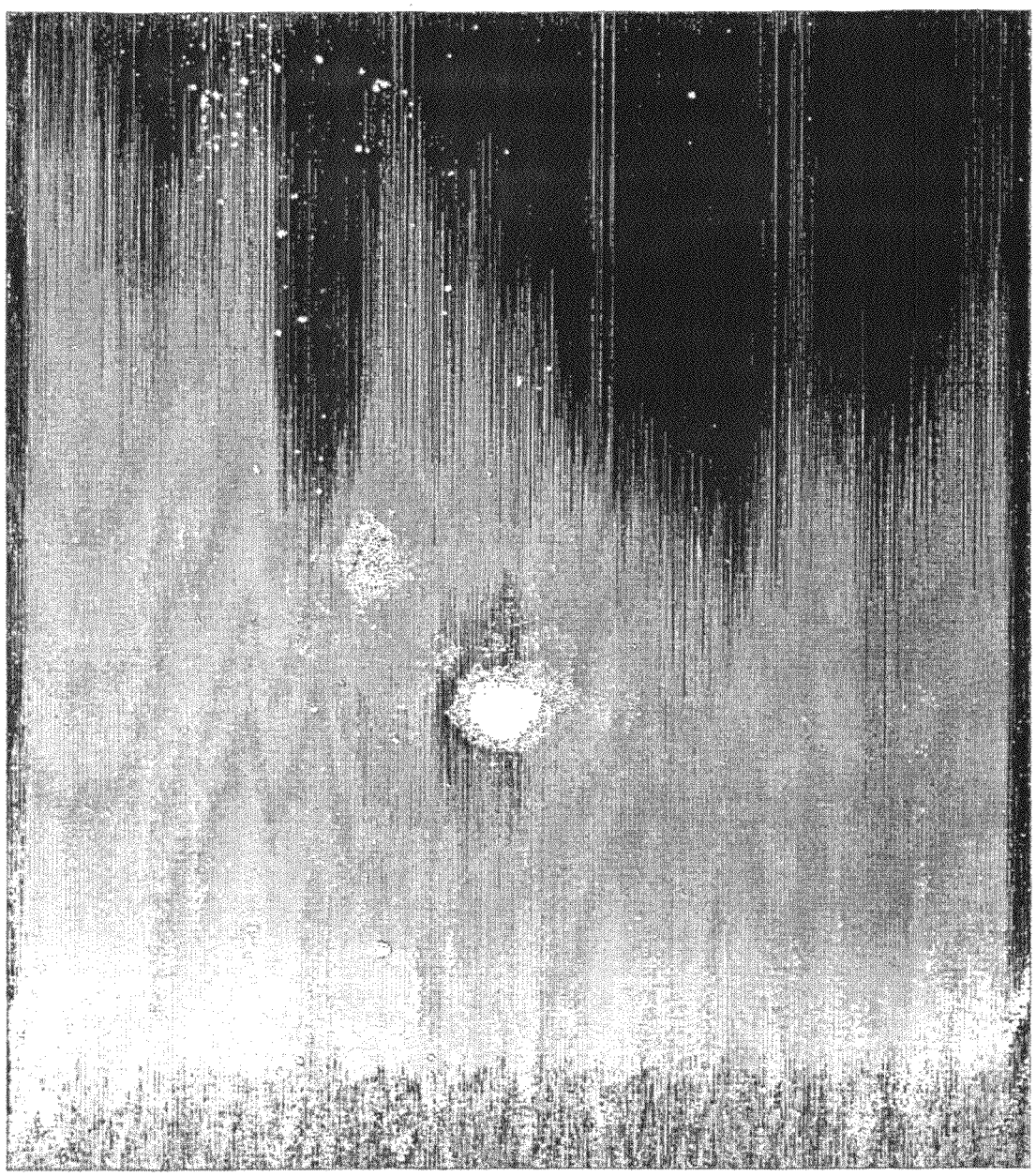
Figure 16D:
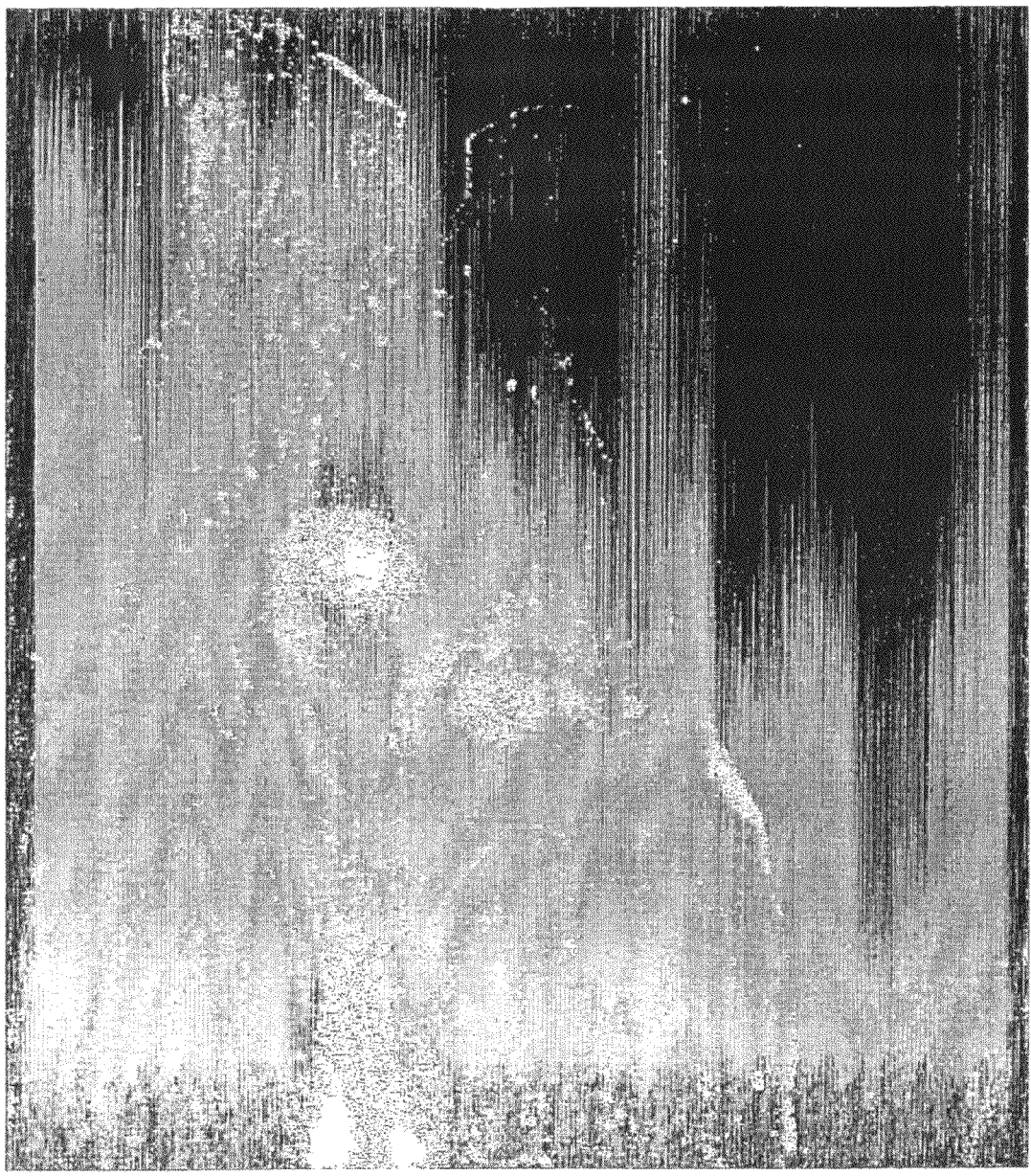
Figure 16E:
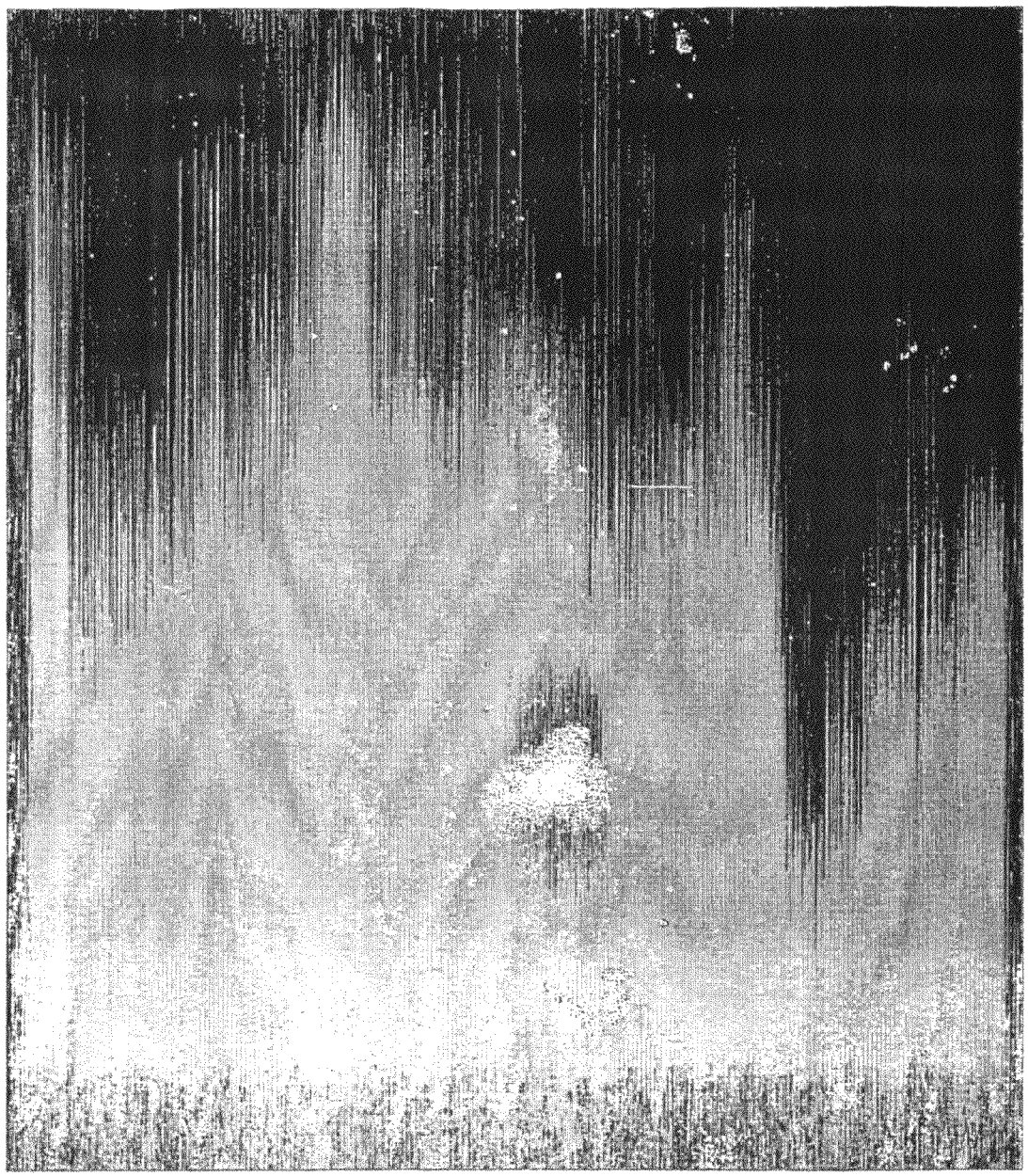
Figure 16F:
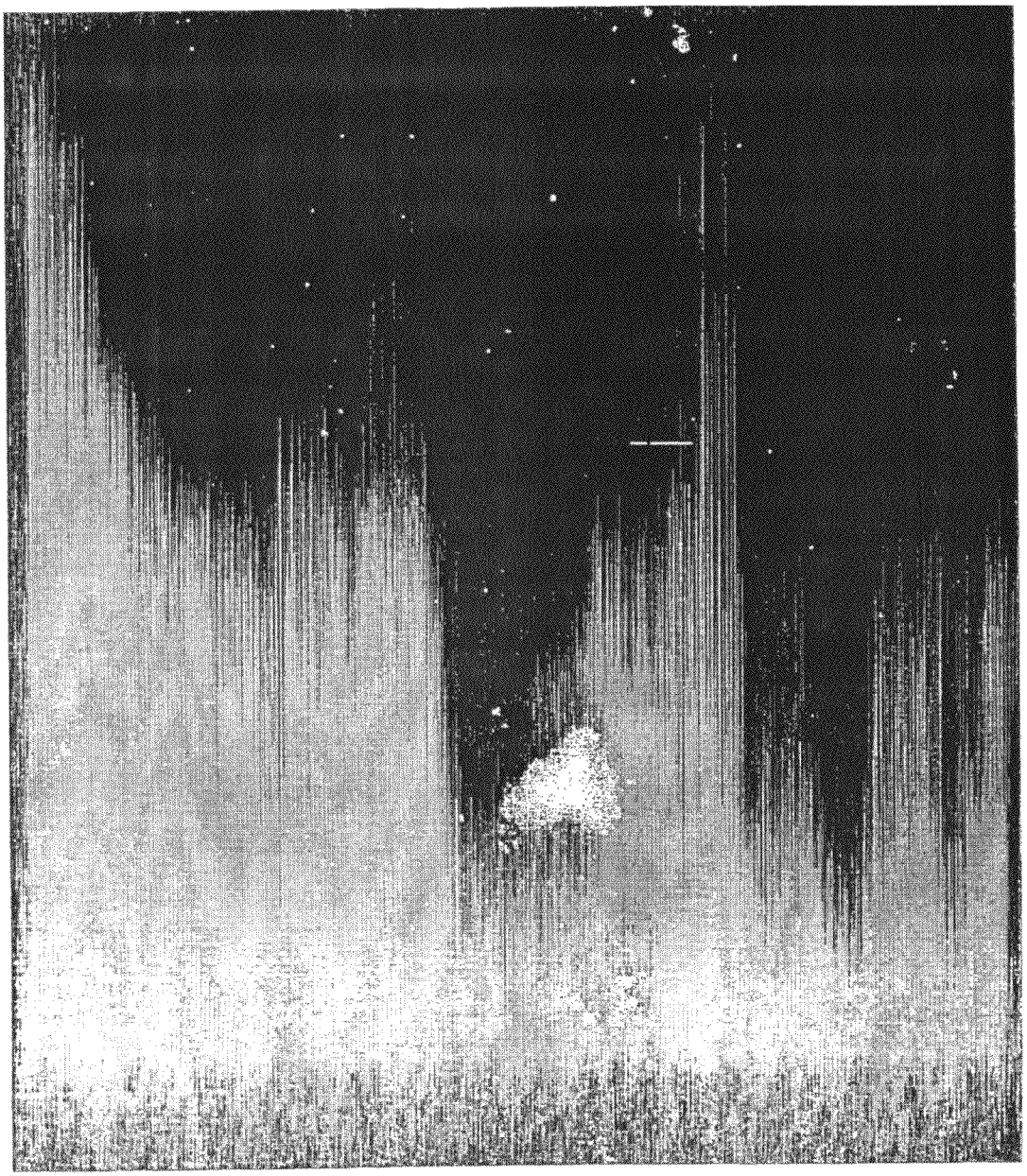
Figure 16G:
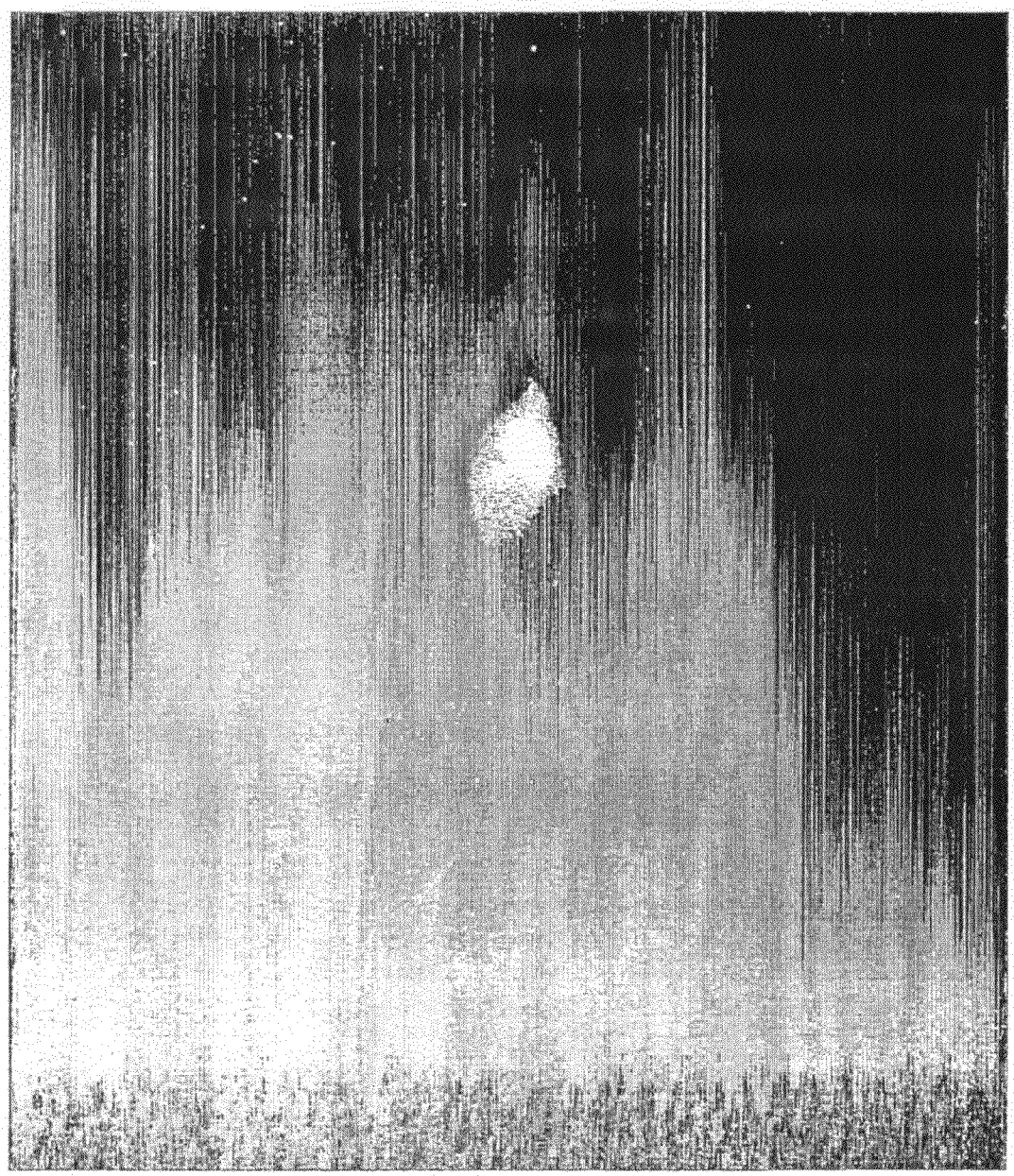

The winners were confirmed in 4 replicates using a similar protocol: the winners were cultured in 2 ml of LB containing 5 mg/l chloramphenicol and 0.1 mg/l cefotaxime for 3 days. Protein was released from the cells using B-PER reagent. The binding assay was performed as described above but different dilutions of culture lysate were tested for each variant. FIG. 14A provides binding curves obtained from these results. Culture supernatants were also analyzed by SDS-PAGE, as shown in FIG. 14B, which provides photographs of a gel containing 7 variants from NA05. In this FIG., the fusion protein band is labeled for variant NA05.6. Table 2 provides a ranking of 6 variants. The data were normalized and a performance index was calculated. The data clearly show that NA05.6 produces significantly larger quantities of fusion protein compared to the fusion construct pME27.1.

TABLE 2

Sequence of Six Variants with Largest Improvement in Stability

| Clone | Mutations from CAB1 |
|---|---|
| NA05.6 | R13K, T16G, W181V |
| NA05.8 | R13K, F170Y, A234G |
| NA05.9 | K3Q, S14P, L37V, E42G, E136Q, M146V, W181V, A234G |
| NA05.10 | K3Q, L37V, P170Y, W181V |
| NA05.12 | K3Q, S14P, L37V, M146V |
| NA05.15 | M146V, F170Y, A194D |

Construction of Library NA06

Clone NA05.6 (designated a CAB1.1) was chosen as the best variant and was used as the template for a second round of combinatorial mutagenesis clone. A subset of the same mutagenic primers used to generate library NA05 were used to generate combinatorial variants of NA05.6 with the following mutations: K3Q, L37V, E42G, E136Q, M146V, F170Y, A194D, A234G. The mutations were identified in other winners from library NA05. The primer encoding mutation S14P was not used, as its sequence overlapped with mutations R13K and T16G present in NA05.6 (CAB1.1). A combinatorial library was constructed using QuikChange Multisite kit as described above and was referred to as "NA06." The template was pNA05.6 and 1 µl of primers mix (10 µM stock of all primers combined containing 1.25 µM each primer) were used to produce the library using the same methods as described above.

Screening of Library NA06

The screen was performed as described above, but with some modifications, as described below. In these screens, 291 variants were screened on 3 96-well plates. First, 10 µl samples from the lysate plates were added to 180 µl of 10 µg/ml thermolysin (Sigma) in 50 mM imidazole buffer pH 7.0 containing 0.005% TWEEN®-20 and 10 mM calcium chloride. This mixture was incubated for 1 h at 37° C. to hydrolyze unstable variants of NA05.6 (CAB1.1). This protease-treated sample was used to perform the CEA-binding assay as described above.

Promising variants were cultured in 2 ml medium as described above and binding curves were obtained for samples after thermolysin treatments. A number of variants were found to retain much more binding activity after thermolysin incubation than the parent NA05.6. Table 3 provides is the variants with significantly greater protease resistance as compared to the parent NA05.6

TABLE 3

Variants Significantly More Protease-Resistant than NA05.6 (CAB1.1)

| Clone | Mutations |
|---|---|
| NA06.2 | R13K, T16G, W181V, L37V, E42G, A194D |
| NA06.4 | R13K, T16G, W181V, L37V, M146V |
| NA06.6 | R13K, T16G, W181V, L37V, M146V, K3Q |
| NA06.10 | R13K, T16G, W181V, L37V, M146V, A194D |
| NA06.11 | R13K, T16G, W181V, L37V, K3Q, A194D |
| NA06.12 | R13K, T16G, W181V, L37V, E136Q |

As indicated above, all 6 variants had the mutation L37V. In contrast, this mutation was rare in randomly chosen clones from the same library. Further testing showed that variant NA06.6 had the highest level of total BLA activity and the highest protease resistance of all variants. Thus, NA06.6 was chosen for further development and designated as "CAB1.2."

Example 2

Specificity and Localization of Staining in Viable Mixed Cell Cultures

Figure 2B:
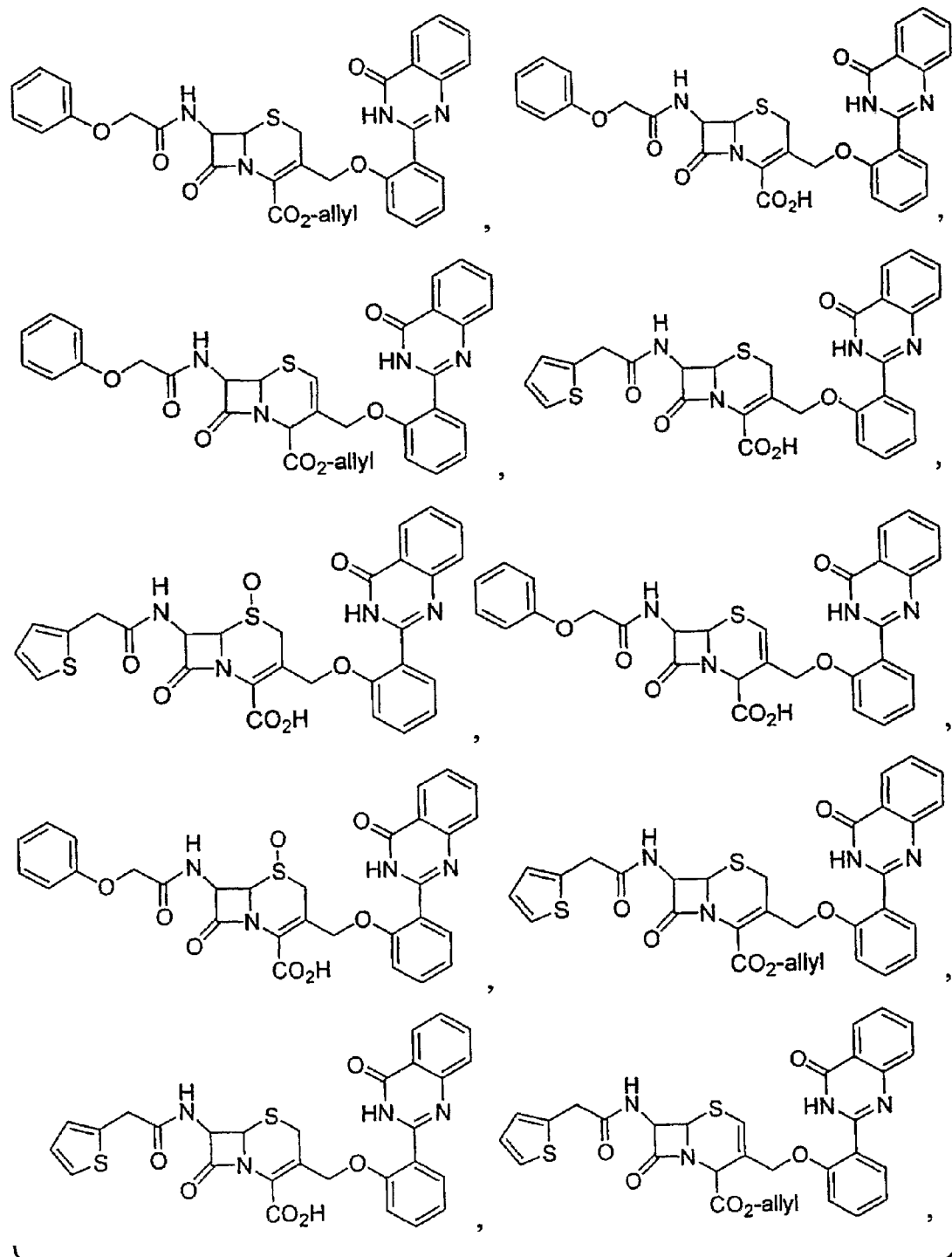
Figure 2C:
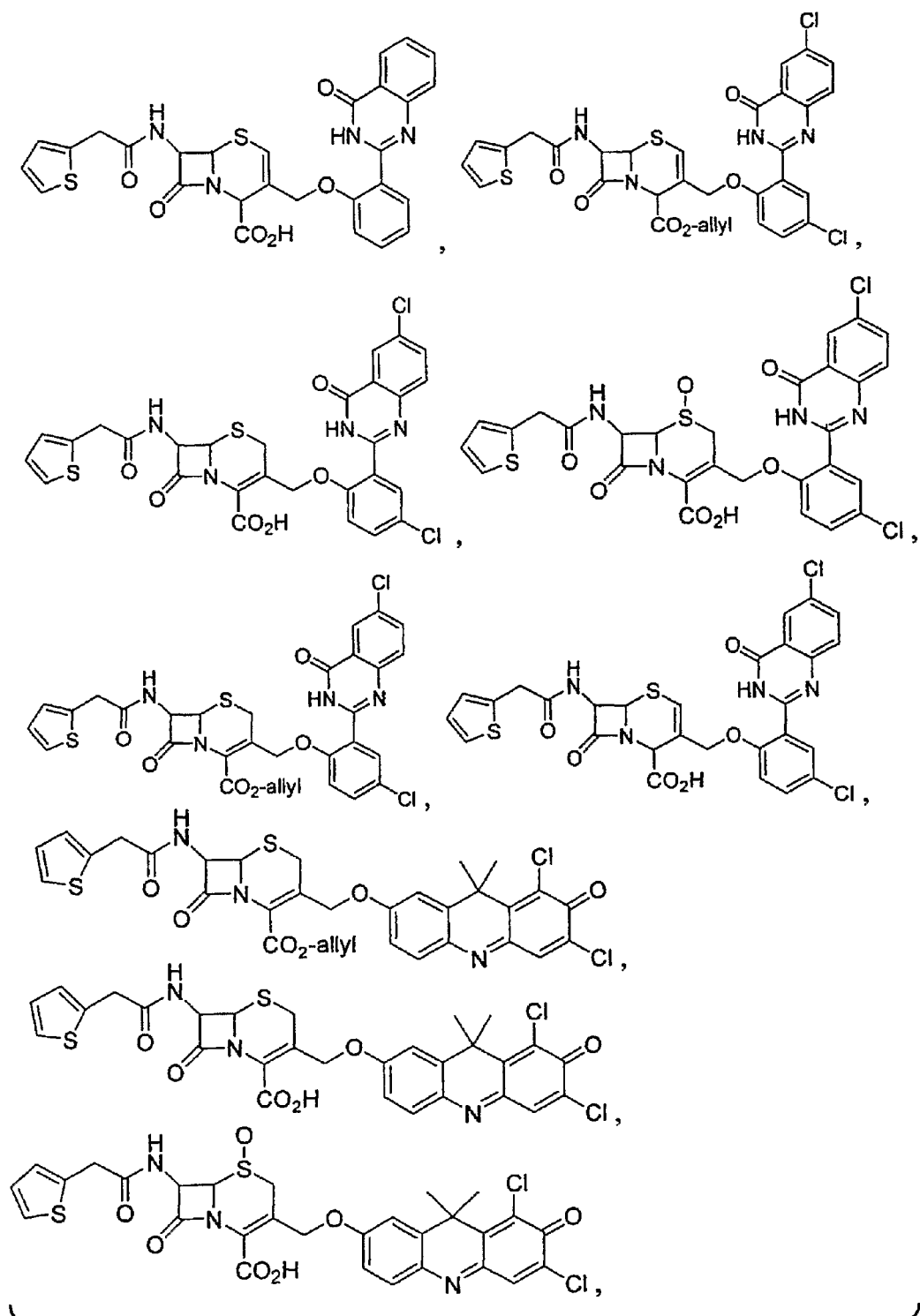
Figure 2D:
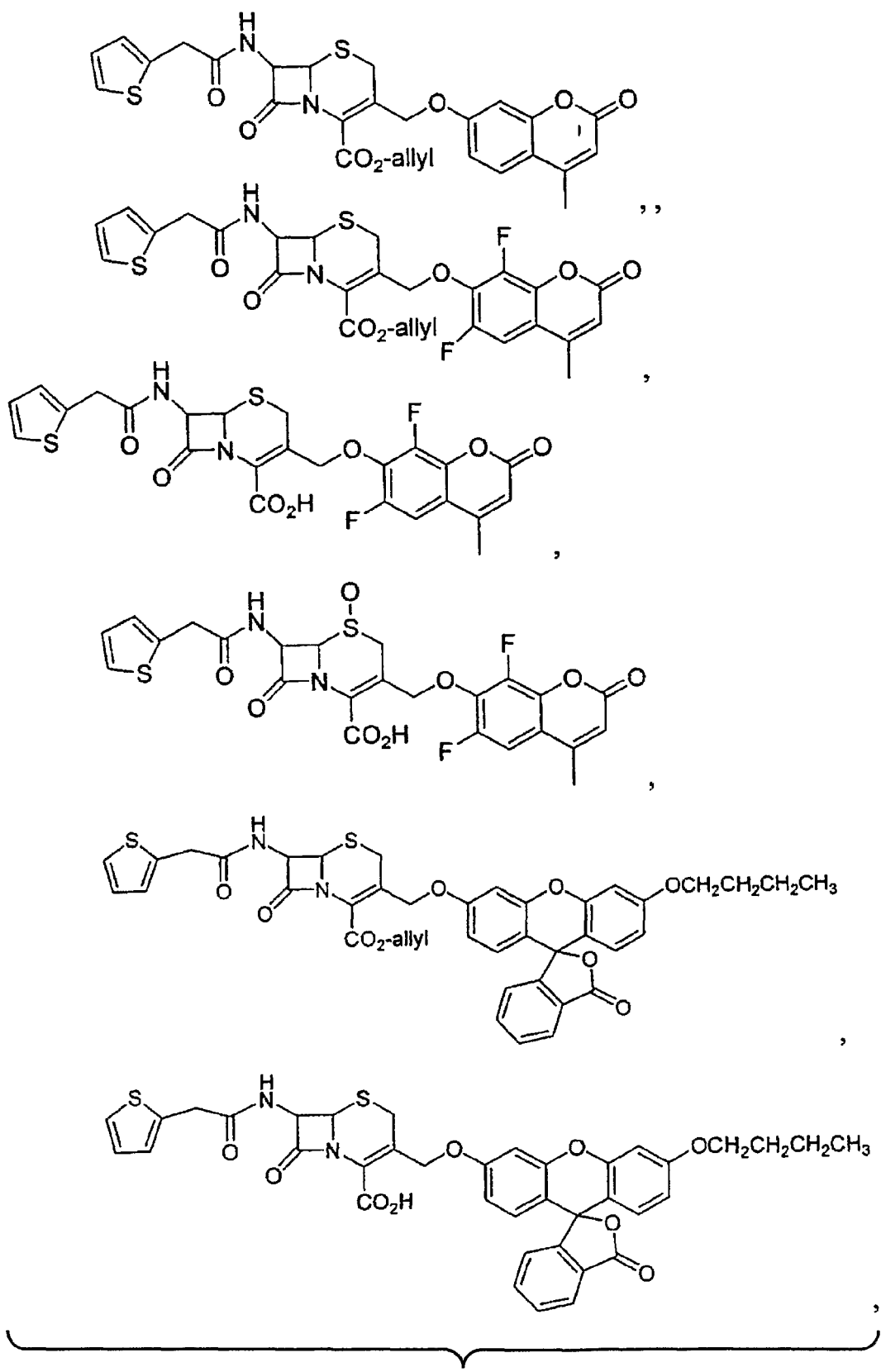
Figure 2F:
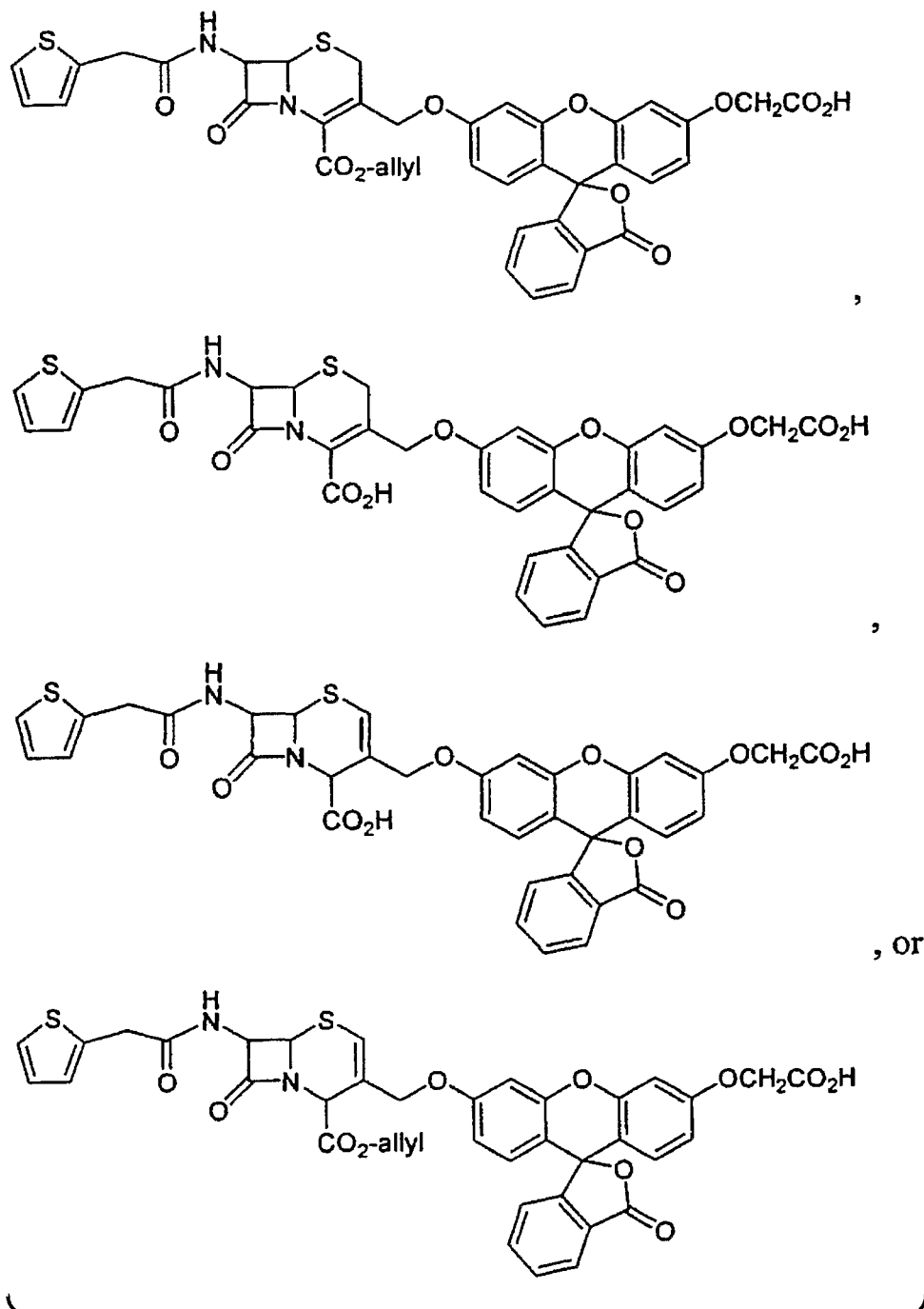

In this Example, experiments conducted to determine the specificity and localization of staining in mixed cell cultures using sc-Fv-BLA fusion protein targeted to CEA in viable cultured cells are described. In these experiments, MC38 and MC38 CEA+ cells were used (MC38 cells are a mouse fibroblast cell line and MC38 CEA+ are fibroblasts from a transgenic mouse expressing human carcinoembryonic antigen (CEA)). Cells of both lines were cultured in standard growth medium (50:50 DMEM/Ham's F12 media) supplemented with 10% fetal bovine serum, non-essential amino acids, glutamine and pyruvate. Cells were grown at 37° C. in a 5% $CO_2$ atmosphere using standard cell culture methods as known in the art. Medium was removed from cells, and the cells were then washed in phosphate buffered saline (PBS). CEA-targeted beta-lactamase-scFv with a CAB molecule (See, Example 1, and FIG. 12) was added at 1 ug/ml in PBS and allowed to bind at room temp for approximately 30 minutes. Substrate, as shown in FIG. 2A, was added. Cells were washed twice with PBS and MPR added as a 10 uM solution in PBS and allowed to react for 3 minutes at which time excess substrate was washed off.

The cells were observed using fluorescence microscopy with a filter set to have 350 nm excitation and 585 nm emission optics. Photographs were taken of the cells using a Leica DMRA fluorescence microscope and a Hamamatsu Orca CCD camera and image processed with Image Pro software.

Figure 3:
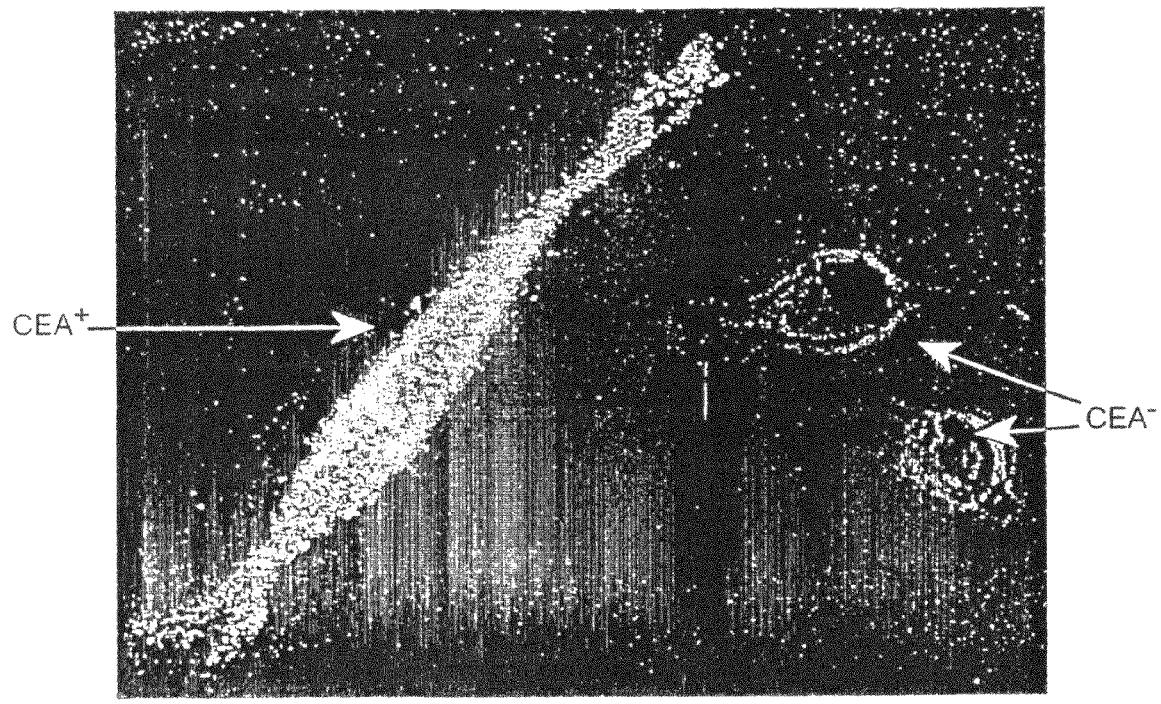
FIG. 3 shows the specificity and localization of staining in mixed cell culture using a carcinoembryonic antigen (CEA) antibody binding (CAB) molecule. As indicated in this photograph, a marked morphological difference is observable between CEA+ (i.e., cells bearing the CEA antigen) and non-CEA cells (i.e., cells lacking the CEA antigen). Marked staining differences are also observable between the cells.

The results are provided in FIG. 3. As shown in FIG. 3, viable, non-fixed cells can be stained with beta-lactamase and substrate and labeling is specific for antigen bearing cells. In addition, this Figure shows that there are observable morphological differences between CEA+ and non-CEA cells, with the former being elongated (cell on the left side of the photgraph) and the latter being less elongated (cell on right side is not). Using this method, CEA+ cells stained green, while CEA- cells do not stain, but appear red in photomicrographs.

Example 3

Specificity and Localization of Staining in Fixed Mixed Cell Culture

In this Example, experiments conducted to determine the specificity and localization of staining in mixed cell cultures using sc-Fv-BLA fusion protein targeted to CEA in formaldehyde-fixed cultured cells are described. The methods used were similar to those described in Example 2. In these experiments, LSI 74T (CEA+ LS174T colon carcinoma cells) and MRC5 (diploid human fibroblasts; ATCC) were co-cultured as described above, fixed for 10 minutes at room temperature with 3% formaldehyde (Polysciences), then stained as described above in Example 1, with 0.5 ug/ml stain. Then, substrate (See, FIG. 2A) was added in distilled water.

The cells were observed using fluorescence microscopy with a filter set having 350 nm excitation and 585 nm emission optics. Imaging was performed with a Leica DMRA fluorescence microscope and a Hamamatsu Orca CCD camera and image processed with Image Pro software.

As indicated by the results shown in FIG. 4, cell fixation does not impair binding of catalytic activity of the enzyme.

Example 4

Specificity and Localization of Staining in Flash-Frozen Mixed Cell Culture In this Example, experiments conducted to determine the specificty and localization of staining in mixed culture using CAB 1.2 and flash-frozen tissue are described. LS174T CEA-expressing colon carcinoma cells were xenografted into nude mice using methods known in the art. Sixty female mice were implanted with tumor derived TLS174T cells by subcutaneous injection suspended in DMEM media at $5 \times 10^7$ cells/mL. Animals were anesthetized by isoflurane inhalation, and cells will be implanted by subcutaneous injection of 100 uL cell suspension (approximately $5 \times 10^6$ cells/mouse).

Tumor size at time of sacrifice was approximately 100 $mm^3$. Following sacrifice, tumors were excised and flash frozen in liquid nitrogen. Frozen tumors were sectioned to produce tissue slices of approximately 10 micron thickness on a Leica cryostat using standard procedures as known in the art (See e.g., Kierman, *Histological and Histochemical Methods: Theory and Practice*, Oxford University Press, [2003]. Tissue sections were permeabilized with cold acetone, air-dried, and then blocked with PBS containing 2% fetal bovine serum. CAB1.2 was applied (1 ug/ml) in PBS/FBS for approximately 30 minutes and subsequently washed off. A commercially available anti-human pan-cytokeratin antibody (directly labeled with fluorescein isothiocyanate, DAKO; clone MNF116) was used to specifically label human cancer cells and applied simultaneously with CAB1.2 for 30 minutes at room temperature. Substrate (See, FIG. 2A), was added. Subsequently, the tissues were washed with PBS to remove unbound fusion protein and antibody and MPR substrate was added in distilled water.

As described above, the cells were observed using fluorescence microscopy with a filter set having 350 nm excitation and 585 nm emission optics. Imaging was performed with a Leica DMRA fluorescence microscope and a Hamamatsu Orca CCD camera and image processed with Image Pro software.

As shown in FIG. 5, binding and enzymatic activity are unaffected by freezing the tissues. Likewise, the Figure also shows that labeling with fusion protein and substrate is specific and restricted to human cancer tissue (cytokeratin positive, CEA positive) and not normal mouse tissue (cytokeratin and CEA negative). Finally, as shown by FIG. 5, protein-substrate staining does not cross-react with mouse tissue and substrate does not bind non-specifically to tissues mouse tissue.

Example 5

Human and Tissue Microarray (TMA) Comprising Normal and Cancer Tissues

In this Example development of tissue microarrays are described. Paraffin-imbedded tissue microarrays were obtained from commercial sources (Cemicon). Following deparaffinization in xylene, dehydration in ethanol, and rehydration in water following standard procedures, TMAs were blocked in PBS/FBS and CAB 1.2 was applied at 1 ug/ml. Binding was performed at room temp for approximately 1 hr, followed by washing in PBS and distilled water. Substrate was applied at 10 uM for 5 minutes and the slides thoroughly washed in distilled water.

The slides were observed using a BioRad Model XF imager set for UV excitation and 500 longpass filter (Leica). The slides were also scored by eye for gross level of antigen expression (scale 0-4, no to high expression, substrate fluorescence). These results were then correlated with tissue types, based on the vendor's key to the TMA.

Figure 6A:
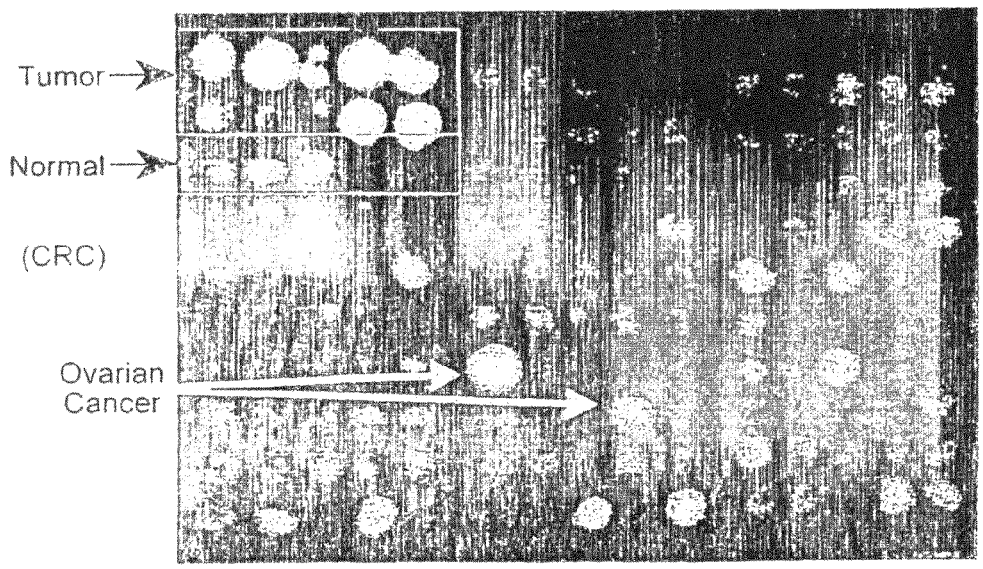
FIG. 6 provides results from a human tissue microarray ("TMA") comprising normal and cancer tissues. Panel 6A shows TMA staining, while Panel 6B provides a graph that illustrates staining intensity. In Panel 6B, the y-axis shows the mean staining intensity in the positive area of staining, while the x-axis indicates the type of tissue.
Figure 6B:
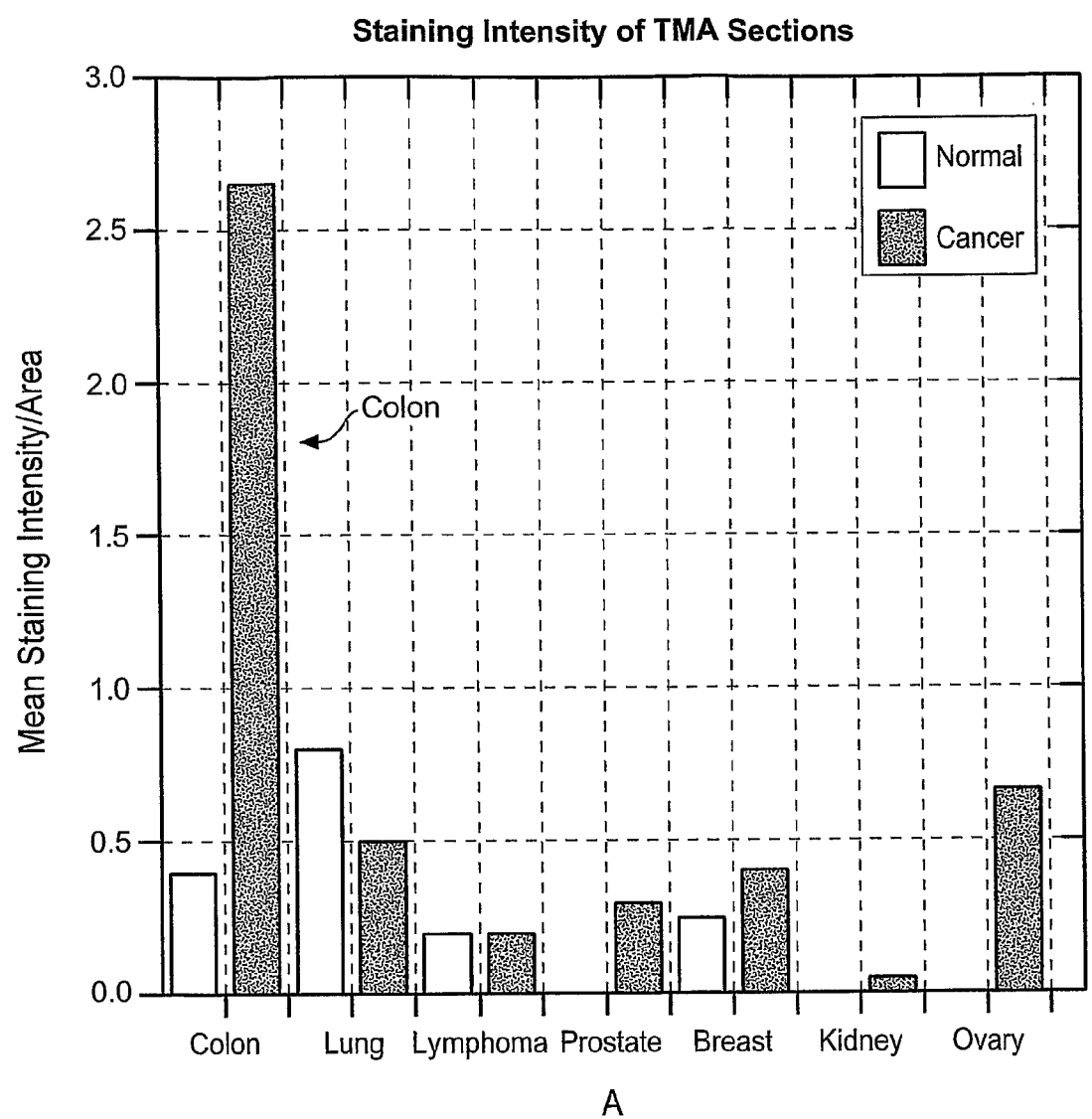

The results are shown in FIG. 6. FIG. 6A shows TMA staining, while FIG. 6B shows staining intensity. The y-axis indicates the mean staining intensity/area of staining, while the x-axis shows the type of tissue.

Example 6

High Magnification Observation of TMA

In this Example, experiments conducted on two individual tissue samples are described. Two individual tissue sections from the TMA described above were imaged at higher magnification. This higher magnification was conducted using a BioRad Model FX imager with UV excitation and a 500 longpass filter.

Figure 7:
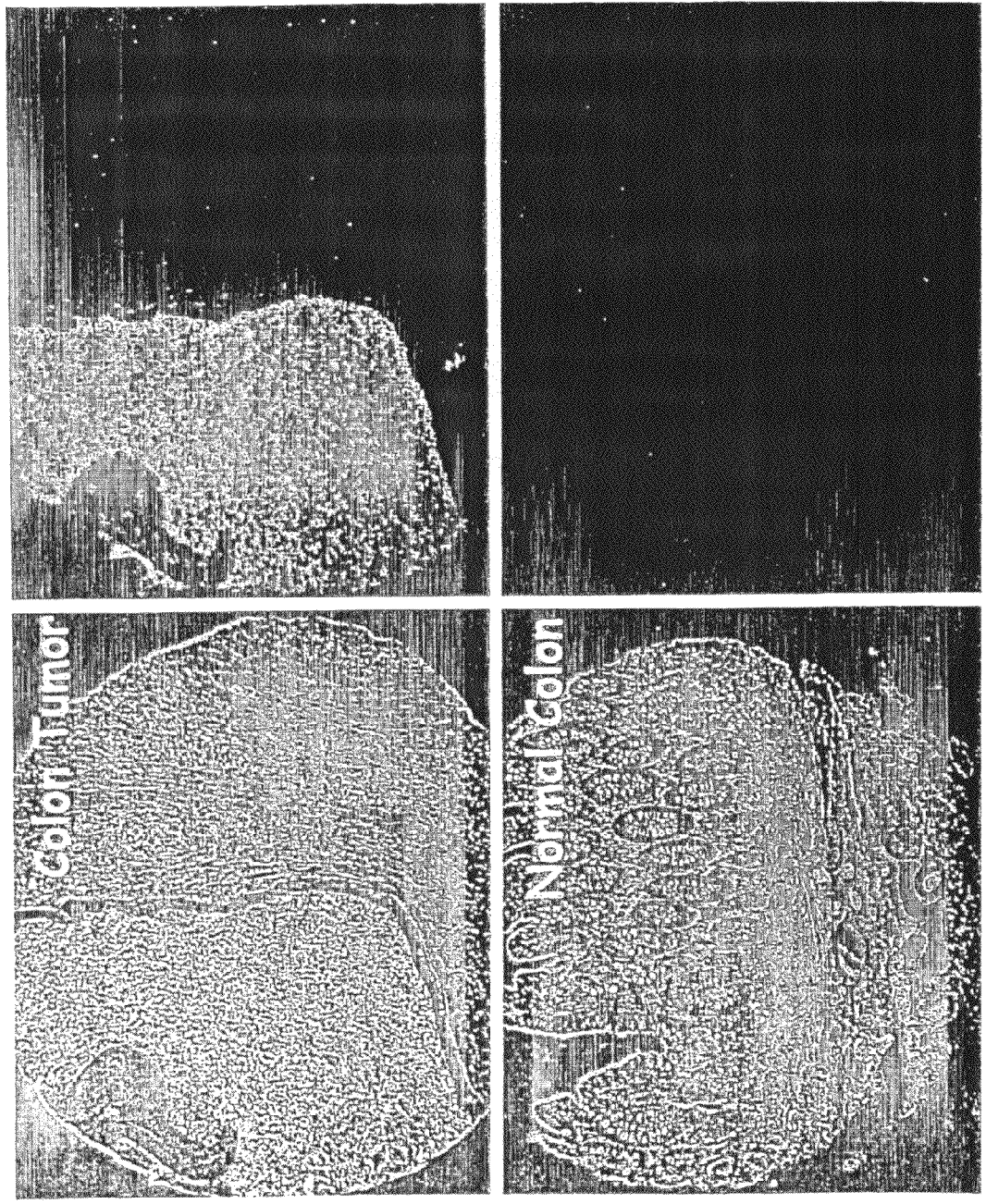
FIG. 7 shows individual elements of a TMA, as described in Example 6.

The results are shown in FIG. 7. Excellent specific staining of disease (colon cancer) but not normal human colon tissue (both on the same array) were observed. In addition, there was a good signal:noise ratio for targeted BLA and substrate.

Example 7

Specific Staining of Paraffin Embedded Normal Monkey Colon Tissue with CAB1.2

In this Example, experiments conducted to observe the specific staining of paraffin-embedded normal monkey tissue with CAB 1.2 are described. Following deparaffinization in xylene, dehydration in ethanol, and rehydration in water following standard procedures, tissues were blocked in PBS/FBS, and CAB 1.2 was applied at 1 ug/ml. Binding was performed at room temp for approximately 1 hr, followed by washing in PBS and distilled water. Substrate was applied at 10 uM for 5 minutes and slides thoroughly washed in distilled water. Following staining, tissues were mounted in PBS containing 1 ug/ml propidium iodide (red) as a counterstain.

The tissues were observed using a Leica DMRA microscope fitted with spectral filters (Qdot 525 and Qdot585 filter sets; Omega) and using a BioRad Model FX gel imager using UV excitation and 500 longpass filter.

Figures 8A, 8B:
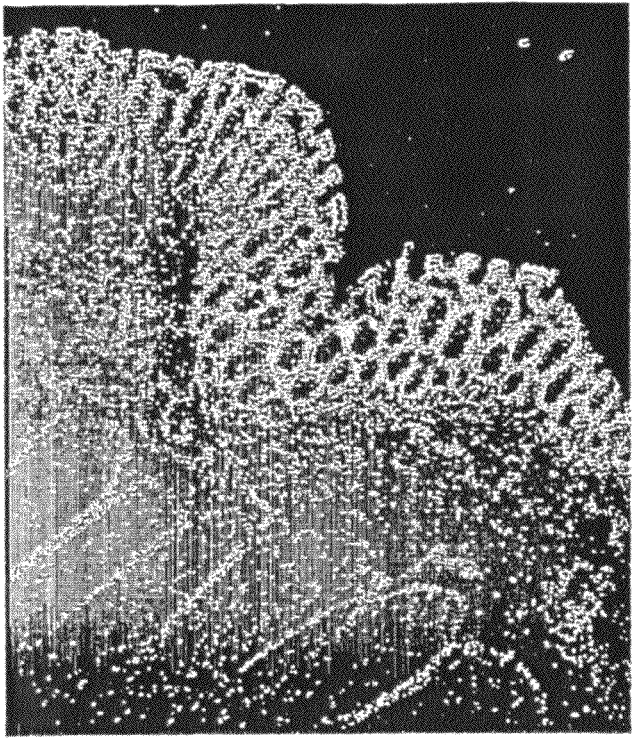
FIG. 8 provides micropbotographs of stained paraffin-embedded normal monkey colon tissue with CAB1.2. In Panel A, the sample lacked BLA, but contained substrate. In Panel B, BLA and substrate were both present. As can be seen from the picture, the staining of sections is specific and bright.

The results are shown in FIG. 8. As indicated in FIG. 8, there is a distinct and specific pattern of staining.

Example 8

Multiple TMA Staining for High-Throughput Tissue Array Screening

In this Example experiments conducted to develop multiple TMA staining methods for high throughput tissue array screening for specific antigen expression in diseased and normal tissues are described. First, 10 tissue arrays (Ardais) were simultaneously prepared and stained for CEA expression as described herein. Following deparaffinization in xylene, dehydration in ethanol, and rehydration in water following standard procedures, TMAs were blocked in PBS/FBS and CAB 1.2 was applied at 1 ug/ml. Binding was performed at room temp for approximately 1 hr, followed by washing in PBS and distilled water. Substrate (See, FIG. 2A) was applied at 10 uM for 5 minutes and the slides were thoroughly washed in distilled water.

Figure 9:
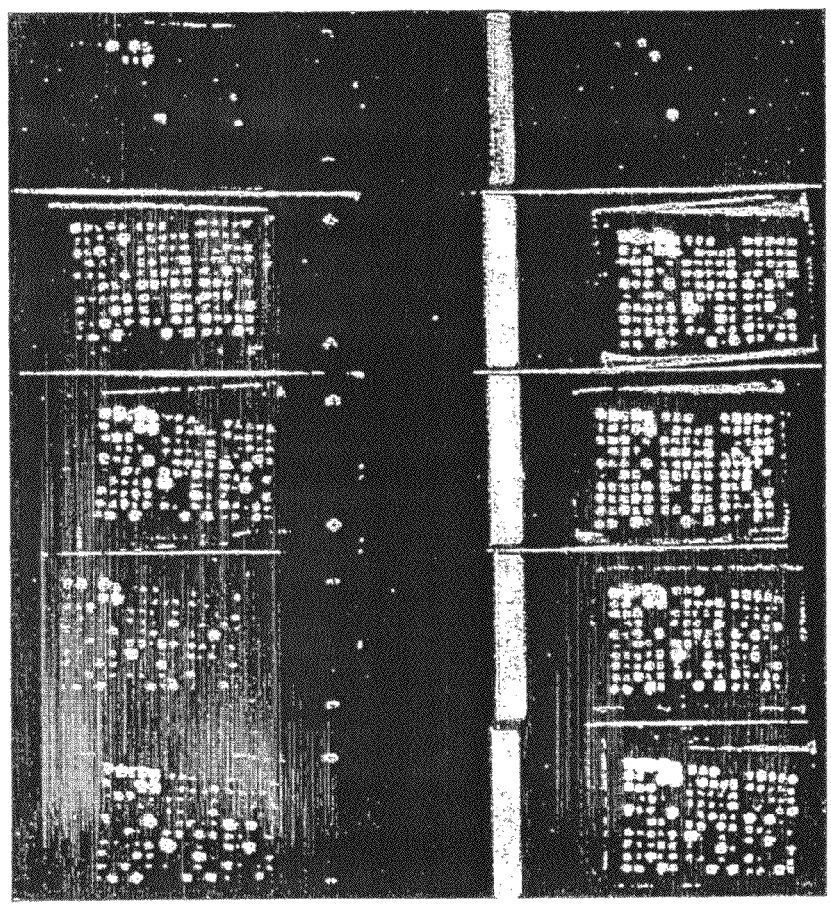
FIG. 9 provides photographs of multiple TMAs stained for high-throughput tissue array screening for specific antigen expression in normal and diseased tissue.
Figure 11:
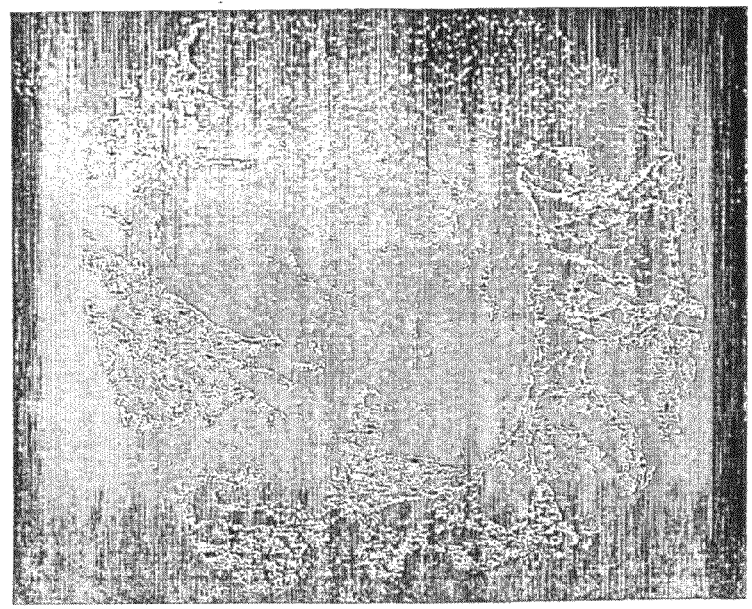
FIG. 11 provides a photomicrograph of paraffin-embedded human colon cancer tissue stained with biotinylated anti-CEA (Biomeda), streptavidin and biotinylated beta-lactamase followed by substrate.

The slides were observed using a BioRad Gel Documentation imager and the images were processed with Quantity-One software (BioRad). The results are shown in FIG. 9. These results indicate that the use of CAB1.2 and substrate permit rapid staining and evaluation of multiple TMAs.

Example 9

Method for Coupling Beta-Lactamase to Antibodies

Figure 10:
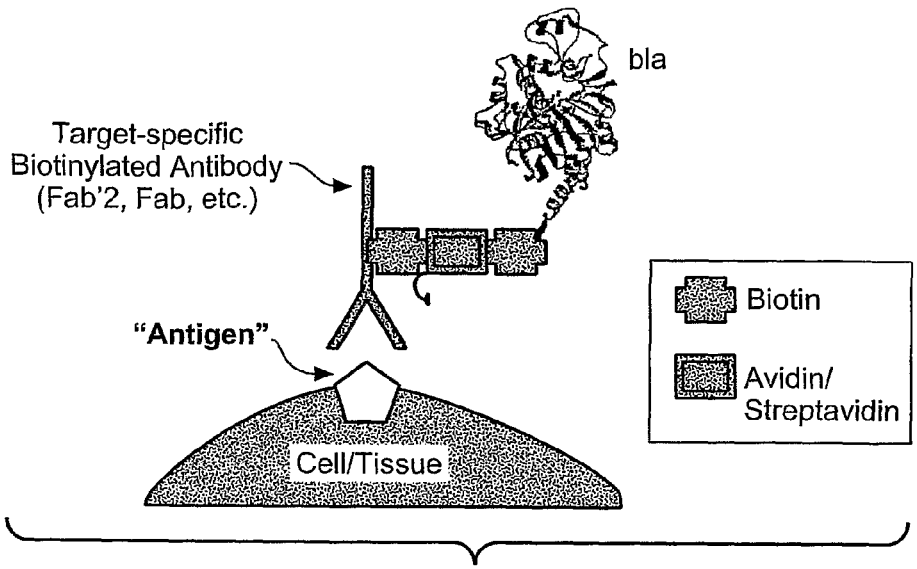
FIG. 10 provides a schematic showing a general method for coupling beta-lactamase to antibodies, as described in Example 9.

In this Example, a method for coupling beta-lactamase to antibodies is described. In some embodiments, biotinylated beta-lactamase is bound to a biotinylated antibody which is itself bound to a specific antigen target, using avidin or streptavidin as shown in FIG. 10. In this format, any antigen for which a biotinylated antibody exists can be stained using beta-lactamase and the substrate. In some embodiments, this is accomplished by binding primary biotinylated antibody to target cells/tissue using standard methods (See e.g., Boenisch (ed.), *Handbook of Immunochemical Staining Methods*, DAKO Corp, [2001]), and then washing out unbound antibody and adding either avidin or biotin and allowing binding to antibody. After washing off unbound streptavidin, biotinylated beta-lactamase is added and allowed to bind to streptavidin. Unbound beta-lactamase is removed and substrate is added.

Example 10

In Vivo Staining

In this Example, experiments to show in vivo staining using the methods of the present invention are described. Mice bearing CEA+ xeongraft tumors (LS174T colon carcinoma cells, ATCC) were treated with a CAB 1.2 (i.e., a CEA specific targeted lactamase), at 0.5 mg/Kg. Then, 24 hrs later, anesthetized mice Avere injected with a fluorescent lactamase substrate and substrate allowed to circulate for approximately 10 minutes. Mice were sacrificed by cervical dislocation and the tissues were observed using a Kodak 2000MM imager with excitation and emission filters appropriate for fluorophores. Several excitation and emission spectra were used, (e.g., 525 nm emission, 514 nm excitation and 650 nm emission; See FIG. 17). The images were collected and processed with the computer hardware and software associated with the microscope. The results are shown in FIG. 16.

Those of skill in the art readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not.

Intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations that is not specifically disclosed. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed be some preferred embodiments and optional features, modification and variation of the disclosed concepts may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A method for detecting at least one target on at least one cell, comprising the steps of:
   a) providing at least one test cell having at least one target;
   b) contacting said at least one test cell to a targeted agent, such that the targeted agent binds to the target to form a bound target,
      wherein said agent is conjugated to a β-lactamase enzyme,
      wherein said enzyme is capable of cleaving a substrate, wherein said substrate is a precipitating fluorogenic lactamase molecule;
   c) contacting said bound target to said substrate to produce a detectable precipitating fluorescent product that adheres to said at least one target under conditions such that said enzyme cleaves said substrate to produce said detectable product; and
   d) detecting said adherent product, on the at least one target on the at least one cell.

2. The method of claim 1, wherein said at least one test cell is obtained from an animal.

3. The method of claim 2, wherein said at least one test cell is a human cell.

4. The method of claim 1, wherein said targeted agent is selected from the group consisting of monoclonal antibodies, polyclonal antibodies, and fragments of said antibodies.

5. The method of claim 4, wherein said targeted agent is biotinylated.

6. The method of claim 1, wherein said substrate is biotinylated.

7. The method of claim 1, wherein said at least one cell is in vitro, in vivo, ex vivo, or in situ.

8. A method for detecting at least one target on at least one cell, comprising the steps of:
   a) providing at least one test cell having at least one target;
   b) contacting said at least one test cell to a targeted agent that binds to said target, such that the targeted agent binds to the target to form a bound target, wherein said agent is conjugated to a β-lactamase enzyme;
   c) providing a substrate that is a precipitating fluorogenic lactamase molecule, wherein said enzyme is capable of cleaving said substrate to produce a detectable product;
   d) contacting said bound target to said substrate under conditions such that said enzyme cleaves said substrate to produce a detectable precipitating fluorescent product that adherers to said at least one target on said at least one test cell; and
   e) detecting said adherent product on the at least one target on said at least one cell.

9. The method of claim 8, wherein said at least one test cell is obtained from an animal.

10. The method of claim 9, wherein said at least one test cell is a human cell.

11. The method of claim 9, wherein said targeted agent is biotinylated.

12. The method of claim 8, wherein said targeted agent is selected from the group consisting of monoclonal antibodies, polyclonal antibodies, and fragments of said antibodies.

13. The method of claim 8, wherein said substrate is biotinylated.

14. The method of claim 8, wherein said β lactamase enzyme is biotinylated.

15. The method of claim 8, wherein said β lactamase enzyme binds to said bound target due to binding between biotin and streptavidin/avidin.

16. The method of claim 8, wherein said at least one cell is in vitro, in vivo, ex vivo, or in situ.

17. The method of claim 8, wherein said targeted agent and said β lactamase enzyme are coupled to produce a fusion protein.

* * * * *